(12) United States Patent
Emmanuel et al.

(10) Patent No.: US 9,062,056 B2
(45) Date of Patent: Jun. 23, 2015

(54) AZA-BENZIMIDAZOLONE CHYMASE INHIBITORS

(75) Inventors: Michel Jose Emmanuel, New Fairfield, CT (US); Xin Guo, Danbury, CT (US); Jin Mi Kim, Sandy Hook, CT (US); Ho Yin Lo, Bethel, CT (US); Peter Allen Nemoto, Southbury, CT (US); Kevin Chungeng Qian, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 410 days.

(21) Appl. No.: 13/062,749

(22) PCT Filed: Aug. 25, 2009

(86) PCT No.: PCT/US2009/054830
§ 371 (c)(1),
(2), (4) Date: May 19, 2011

(87) PCT Pub. No.: WO2010/030500
PCT Pub. Date: Mar. 18, 2010

(65) Prior Publication Data
US 2011/0269780 A1    Nov. 3, 2011

Related U.S. Application Data

(60) Provisional application No. 61/095,335, filed on Sep. 9, 2008.

(51) Int. Cl.
*C07D 471/04* (2006.01)
*C07D 487/04* (2006.01)

(52) U.S. Cl.
CPC ............ *C07D 487/04* (2013.01); *C07D 471/04* (2013.01)

(58) Field of Classification Search
None
See application file for complete search history.

(56) References Cited

FOREIGN PATENT DOCUMENTS

| EP | 1249450 A1 | 10/2002 |
| WO | 0001704 A2 | 1/2000 |
| WO | 2007063010 A1 | 6/2007 |
| WO | 2007068621 A1 | 6/2007 |
| WO | WO 2008147697 A1 * | 12/2008 |
| WO | 2009023655 A1 | 2/2009 |

OTHER PUBLICATIONS

George A. Patani and Edmond J. LaVoie. Bioisosterism: A Rational Approach in Drug Design. Chem. Rev. 1996, 96, 3147-3176.*
International Search Report for PCT/US2009/054830 filed Aug. 25, 2009.

* cited by examiner

*Primary Examiner* — Marcos Sznaidman
*Assistant Examiner* — Rayna B Rodriguez
(74) *Attorney, Agent, or Firm* — Michael P. Morris; Usha R. Patel

(57) ABSTRACT

Disclosed are small molecule inhibitors of the formula (I): and the pharmaceutical compositions thereof and processes of making the same. The compounds are useful in treating various diseases and conditions involving chymase.

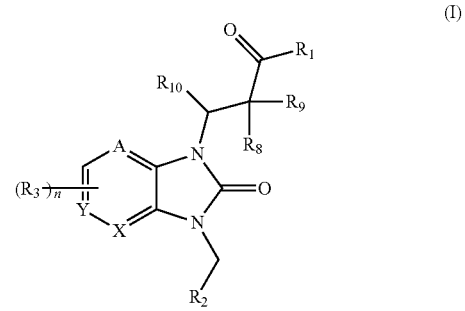

2 Claims, No Drawings

AZA-BENZIMIDAZOLONE CHYMASE INHIBITORS

APPLICATION DATA

This application claims benefit is U.S. provisional application Ser. No. 61/095,335 filed Sep. 9, 2008.

FIELD OF THE INVENTION

The invention relates to small molecule inhibitors which are useful in treating various diseases and conditions involving Chymase.

BACKGROUND OF THE INVENTION

In cardiac tissue of cardiomyopathic patients, transforming growth factor-β (TGF-β), which has been demonstrated to stimulate cardiac fibrosis in animal models (Kuwahara, et al. Circulation, 2002, 106, 130), is increased (Li et al., Circulation, 1997, 96, 874). In the myocardial fibrotic area, it is known that mast cells are increased in number and may contribute to the development of fibroblast proliferation in cardiac tissues of patients with cardiomyopathy (Patella et al., Circulation, 1998, 97, 971). Chymase is a chymotrypsin-like serine protease contained in the secretory granules of mast cells. Although the precise physiological roles of Chymase have not been completely revealed, Chymase is known to transform angiotensin I to angiotensin II and may contribute to activation of TGF-β, matrix proteases, and cytokines (Taipale et al., J. Biol. Chem., 1995, 270, 4689; Takai et al., Life Sci., 1996, 58, 591; Takai et al., Circulation, 1999, 100, 654).

A potent and selective Chymase inhibitor may have potential use as a treatment of chronic heart failure, atherosclerosis, restenosis, and myocardial infarction by inhibiting local production of angiotensin II in the heart and release of TGF-β, two independent mediators of cardiac remodeling. An inhibitor may also have potential use for treatment of mast cell mediated diseases such as dermatitis, asthma, chronic obstructive pulmonary disease (COPD), and pulmonary inflammation, since Chymase is implicated in microvascular leakage, neutrophil accumulation, the stimulation of mucus secretion, and the modulation of cytokines (He et al., Eur. J. Pharmacol., 1998, 352, 91).

Several small molecule Chymase inhibitors have been reported to be efficacious in the cardiomyopathic hamster model of heart failure (Takai et al. J. Pharmacol. Exp. Ther. 2003, 305, 17), in carotid artery injury by a balloon catheter in dogs (Takai et al. J. Pharmacol. Exp. Ther, 2003, 304, 841), and in the hamster left anterior descending coronary artery ligation model of heart failure (WO 03/018061). Additionally, a Chymase inhibitor has been demonstrated to be efficacious in a sheep asthma model (WO 2005/073214). However, there is no example of commercialization of a Chymase inhibitor as a medicament.

SUMMARY OF THE INVENTION

It is therefore an object of the invention to provide a small molecule a Chymase inhibitor as defined herein, and pharmaceutical compositions thereof.

It is also an object of the invention to provide methods of using said Chymase inhibitors to treat various diseases and conditions related thereto.

It is a further object of the invention to provide processes of preparing said Chymase inhibitors.

DETAILED DESCRIPTION OF THE INVENTION

In a first generic embodiment, there is provided a compound of the formula (I):

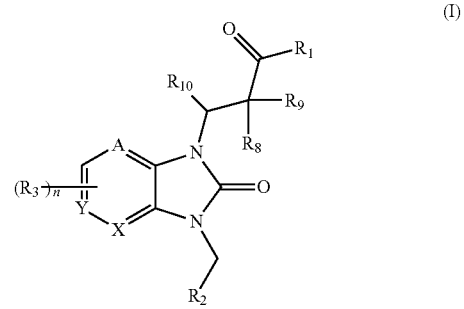

wherein:
one of A, Y or X is N and the other two are CH which forms a pyridolo ring or
A and Y are both N and X is CH which forms a pyrimidolo ring;
$R_1$ is $-SO_2R_6$, $-SO_2-NH-R_6$, $-N(R_5)-SO_2R_6$, $-NR_5R_7$, hydroxyl, $C_{1-4}$ alkoxy and aryloxy;
$R_2$ is aryl or heteroaryl each optionally substituted by halogen, $C_{1-4}$ alkyl, $C_{1-4}$ alkoxy, $C_{1-4}$ acyl, $C_{1-4}$ alkoxycarbonyl, aryl and benzyl;
$R_3$ is attached to a carbon atom on the pyridolo or pyrimidolo ring and is chosen from carboxyl, halogen, cyano, $C_{1-4}$ alkyl, $C_{1-4}$ alkoxy, $C_{1-4}$ acyl, $C_{3-7}$ cycloalkyl, $-C(O)-NR_{11}R_{12}$; $NR_{11}R_{12}$; $R_{11}$ and $R_{12}$ are independently chosen from hydrogen, $C_{1-4}$ alkyl, $C_{1-4}$ alkoxy, $C_{1-4}$ acyl, $C_{1-4}$ alkoxycarbonyl, aryl and benzyl;
$R_5$, $R_8$ and $R_9$ are independently chosen from hydrogen or $C_{1-7}$ alkyl, wherein $R_8$ and $R_9$ optionally form a $C_{3-7}$ cycloalkyl group optionally substituted by halogen, $C_{1-4}$ alkyl, $C_{1-4}$ alkoxy, $C_{1-4}$ acyl, $C_{1-4}$ alkoxycarbonyl, aryl and benzyl;
$R_6$ is chosen from $C_{1-6}$ alkyl, $C_{3-6}$ cycloalkyl, aryl and heteroaryl each optionally independently substituted with a substituents chosen from $C_{1-5}$ alkyl, $C_{1-4}$ alkoxy, halogen and cyano;
$R_7$ is chosen from hydrogen, cyano, aryl, heteroaryl, $C_{1-6}$ alkyl and $C_{3-6}$ cycloalkyl;
$R_{10}$ is chosen from hydrogen, $C_{1-7}$ alkyl, $C_{1-7}$ alkoxyl, aryl, heteroaryl, and $C_{3-6}$ cycloalkyl, each cyclic group for $R_{10}$ is optionally substituted with a substituent chosen from $C_{1-5}$ alkyl, $C_{1-4}$ alkoxy, halogen and cyano;

n=0-3;

wherein all R groups are optionally partially or fully halogenated where possible;

and wherein $R_{10}$ cannot be hydrogen if both $R_8$ and $R_9$ are hydrogen;

or a pharmaceutically acceptable salt thereof.

In another embodiment, there is provided a compound as described herein above and wherein:

$R_1$ is —N($R_5$)—SO$_2$$R_6$, hydroxyl or $C_{1-4}$ alkoxy;

$R_2$ is aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzopyrrolyl, benzothiazolyl, benzisothiazol, benzothienyl, quinolinyl, quinazolinyl, naphthyridinyl, indazolyl, triazolyl or tetrazolyl each optionally substituted by one to three halogen, $C_{1-4}$ alkyl, $C_{1-4}$ alkoxy, $C_{1-4}$ acyl, $C_{1-4}$ alkoxycarbonyl, aryl and benzyl;

$R_6$ is chosen from $C_{1-4}$ alkyl, $C_{3-6}$ cycloalkyl, aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, indazolyl, triazolyl and tetrazolyl each optionally independently substituted with a substituents chosen from $C_{1-5}$ alkyl, $C_{1-4}$ alkoxy, halogen and cyano;

$R_{10}$ is chosen from hydrogen, $C_{1-7}$ alkyl, $C_{1-7}$ alkoxyl, phenyl, $C_{3-6}$ cycloalkyl, aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, indazolyl, triazolyl and tetrazolyl, each cyclic group for $R_{10}$ is optionally substituted with a substituent chosen from $C_{1-5}$ alkyl, $C_{1-4}$ alkoxy, halogen and cyano;

n=0-1.

In another embodiment, there is provide a compound as described hereinabove and wherein:

$R_2$ is quinoxalinyl, indolyl, benzimidazolyl, benzoxazolyl, benzopyrrolyl, benzothiazolyl, benzisothiazol, benzothienyl, quinolinyl or quinazolinyl each optionally substituted by one to three $C_{1-4}$ alkyl or $C_{1-4}$ alkoxy;

$R_3$ is attached to a carbon atom on the pyridolo or pyrimidolo ring and is chosen from cyano, $C_{1-4}$ alkyl, $C_{3-6}$ cycloalkyl, $C_{1-4}$ alkoxy and NH$_2$—C(O)—;

$R_8$ and $R_9$ are independently chosen from hydrogen and $C_{1-4}$ alkyl, wherein $R_8$ and $R_9$ optionally form a $C_{3-6}$ cycloalkyl group;

$R_6$ is chosen from $C_{1-4}$ alkyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, indazolyl, triazolyl and tetrazolyl each optionally independently substituted with a substituents chosen from $C_{1-5}$ alkyl, $C_{1-4}$ alkoxy, halogen and cyano;

$R_{10}$ is chosen from hydrogen, $C_{1-7}$ alkyl, pyridinyl, pyrimidinyl, pyrazinyl, pyridazinyl, indazolyl and phenyl each cyclic group for $R_{10}$ is optionally substituted with a substituent chosen from $C_{1-4}$ alkyl, $C_{1-4}$ alkoxy and halogen.

In another embodiment, there is provide a compound as described hereinabove and wherein:

$R_2$ is indolyl, benzisothiazolyl each optionally substituted by one to three $C_{1-4}$ alkyl;

$R_6$ is chosen from $C_{1-4}$ alkyl, isoxazolyl, oxazolyl, thiazolyl, thiadiazolyl, pyrazolyl, pyrrolyl and imidazolyl, each optionally independently substituted with a substituents chosen from $C_{1-5}$ alkyl, $C_{1-4}$ alkoxy, halogen and cyano;

$R_{10}$ is chosen from hydrogen, $C_{1-5}$ alkyl, pyridinyl, pyrimidinyl, pyrazinyl, pyridazinyl, indazolyl and phenyl each cyclic group for $R_{10}$ is optionally substituted with a substituent chosen from $C_{1-4}$ alkoxy and halogen.

In another embodiment, there is provide a compound as described hereinabove and wherein:

$R_1$ is —N($R_5$)—SO$_2$$R_6$, hydroxyl, methoxy or ethoxy;

$R_2$ is indol-3-yl, benzisothiazol-3-yl each optionally substituted by one to three methyl;

$R_3$ is attached to a carbon atom on the pyridolo or pyrimidolo ring and is chosen from cyano, methyl, isopropyl, cyclopropyl, methoxy and NH$_2$—C(O)—;

$R_8$ and $R_9$ are independently chosen from hydrogen and n-propyl wherein $R_8$ and $R_9$ optionally form a cyclohexyl group;

$R_6$ is chosen from methyl, ethyl, tert-butyl and imidazolyl the imidazolyl is optionally substituted one to two methyl;

$R_{10}$ is chosen from hydrogen, n-propyl, pyridinyl and phenyl the phenyl is optionally substituted with a substituent chosen from methoxy and halogen.

In another embodiment, there is provided a compound as described in any of the embodiments hereinabove and wherein:

the

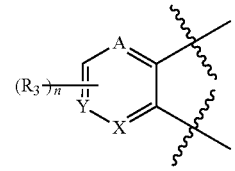

ring of the formula (I) is

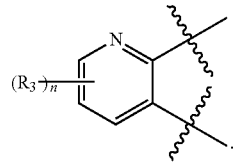

In another embodiment, there is provided a compound as described in any of the embodiments hereinabove and wherein:

the

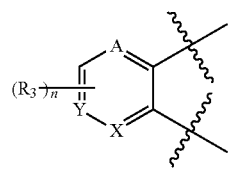

ring of the formula (I) is

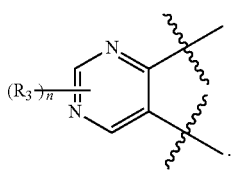

In another embodiment, there is provided a compound as described in any of the embodiments hereinabove and wherein:

the

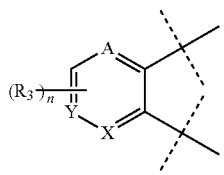

ring of the formula (I) is

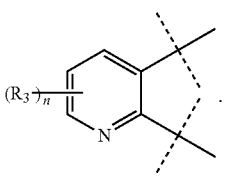

In another embodiment, there is provided compound as described in Table I which can be made as described in the schemes and examples herein below, and by methods apparent to those of ordinary skill in the art:

TABLE I

| Structure | Name |
|---|---|
| Chiral structure | (S)-3-[1-(1,4-Dimethyl-1H-indol-3-ylmethyl)-2-oxo-1,2-dihydro-imidazo[4,5-b]pyridin-3-yl]-hexanoic acid ethyl ester |
| Chiral structure | (S)-3-[3-(1,4-Dimethyl-1H-indol-3-ylmethyl)-2-oxo-2,3-dihydro-imidazo[4,5-b]pyridin-1-yl]-hexanoic acid ethyl ester |

TABLE I-continued
| | | |
|---|---|---|
| 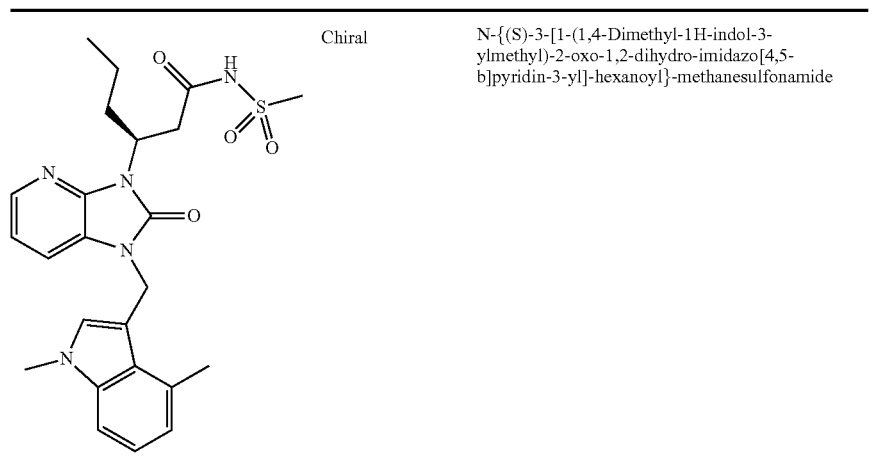 | Chiral | N-{(S)-3-[1-(1,4-Dimethyl-1H-indol-3-ylmethyl)-2-oxo-1,2-dihydro-imidazo[4,5-b]pyridin-3-yl]-hexanoyl}-methanesulfonamide |
| 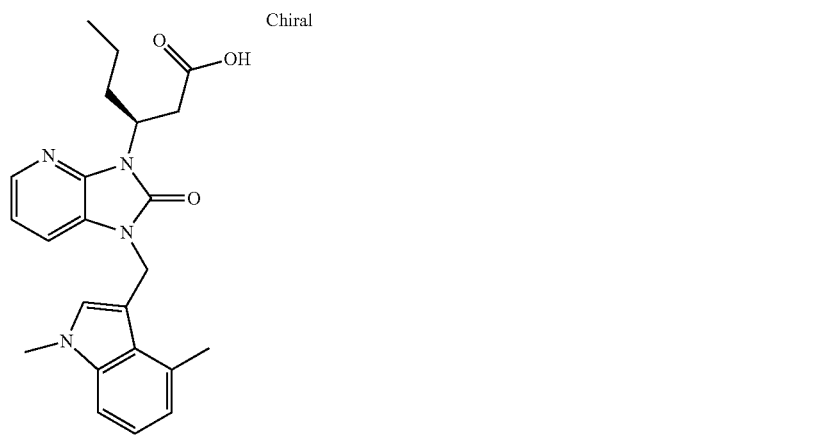 [SMILES: CCC[C@@H](CC(=O)O)n1c(=O)n(Cc2cn(C)c3cccc(C)c23)c2cccnc21] | Chiral | (S)-3-[1-(1,4-Dimethyl-1H-indol-3-ylmethyl)-2-oxo-1,2-dihydro-imidazo[4,5-b]pyridin-3-yl]-hexanoic acid |
| 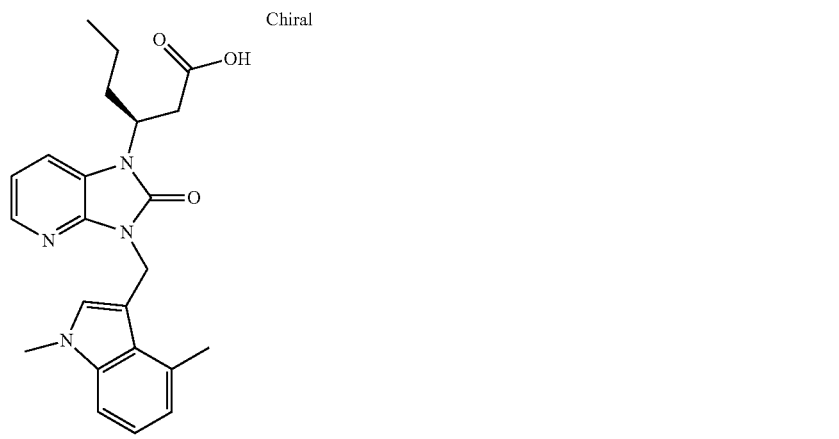 [SMILES: CCC[C@@H](CC(=O)O)n1c(=O)n(Cc2cn(C)c3cccc(C)c23)c2ncccc21] | Chiral | (S)-3-[3-(1,4-Dimethyl-1H-indol-3-ylmethyl)-2-oxo-2,3-dihydro-imidazo[4,5-b]pyridin-1-yl]-hexanoic acid |

TABLE I-continued
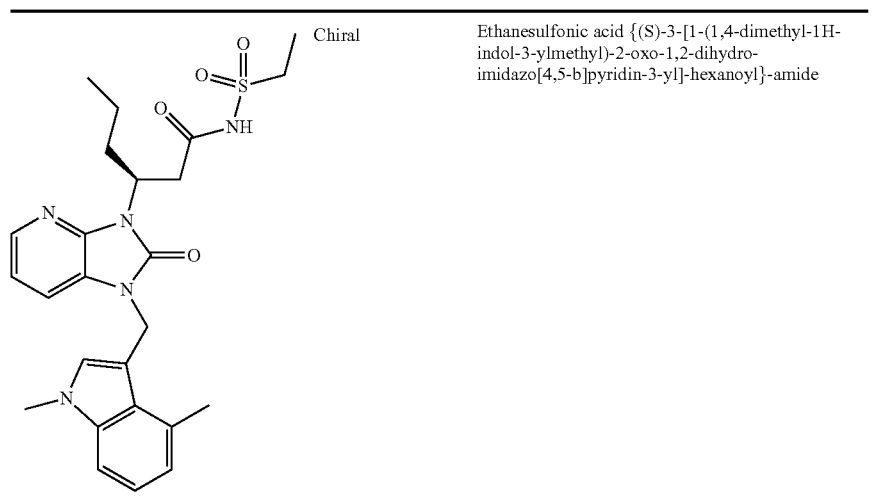
Ethanesulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide
1-Methyl-1H-imidazole-4-sulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide
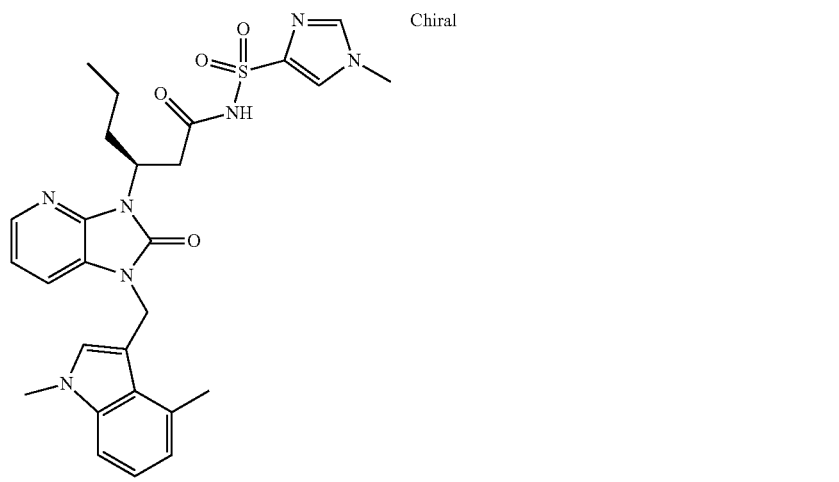 [SMILES: CCC[C@@H](CC(=O)NS(=O)(=O)c1cn(C)cn1)n1c(=O)n(Cc2cn(C)c3cccc(C)c23)c2cccnc21]
(S)-3-[3-(1,4-Dimethyl-1H-indol-3-ylmethyl)-2-oxo-2,3-dihydro-imidazo[4,5-c]pyridin-1-yl]-hexanoic acid
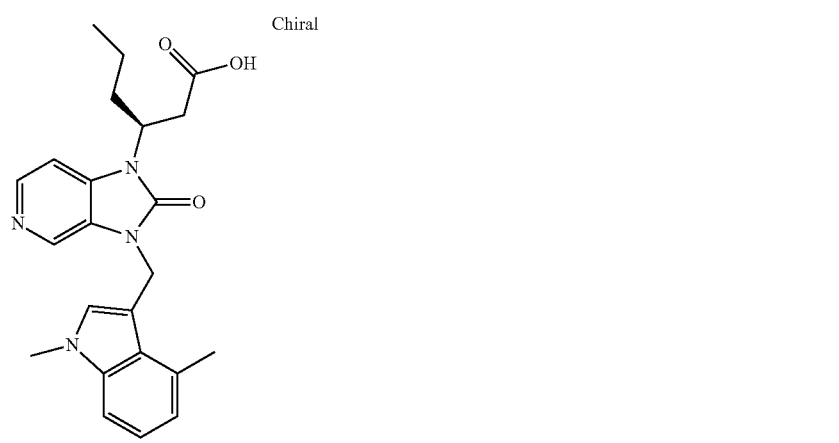 [SMILES: CCC[C@@H](CC(=O)O)n1c(=O)n(Cc2cn(C)c3cccc(C)c23)c2cnccc21]

TABLE I-continued
| Structure | Name |
|---|---|
| 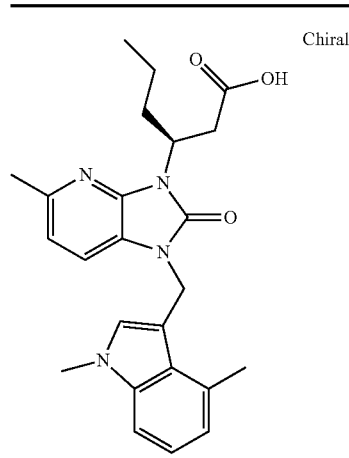 Chiral | (S)-3-[1-(1,4-Dimethyl-1H-indol-3-ylmethyl)-5-methyl-2-oxo-1,2-dihydro-imidazo[4,5-b]pyridin-3-yl]-hexanoic acid |
| 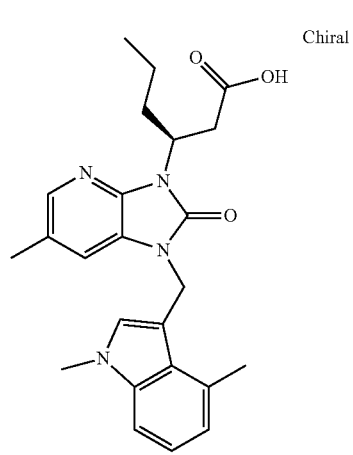 [SMILES: CCC[C@@H](CC(=O)O)n1c(=O)n(Cc2cn(C)c3cccc(C)c23)c2cc(C)cnc21] Chiral | (S)-3-[1-(1,4-Dimethyl-1H-indol-3-ylmethyl)-6-methyl-2-oxo-1,2-dihydro-imidazo[4,5-b]pyridin-3-yl]-hexanoic acid |
| 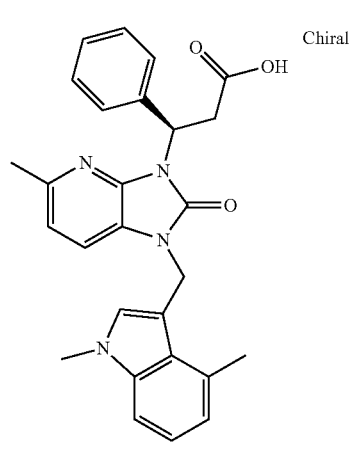 Chiral | (R)-3-[1-(1,4-Dimethyl-1H-indol-3-ylmethyl)-5-methyl-2-oxo-1,2-dihydro-imidazo[4,5-b]pyridin-3-yl]-3-phenyl-propionic acid |

TABLE I-continued
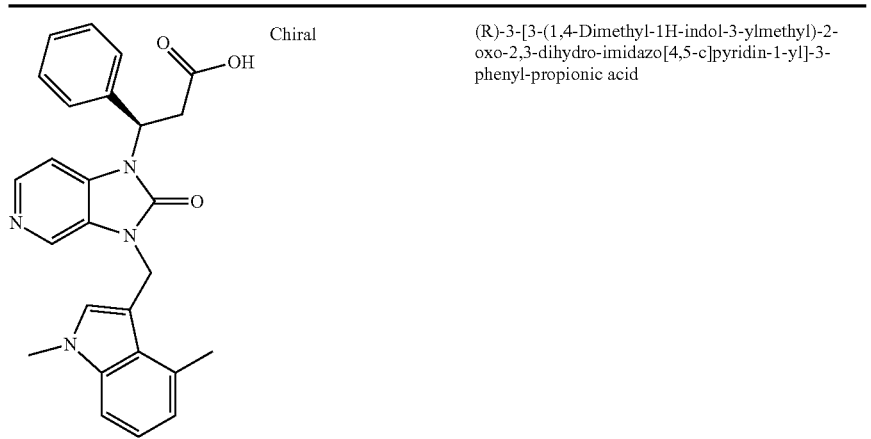
(R)-3-[3-(1,4-Dimethyl-1H-indol-3-ylmethyl)-2-oxo-2,3-dihydro-imidazo[4,5-c]pyridin-1-yl]-3-phenyl-propionic acid
2-Methyl-propane-2-sulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide
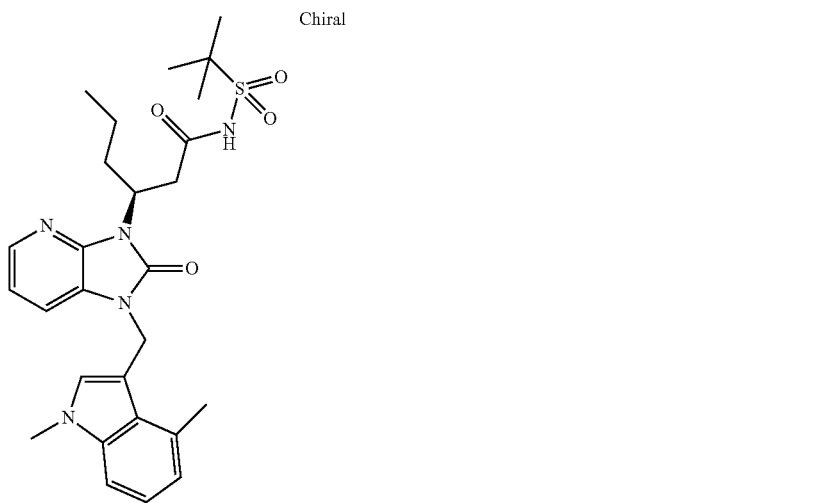 [SMILES: CCC[C@@H](CC(=O)NS(=O)(=O)C(C)(C)C)n1c(=O)n(Cc2cn(C)c3cccc(C)c23)c2cccnc21]
(R)-3-[1-(1,4-Dimethyl-1H-indol-3-ylmethyl)-5-methyl-2-oxo-1,2-dihydro-imidazo[4,5-b]pyridin-3-yl]-3-pyridin-3-yl-propionic acid
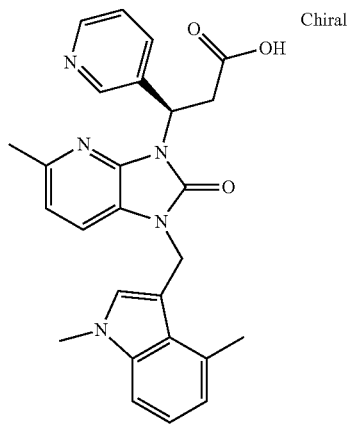 [SMILES: Cc1ccc2c(n1)n([C@H](CC(=O)O)c1cccnc1)c(=O)n2Cc1cn(C)c2cccc(C)c12]

TABLE I-continued

| | | |
|---|---|---|
| 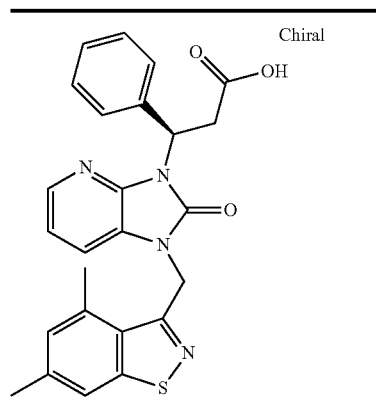 Chiral | | (R)-3-[1-(4,6-Dimethyl-benzo[d]isothiazol-3-ylmethyl)-2-oxo-1,2-dihydro-imidazo[4,5-b]pyridin-3-yl]-3-phenyl-propionic acid |
| 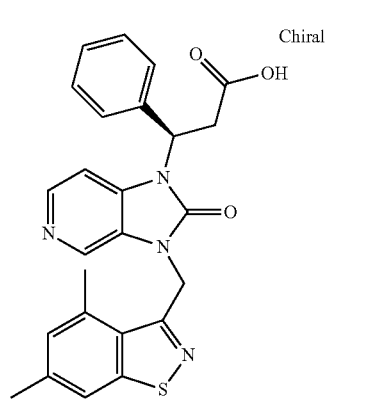 [SMILES: Cc1cc(C)c2c(Cn3c(=O)n([C@H](CC(=O)O)c4ccccc4)c4ccncc43)nsc2c1] Chiral | | (R)-3-[3-(4,6-Dimethyl-benzo[d]isothiazol-3-ylmethyl)-2-oxo-2,3-dihydro-imidazo[4,5-c]pyridin-1-yl]-3-phenyl-propionic acid |
| 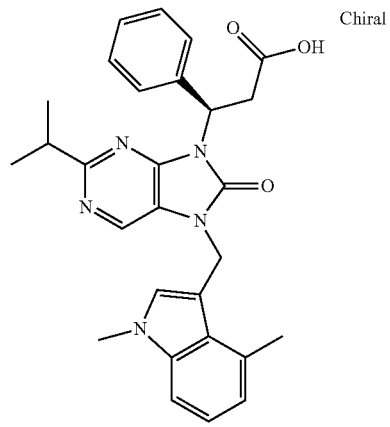 [SMILES: Cc1cccc2c1c(Cn1c(=O)n([C@H](CC(=O)O)c3ccccc3)c3nc(C(C)C)ncc31)cn2C] Chiral | | (R)-3-[7-(1,4-Dimethyl-1H-indol-3-ylmethyl)-2-isopropyl-8-oxo-7,8-dihydro-purin-9-yl]-3-phenyl-propionic acid |
| 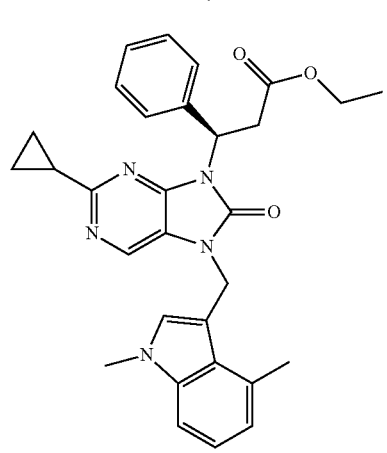 Chiral | | (R)-3-[2-Cyclopropyl-7-(1,4-dimethyl-1H-indol-3-ylmethyl)-8-oxo-7,8-dihydro-purin-9-yl]-3-phenyl-propionic acid ethyl ester |

TABLE I-continued
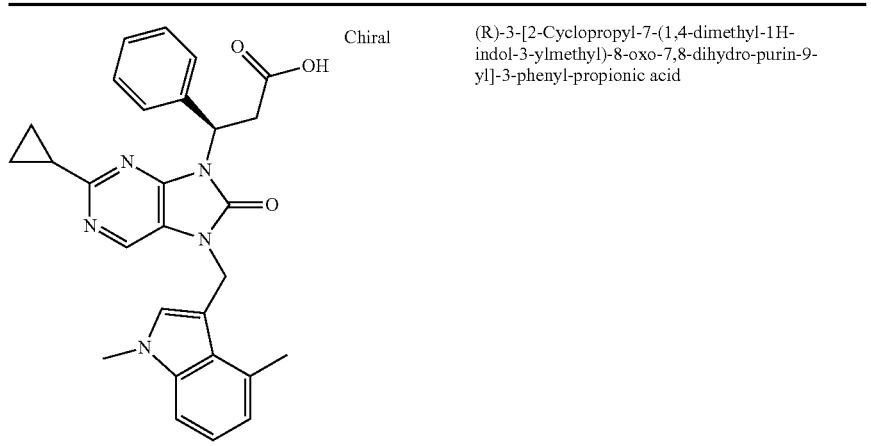
(R)-3-[2-Cyclopropyl-7-(1,4-dimethyl-1H-indol-3-ylmethyl)-8-oxo-7,8-dihydro-purin-9-yl]-3-phenyl-propionic acid
(R)-3-[1-(1,4-Dimethyl-1H-indol-3-ylmethyl)-5-methoxy-2-oxo-1,2-dihydro-imidazo[4,5-b]pyridin-3-yl]-3-phenyl-propionic acid
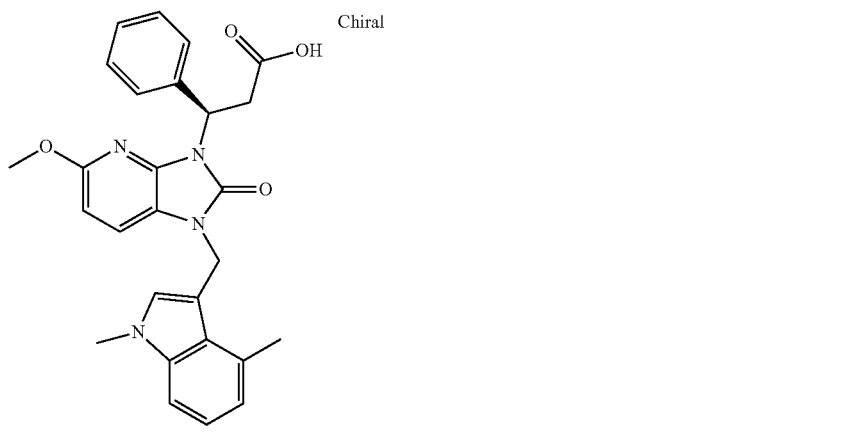 [SMILES: COc1ccc2c(n1)n([C@H](CC(=O)O)c1ccccc1)c(=O)n2Cc1cn(C)c2cccc(C)c12]
(R)-3-[3-(1,4-Dimethyl-1H-indol-3-ylmethyl)-6-methyl-2-oxo-2,3-dihydro-imidazo[4,5-c]pyridin-1-yl]-3-phenyl-propionic acid
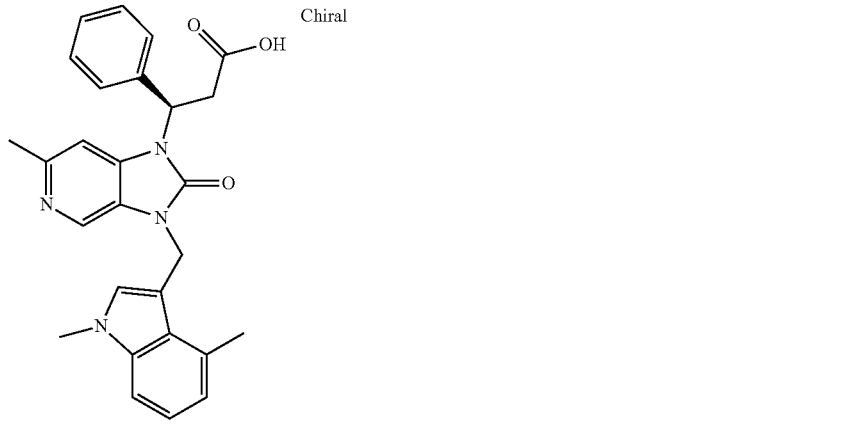 [SMILES: Cc1cc2c(cn1)n(Cc1cn(C)c3cccc(C)c13)c(=O)n2[C@H](CC(=O)O)c1ccccc1]

TABLE I-continued
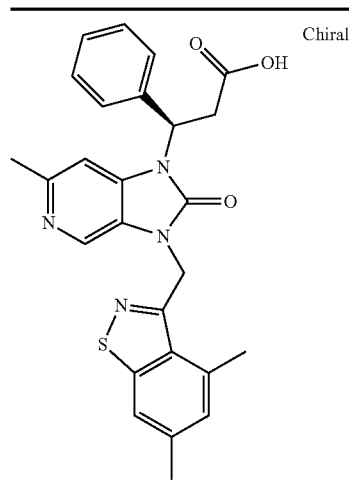
(R)-3-[3-(4,6-Dimethyl-1,2-benzisothiazol-3-ylmethyl)-6-methyl-2-oxo-2,3-dihydro-imidazo[4,5-c]pyridin-1-yl]-3-phenyl-propionic acid
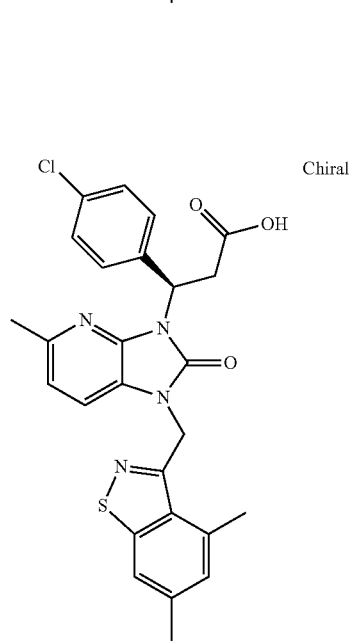
(R)-3-(4-Chloro-phenyl)-3-[1-(4,6-dimethyl-1,2-benzisothiazol-3-ylmethyl)-5-methyl-2-oxo-1,2-dihydro-imidazo[4,5-b]pyridin-3-yl]-propionic acid
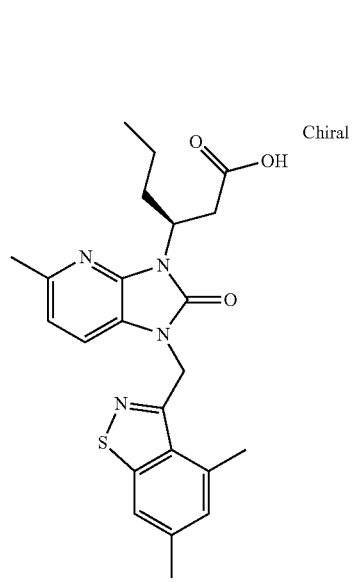 [SMILES: CCC[C@@H](CC(=O)O)n1c(=O)n(Cc2nsc3cc(C)cc(C)c23)c2ccc(C)nc21]
(S)-3-[1-(4,6-Dimethyl-1,2-benzisothiazol-3-ylmethyl)-5-methyl-2-oxo-1,2-dihydro-imidazo[4,5-b]pyridin-3-yl]-hexanoic acid TABLE I-continued

| Structure | Name |
|---|---|
| (chiral structure with 3-chlorophenyl, carboxylic acid, imidazo[4,5-b]pyridinone, and 4,6-dimethylbenzisothiazole) | (R)-3-(3-Chloro-phenyl)-3-[1-(4,6-dimethyl-1,2-benzisothiazol-3-ylmethyl)-5-methyl-2-oxo-1,2-dihydro-imidazo[4,5-b]pyridin-3-yl]-propionic acid |
| (chiral structure with propyl chain, ethyl ester, imidazo[4,5-b]pyridinone, and 4,6-dimethylbenzisothiazole) | (S)-3-[1-(4,6-Dimethyl-benzo[d]isothiazol-3-ylmethyl)-2-oxo-1,2-dihydro-imidazo[4,5-b]pyridin-3-yl]-hexanoic acid ethyl ester, |
| (chiral structure with phenyl, ethyl ester, imidazo[4,5-b]pyridinone, and 1,4-dimethylindole) | (R)-3-[1-(1,4-Dimethyl-1H-indol-3-ylmethyl)-2-oxo-1,2-dihydro-imidazo[4,5-b]pyridin-3-yl]-3-phenyl-propionic acid ethyl ester |

TABLE I-continued
| Structure | Name |
|---|---|
| 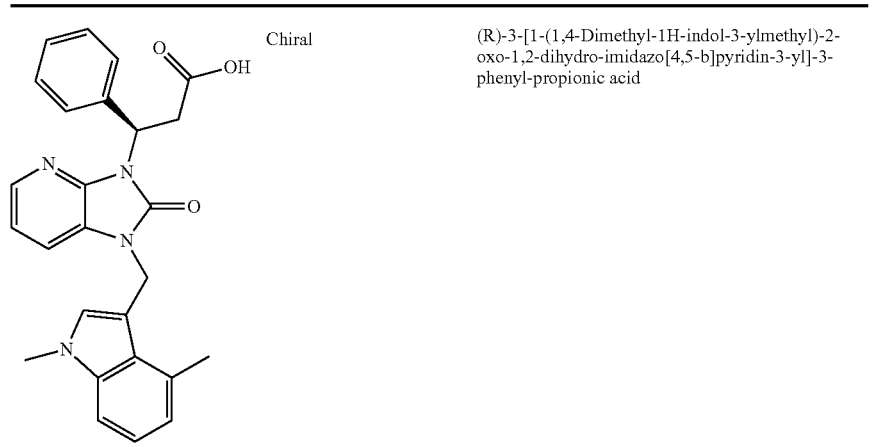 Chiral | (R)-3-[1-(1,4-Dimethyl-1H-indol-3-ylmethyl)-2-oxo-1,2-dihydro-imidazo[4,5-b]pyridin-3-yl]-3-phenyl-propionic acid |
| 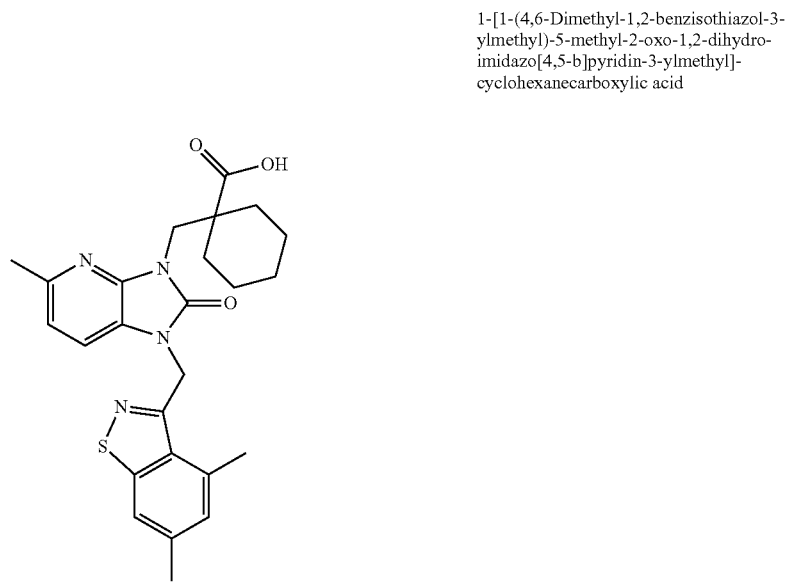 | 1-[1-(4,6-Dimethyl-1,2-benzisothiazol-3-ylmethyl)-5-methyl-2-oxo-1,2-dihydro-imidazo[4,5-b]pyridin-3-ylmethyl]-cyclohexanecarboxylic acid |
| 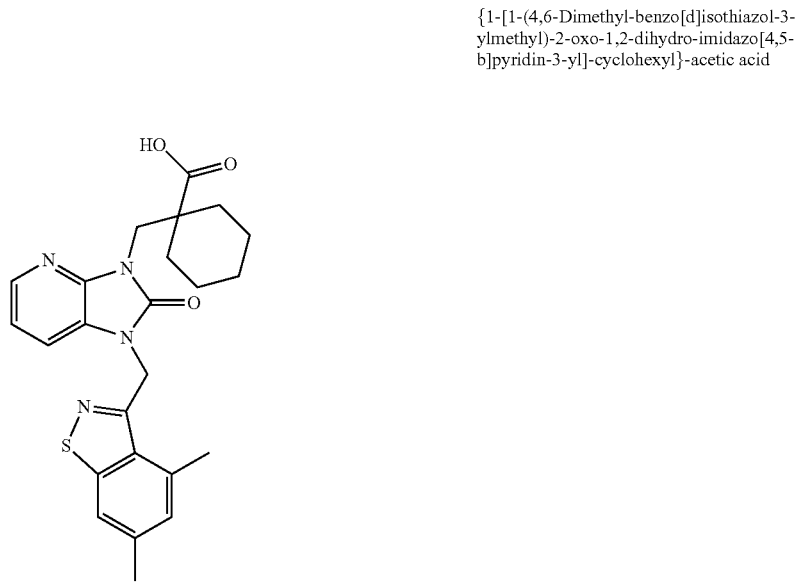 | {1-[1-(4,6-Dimethyl-benzo[d]isothiazol-3-ylmethyl)-2-oxo-1,2-dihydro-imidazo[4,5-b]pyridin-3-yl]-cyclohexyl}-acetic acid |

TABLE I-continued

| Structure | Name |
|---|---|
| (Chiral structure with 4-chlorophenyl) | (R)-3-(4-Chloro-phenyl)-3-[1-(1,4-dimethyl-1H-indol-3-ylmethyl)-5-methyl-2-oxo-1,2-dihydro-imidazo[4,5-b]pyridin-3-yl]-propionic acid |
| (Chiral structure with 3-chlorophenyl) | (R)-3-(3-Chloro-phenyl)-3-[1-(1,4-dimethyl-1H-indol-3-ylmethyl)-5-methyl-2-oxo-1,2-dihydro-imidazo[4,5-b]pyridin-3-yl]-propionic acid |
| (Chiral structure with 4-methoxyphenyl) | (R)-3-[1-(1,4-Dimethyl-1H-indol-3-ylmethyl)-5-methyl-2-oxo-1,2-dihydro-imidazo[4,5-b]pyridin-3-yl]-3-(4-methoxy-phenyl)-propionic acid |

TABLE I-continued
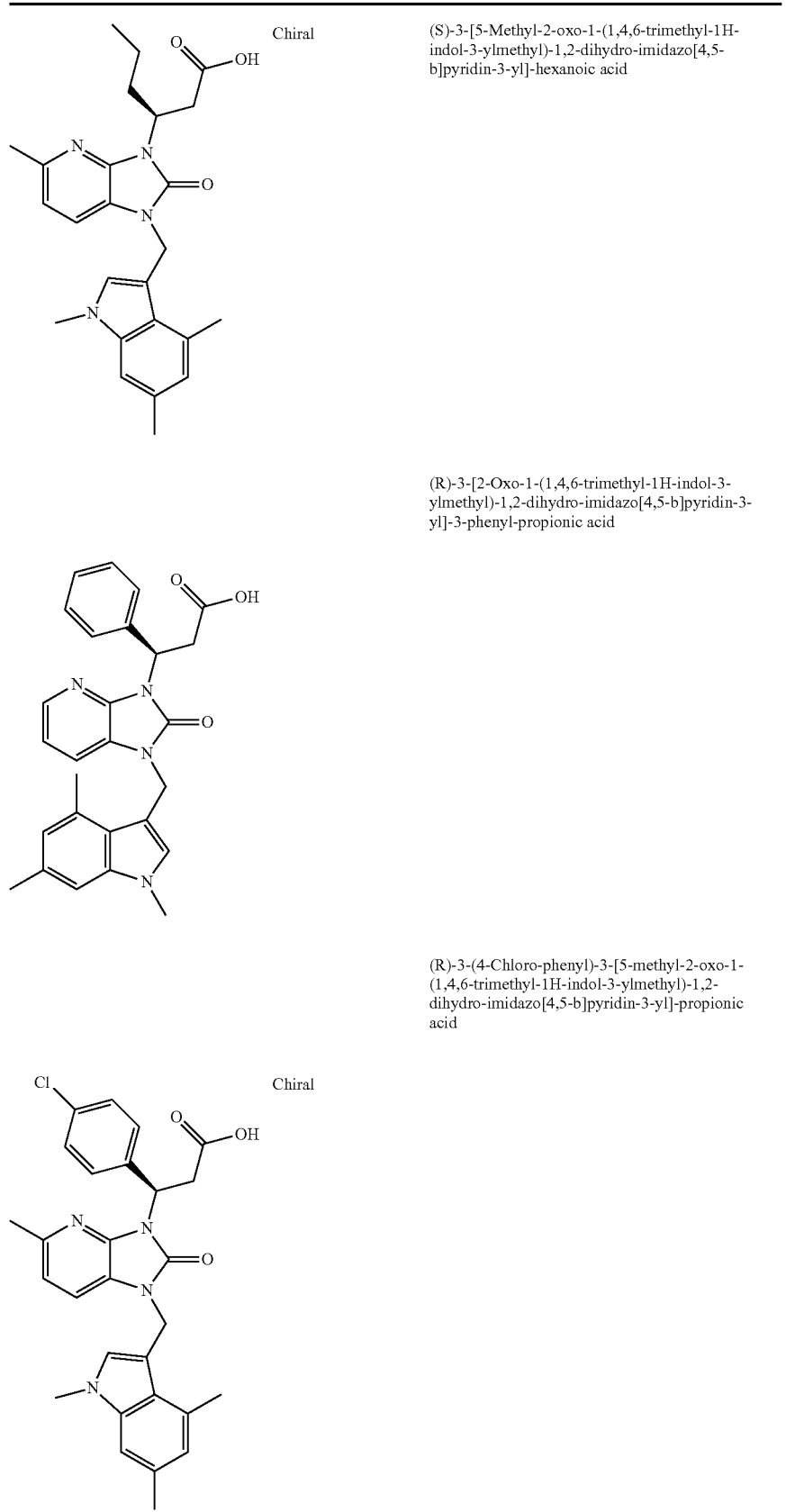
(S)-3-[5-Methyl-2-oxo-1-(1,4,6-trimethyl-1H-indol-3-ylmethyl)-1,2-dihydro-imidazo[4,5-b]pyridin-3-yl]-hexanoic acid
(R)-3-[2-Oxo-1-(1,4,6-trimethyl-1H-indol-3-ylmethyl)-1,2-dihydro-imidazo[4,5-b]pyridin-3-yl]-3-phenyl-propionic acid
(R)-3-(4-Chloro-phenyl)-3-[5-methyl-2-oxo-1-(1,4,6-trimethyl-1H-indol-3-ylmethyl)-1,2-dihydro-imidazo[4,5-b]pyridin-3-yl]-propionic acid

TABLE I-continued
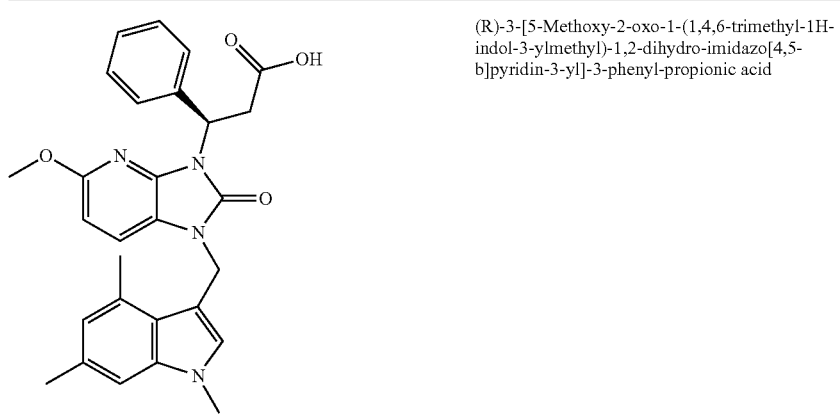
(R)-3-[5-Methoxy-2-oxo-1-(1,4,6-trimethyl-1H-indol-3-ylmethyl)-1,2-dihydro-imidazo[4,5-b]pyridin-3-yl]-3-phenyl-propionic acid
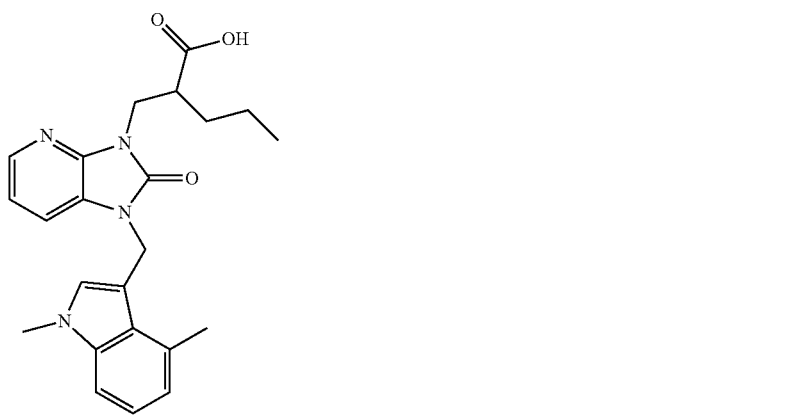 [SMILES: CCCC(Cn1c(=O)n(Cc2cn(C)c3cccc(C)c23)c2cccnc21)C(=O)O]
2-[1-(1,4-Dimethyl-1H-indol-3-ylmethyl)-2-oxo-1,2-dihydro-imidazo[4,5-b]pyridin-3-ylmethyl]-pentanoic acid
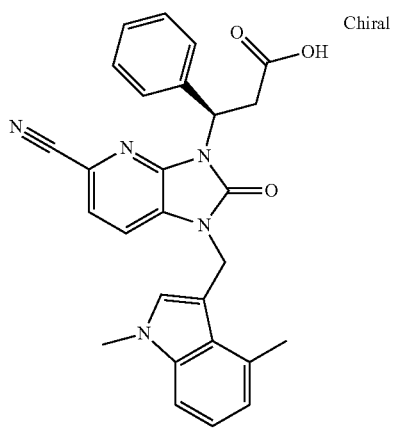 [SMILES: Cc1cccc2c1c(Cn1c(=O)n([C@H](CC(=O)O)c3ccccc3)c3nc(C#N)ccc31)cn2C]
(R)-3-[5-Cyano-1-(1,4-dimethyl-1H-indol-3-ylmethyl)-2-oxo-1,2-dihydro-imidazo[4,5-b]pyridin-3-yl]-3-phenyl-propionic acid TABLE I-continued
| | | |
|---|---|---|
| 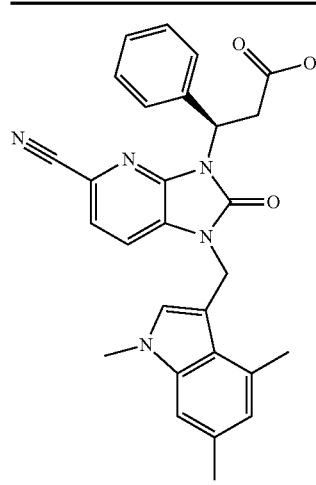 Chiral | | (R)-3-[5-Cyano-2-oxo-1-(1,4,6-timethyl-1H-indol-3-ylmethyl)-1,2-dihydro-imidazo[4,5-b]pyridin-3-yl]-3-phenyl-propionic acid |
| | | (R)-3-[5-Cyano-1-(1,4-dimethyl-1H-indol-3-ylmethyl)-2-oxo-1,2-dihydro-imidazo[4,5-b]pyridin-3-yl]-3-(4-fluoro-phenyl)-propionic acid |
| 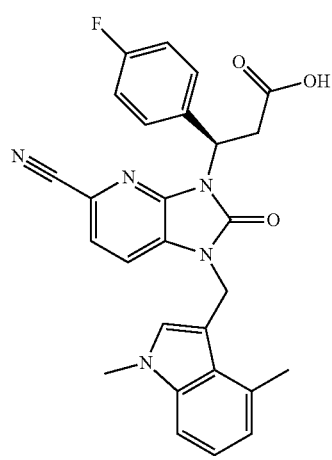 Chiral | | |
| | | (R)-3-[5-Cyano-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid |
| 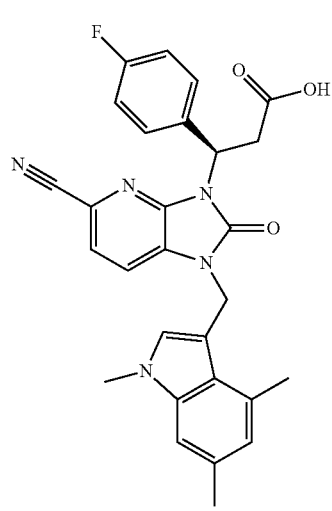 Chiral | | |

TABLE I-continued
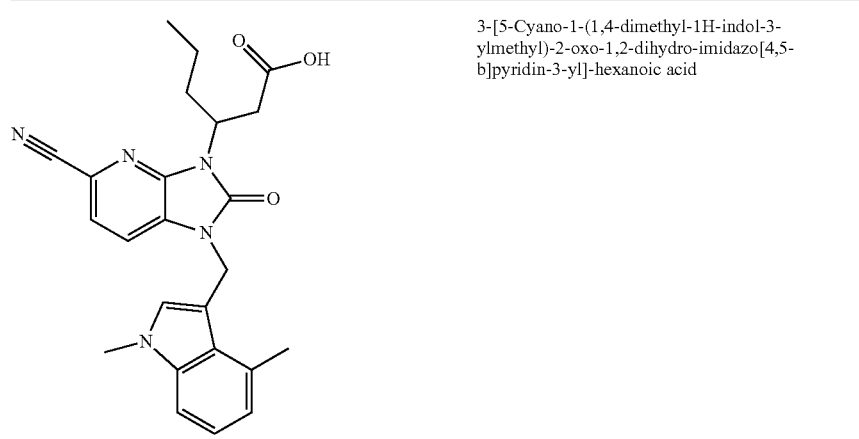
3-[5-Cyano-1-(1,4-dimethyl-1H-indol-3-ylmethyl)-2-oxo-1,2-dihydro-imidazo[4,5-b]pyridin-3-yl]-hexanoic acid
3-[5-Cyano-2-oxo-1-(1,4,6-trimethyl-1H-indol-3-ylmethyl)-1,2-dihydro-imidazo[4,5-b]pyridin-3-yl]-hexanoic acid
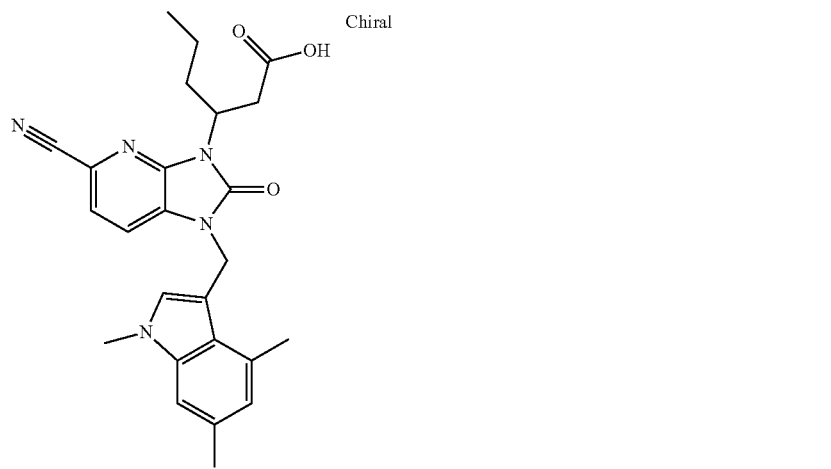 [SMILES: CCCC(CC(=O)O)n1c(=O)n(Cc2cn(C)c3cc(C)cc(C)c23)c2ccc(C#N)nc21]
(R)-3-(4-Chloro-phenyl)-3-[5-cyano-1-(1,4-dimethyl-1H-indol-3-ylmethyl)-2-oxo-1,2-dihydro-imidazo[4,5-b]pyridin-3-yl]-propionic acid
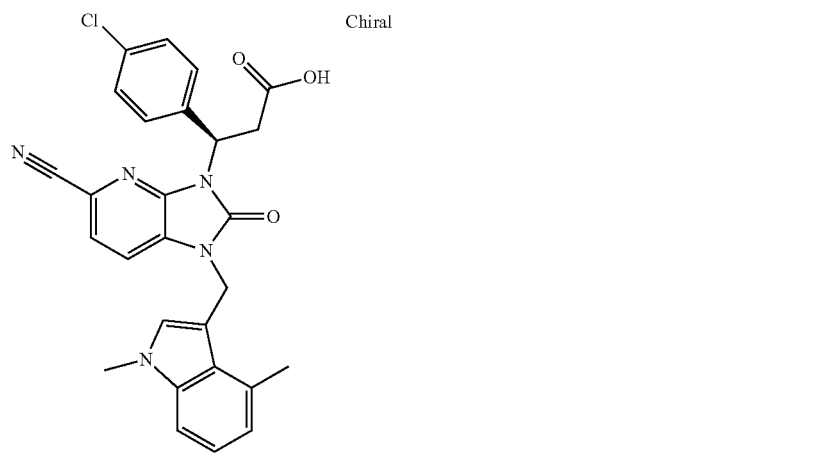 [SMILES: Cc1cccc2c1c(Cn1c(=O)n([C@H](CC(=O)O)c3ccc(Cl)cc3)c3nc(C#N)ccc31)cn2C]

TABLE I-continued

| Structure | Name |
|---|---|
| 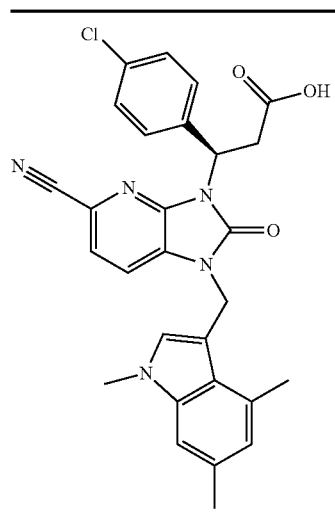 | (R)-3-(4-Chloro-phenyl)-3-[5-cyano-2-oxo-1-(1,4,6-trimethyl-1H-indol-3-ylmethyl)-1,2-dihydro-imidazo[4,5-b]pyridin-3-yl]-propionic acid |
| 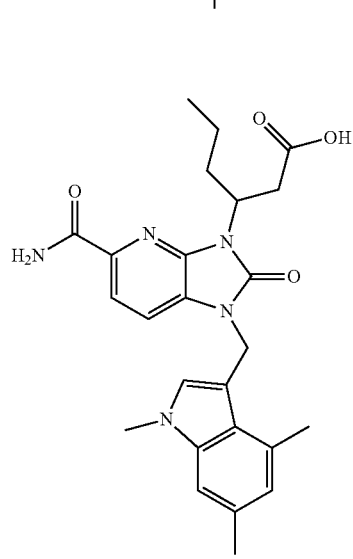 | 3-[5-Carbamoyl-2-oxo-1-(1,4,6-trimethyl-1H-indol-3-ylmethyl)-1,2-dihydro-imidazo[4,5-b]pyridin-3-yl]-hexanoic acid |
| 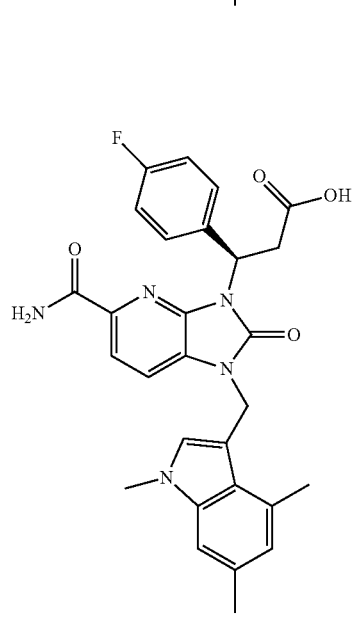 | (R)-3-[5-Carbamoyl-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid | or the pharmaceutically acceptable salts thereof.

The following is Chymase IC50 (nM) data for preferred formula (I) compounds of the invention:

TABLE II

| Chymase IC50 (nM) | |
|---|---|
| (R)-3-(4-Chloro-phenyl)-3-[5-cyano-1-(1,4-dimethyl-1H-indol-3-ylmethyl)-2-oxo-1,2-dihydro-imidazo[4,5-b]pyridin-3-yl]-propionic acid | 0.165 |
| (R)-3-(4-Chloro-phenyl)-3-[5-methyl-2-oxo-1-(1,4,6-trimethyl-1H-indol-3-ylmethyl)-1,2-dihydro-imidazo[4,5-b]pyridin-3-yl]-propionic acid | 0.2 |
| (R)-3-(4-Chloro-phenyl)-3-[5-cyano-2-oxo-1-(1,4,6-trimethyl-1H-indol-3-ylmethyl)-1,2-dihydro-imidazo[4,5-b]pyridin-3-yl]-propionic acid | 0.2 |
| (R)-3-[5-Cyano-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid | 0.23 |
| (R)-3-[5-Cyano-1-(1,4-dimethyl-1H-indol-3-ylmethyl)-2-oxo-1,2-dihydro-imidazo[4,5-b]pyridin-3-yl]-3-(4-fluoro-phenyl)-propionic acid | 0.245 |
| (R)-3-(4-Chloro-phenyl)-3-[1-(1,4-dimethyl-1H-indol-3-ylmethyl)-5-methyl-2-oxo-1,2-dihydro-imidazo[4,5-b]pyridin-3-yl]-propionic acid | 0.255 |
| (R)-3-[5-Carbamoyl-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid | 0.395 |
| (R)-3-[1-(1,4-Dimethyl-1H-indol-3-ylmethyl)-5-methyl-2-oxo-1,2-dihydro-imidazo[4,5-b]pyridin-3-yl]-3-(4-methoxy-phenyl)-propionic acid | 0.455 |
| (R)-3-[5-Cyano-2-oxo-1-(1,4,6-trimethyl-1H-indol-3-ylmethyl)-1,2-dihydro-imidazo[4,5-b]pyridin-3-yl]-3-phenyl-propionic acid | 0.6 |
| (R)-3-[5-Methoxy-2-oxo-1-(1,4,6-trimethyl-1H-indol-3-ylmethyl)-1,2-dihydro-imidazo[4,5-b]pyridin-3-yl]-3-phenyl-propionic acid | 0.605 |
| (R)-3-[2-Oxo-1-(1,4,6-trimethyl-1H-indol-3-ylmethyl)-1,2-dihydro-imidazo[4,5-b]pyridin-3-yl]-3-phenyl-propionic acid | 0.61 |
| (R)-3-(4-Chloro-phenyl)-3-[1-(4,6-dimethyl-1,2-benzisothiazol-3-ylmethyl)-5-methyl-2-oxo-1,2-dihydro-imidazo[4,5-b]pyridin-3-yl]-propionic acid | 0.624 |
| (S)-3-[5-Methyl-2-oxo-1-(1,4,6-trimethyl-1H-indol-3-ylmethyl)-1,2-dihydro-imidazo[4,5-b]pyridin-3-yl]-hexanoic acid | 0.81 |
| 2-Methyl-propane-2-sulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide | 1 |
| 3-[5-Cyano-2-oxo-1-(1,4,6-trimethyl-1H-indol-3-ylmethyl)-1,2-dihydro-imidazo[4,5-b]pyridin-3-yl]-hexanoic acid | 1.065 |
| 1-[1-(4,6-Dimethyl-1,2-benzisothiazol-3-ylmethyl)-5-methyl-2-oxo-1,2-dihydro-imidazo[4,5-b]pyridin-3-ylmethyl]-cyclohexanecarboxylic acid | 1.45 |
| (R)-3-[5-Cyano-1-(1,4-dimethyl-1H-indol-3-ylmethyl)-2-oxo-1,2-dihydro-imidazo[4,5-b]pyridin-3-yl]-3-phenyl-propionic acid | 1.5 |
| 3-[5-Carbamoyl-2-oxo-1-(1,4,6-trimethyl-1H-indol-3-ylmethyl)-1,2-dihydro-imidazo[4,5-b]pyridin-3-yl]-hexanoic acid | 1.93 |
| (R)-3-[1-(1,4-Dimethyl-1H-indol-3-ylmethyl)-5-methoxy-2-oxo-1,2-dihydro-imidazo[4,5-b]pyridin-3-yl]-3-phenyl-propionic acid | 2.05 |
| {1-[1-(4,6-Dimethyl-benzo[d]isothiazol-3-ylmethyl)-2-oxo-1,2-dihydro-imidazo[4,5-b]pyridin-3-yl]-cyclohexyl}-acetic acid | 2.1 |
| 3-[5-Cyano-1-(1,4-dimethyl-1H-indol-3-ylmethyl)-2-oxo-1,2-dihydro-imidazo[4,5-b]pyridin-3-yl]-hexanoic acid | 2.2 |
| (R)-3-[1-(1,4-Dimethyl-1H-indol-3-ylmethyl)-2-oxo-1,2-dihydro-imidazo[4,5-b]pyridin-3-yl]-3-phenyl-propionic acid | 2.21 |
| (R)-3-[1-(1,4-Dimethyl-1H-indol-3-ylmethyl)-5-methyl-2-oxo-1,2-dihydro-imidazo[4,5-b]pyridin-3-yl]-3-phenyl-propionic acid | 2.52 |
| (R)-3-[3-(1,4-Dimethyl-1H-indol-3-ylmethyl)-6-methyl-2-oxo-2,3-dihydro-imidazo[4,5-c]pyridin-1-yl]-3-phenyl-propionic acid | 2.62 |
| 2-[1-(1,4-Dimethyl-1H-indol-3-ylmethyl)-2-oxo-1,2-dihydro-imidazo[4,5-b]pyridin-3-ylmethyl]-pentanoic acid | 3 |
| (S)-3-[1-(4,6-Dimethyl-1,2-benzisothiazol-3-ylmethyl)-5-methyl-2-oxo-1,2-dihydro-imidazo[4,5-b]pyridin-3-yl]-hexanoic acid | 3.4 |
| (S)-3-[1-(1,4-Dimethyl-1H-indol-3-ylmethyl)-6-methyl-2-oxo-1,2-dihydro-imidazo[4,5-b]pyridin-3-yl]-hexanoic acid | 3.46 |
| (R)-3-[3-(1,4-Dimethyl-1H-indol-3-ylmethyl)-2-oxo-2,3-dihydro-imidazo[4,5-c]pyridin-1-yl]-3-phenyl-propionic acid | 3.91 |
| (R)-3-[3-(4,6-Dimethyl-1,2-benzisothiazol-3-ylmethyl)-6-methyl-2-oxo-2,3-dihydro-imidazo[4,5-c]pyridin-1-yl]-3-phenyl-propionic acid | 4 |
| (R)-3-[1-(4,6-Dimethyl-benzo[d]isothiazol-3-ylmethyl)-2-oxo-1,2-dihydro-imidazo[4,5-b]pyridin-3-yl]-3-phenyl-propionic acid | 4.23 |
| (S)-3-[1-(1,4-Dimethyl-1H-indol-3-ylmethyl)-5-methyl-2-oxo-1,2-dihydro-imidazo[4,5-b]pyridin-3-yl]-hexanoic acid | 4.48 |
| (S)-3-[1-(1,4-Dimethyl-1H-indol-3-ylmethyl)-2-oxo-1,2-dihydro-imidazo[4,5-b]pyridin-3-yl]-hexanoic acid | 4.93 |
| (R)-3-[2-Cyclopropyl-7-(1,4-dimethyl-1H-indol-3-ylmethyl)-8-oxo-7,8-dihydro-purin-9-yl]-3-phenyl-propionic acid | 5 |
| (R)-3-(3-Chloro-phenyl)-3-[1-(4,6-dimethyl-1,2-benzisothiazol-3-ylmethyl)-5-methyl-2-oxo-1,2-dihydro-imidazo[4,5-b]pyridin-3-yl]-propionic acid | 6.26 |
| 1-Methyl-1H-imidazole-4-sulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide | 6.71 |
| (R)-3-(3-Chloro-phenyl)-3-[1-(1,4-dimethyl-1H-indol-3-ylmethyl)-5-methyl-2-oxo-1,2-dihydro-imidazo[4,5-b]pyridin-3-yl]-propionic acid | 7.07 |
| Ethanesulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide | 7.48 |
| (S)-3-[3-(1,4-Dimethyl-1H-indol-3-ylmethyl)-2-oxo-2,3-dihydro-imidazo[4,5-b]pyridin-1-yl]-hexanoic acid | 8.86 |
| (R)-3-[1-(1,4-Dimethyl-1H-indol-3-ylmethyl)-5-methyl-2-oxo-1,2-dihydro-imidazo[4,5-b]pyridin-3-yl]-3-pyridin-3-yl-propionic acid | 10.72 |
| (R)-3-[3-(4,6-Dimethyl-benzo[d]isothiazol-3-ylmethyl)-2-oxo-2,3-dihydro-imidazo[4,5-c]pyridin-1-yl]-3-phenyl-propionic acid | 11.2 |
| N-{(S)-3-[1-(1,4-Dimethyl-1H-indol-3-ylmethyl)-2-oxo-1,2-dihydro-imidazo[4,5-b]pyridin-3-yl]-hexanoyl}-methanesulfonamide | 11.83 |
| (R)-3-[7-(1,4-Dimethyl-1H-indol-3-ylmethyl)-2-isopropyl-8-oxo-7,8-dihydro-purin-9-yl]-3-phenyl-propionic acid | 12.6 |
| (S)-3-[3-(1,4-Dimethyl-1H-indol-3-ylmethyl)-2-oxo-2,3-dihydro-imidazo[4,5-c]pyridin-1-yl]-hexanoic acid | 18.95 | or the pharmaceutically acceptable salts thereof.

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures, and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, $C_{1-4}$alkoxy includes the organic radical $C_{1-4}$alkyl with a terminal oxygen, such as methoxy, ethoxy, propoxy, butoxy.

All organic radicals: alkyl, alkenyl and alkynyl groups, or such groups which are incorporated in other radicals such as acyl and alkoxy, shall be understood as being branched or unbranched where structurally possible and unless otherwise specified, and may be partially or fully halogenated.

The term "lower" referred to above and hereinafter in connection with organic radicals or compounds respectively defines such as branched or unbranched with up to and including 7, preferably up to and including 4 and advantageously one or two carbon atoms.

A cyclic group shall be understood to mean carbocycle, heterocycle or heteroaryl, each may be partially or fully halogenated.

An acyl group is a radical defined as —C(O)—R, where R is an organic radical or a cyclic group. Acyl represents, for example, carbocyclic or heterocyclic aroyl, cycloalkylcarbonyl, (oxa or thia)-cycloalkylcarbonyl, lower alkanoyl, (lower alkoxy, hydroxy or acyloxy)-lower alkanoyl, (mono- or dicarbocyclic or heterocyclic)-(lower alkanoyl or lower alkoxy-, hydroxy- or acyloxy-substituted lower alkanoyl), or biaroyl.

Carbocycles include hydrocarbon rings containing from three to fourteen carbon atoms. These carbocycles may be either aromatic either aromatic or non-aromatic ring systems. The non-aromatic ring systems may be mono- or polyunsaturated, monocyclic, bicyclic or tricyclic and may be bridged. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, benzyl, indanyl, indenyl, benzocyclobutanyl, dihydronaphthyl, tetrahydronaphthyl, naphthyl, decahydronaphthyl, benzocycloheptanyl, adamantyl, norbornyl, fluorene, and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or non-aromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N, O and S. Unless otherwise stated, such heteroaryls include aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzopyrrolyl, benzothiazolyl, benzisothiazol, benzothienyl, quinolinyl, quinazolinyl, naphthyridinyl, indazolyl, triazolyl, tetrazolyl.

The term "heteroatom" as used herein shall be understood to mean atoms other than carbon such as oxygen, nitrogen, sulfur and phosphorous.

As used herein, "nitrogen" and "sulfur" include any oxidized form of nitrogen and sulfur and the quaternized form of any basic nitrogen. All heteroatoms in open chain or cyclic radicals include all oxidized forms.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative and/or is partially or fully halogenated. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds described herein are either commercially available or can be made by methods and any necessary intermediates well known in the art.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

GENERAL SYNTHETIC METHODS

The invention also provides processes for making compounds of Formula (I). In all Schemes, unless specified otherwise, $R_1$, $R_2$, $R_3$, $R_8$, $R_9$, $R_{10}$, n, A, X and Y in the formulas below shall have the meaning of $R_1$, $R_2$, $R_3$, $R_8$, $R_9$, $R_{10}$, n, A, X and Y in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The appropriately substituted starting materials and intermediates used in the preparation of compounds of the invention are either commercially available or readily prepared by methods known in the literature to those skilled in the art, and are illustrated in the synthetic examples below.

Further modification of the initial product of Formula (I) by methods known in the art and illustrated in the Examples below, may be used to prepare additional compounds of this invention.

Compounds of Formula (I) may be synthesized by methods outlined in schemes 1-4.

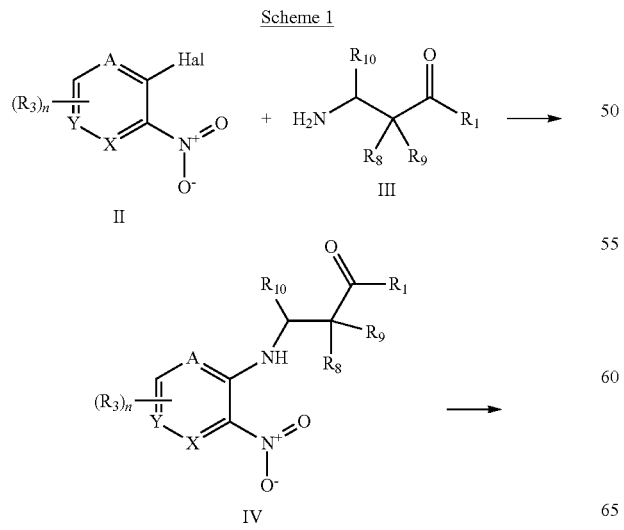

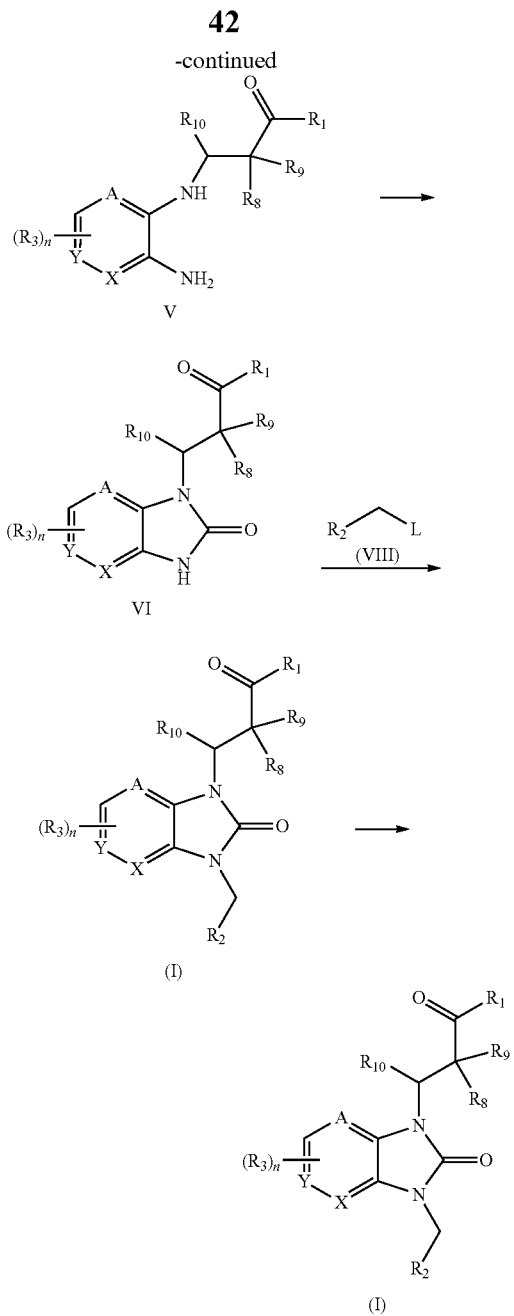

As outlined in scheme 1, reaction of a nitro compound of formula (II), wherein Hal=Cl, Br or I, with an amine of formula (III), in a suitable solvent, in the presence of a suitable base, provides a nitro compound of formula (IV). Reducing the nitro group of the compound of formula (IV) under standard conditions, provides the corresponding amine of formula (V). Cyclization of the intermediate of formula (V) using a reagent such as N,N'-carbonyldiimidazole (CDI), in a suitable solvent, provides an imidazo compound of formula (VI). Reaction of the intermediate of formula (VI) with an alkylating agent of formula (VII), wherein L is a leaving group, under standard conditions, provides a compound of Formula (I). Further modification of this compound of Formula (I) using standard procedures known to one skilled in the art, provides additional compounds of Formula (I).

Compounds of Formula (I) may also be made by the method shown in scheme 2.

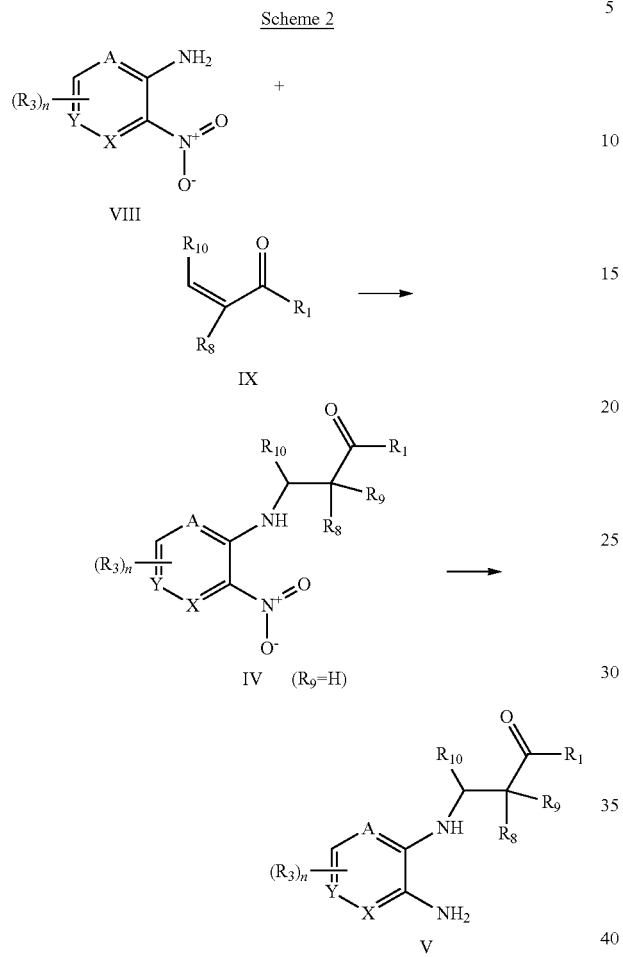

As illustrated in scheme 2, reaction of a nitro amine compound of formula (VIII) with an alkene of formula (IX), in a suitable solvent, in the presence of a suitable base, provides an intermediate of formula (IV). Reduction of the nitro group of intermediate of formula (IV) under standard conditions, provides the corresponding amine of formula (V). The intermediate of formula (V) may then be converted to a compound of Formula (I) by the steps outlined in scheme 1.

Compounds of Formula (I) wherein A and Y=N and X=CH, may be synthesized by the method shown in scheme 3

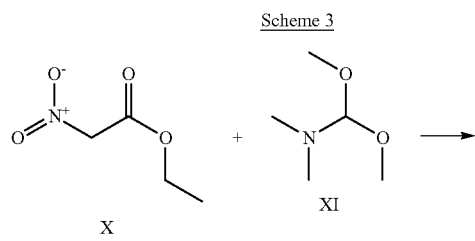

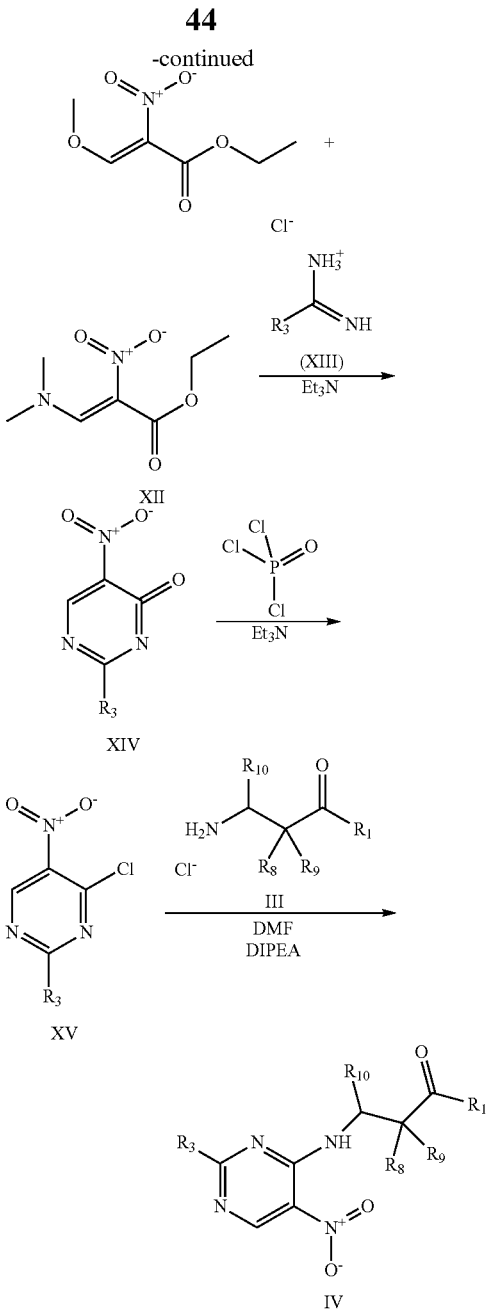

As shown in scheme 3, reaction of ethyl nitro acetate (X) with dimethyl formamide dimethyl acetal (XI) provides a mixture of alkenes (XII). Reaction of this mixture of alkenes (XII) with an amidine of formula (XIII), in the presence of a suitable base, provides a pyrimidinone of formula (XIV). Reaction of the pyrimidinone of formula (XIV) with phosphorus oxy chloride, in a suitable solvent, in the presence of a suitable base, provides an intermediate of formula (XV). Reaction of the intermediate (XV) with an amine of formula (III), in a suitable solvent, in the presence of a suitable base, provides a compound of formula (IV). The intermediate of formula (IV) may be converted to a compound of Formula (I) by steps outlined in scheme 1.

Further modification of the initial product of Formula (I) by methods known in the art and illustrated in the Examples below, may be used to prepare additional compounds of this invention.

45

The intermediate $R_2$—$CH_2$-L, when $R_2$=4,6-dimethyl-benzoisothiazole and L=Br, may be prepared by the reaction sequence shown in scheme 4.

Scheme 4

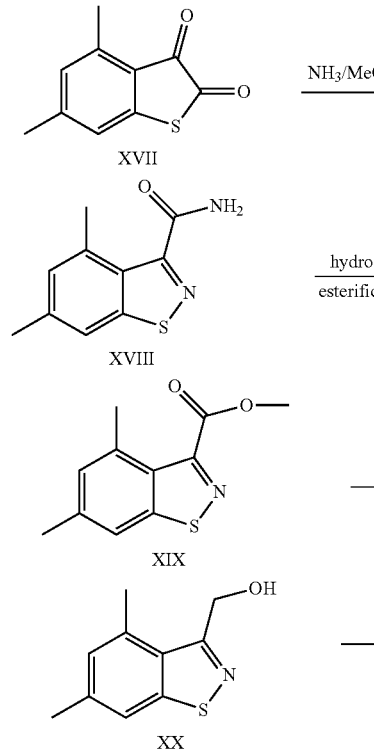

As outlined in scheme 4, reaction of dimethyl benzene thiol (XVI) with oxalyl chloride, in the presence of aluminum chloride, provides a dione (XVII). Reaction of the dione with ammonia in methanol provides a benzoisothiazole of formula (XVIII). Hydrolysis of the amide group of compound (XVIII) followed by esterification, under standard reaction conditions, provides a compound of formula (XIX). Reduction of the ester group in compound (XIX) using a reagent such as lithium aluminum hydride, provides the primary alcohol of formula (XX). The alcohol (XX) may be converted to the desired intermediate (VII) by reaction with carbon tetrabromide.

46

EXPERIMENTAL

Example 1

(S)-3-[1-(1,4-Dimethyl-1H-indol-3-ylmethyl)-5-methyl-2-oxo-1,2-dihydro-imidazo[4,5-b]pyridin-3-yl]-hexanoic acid

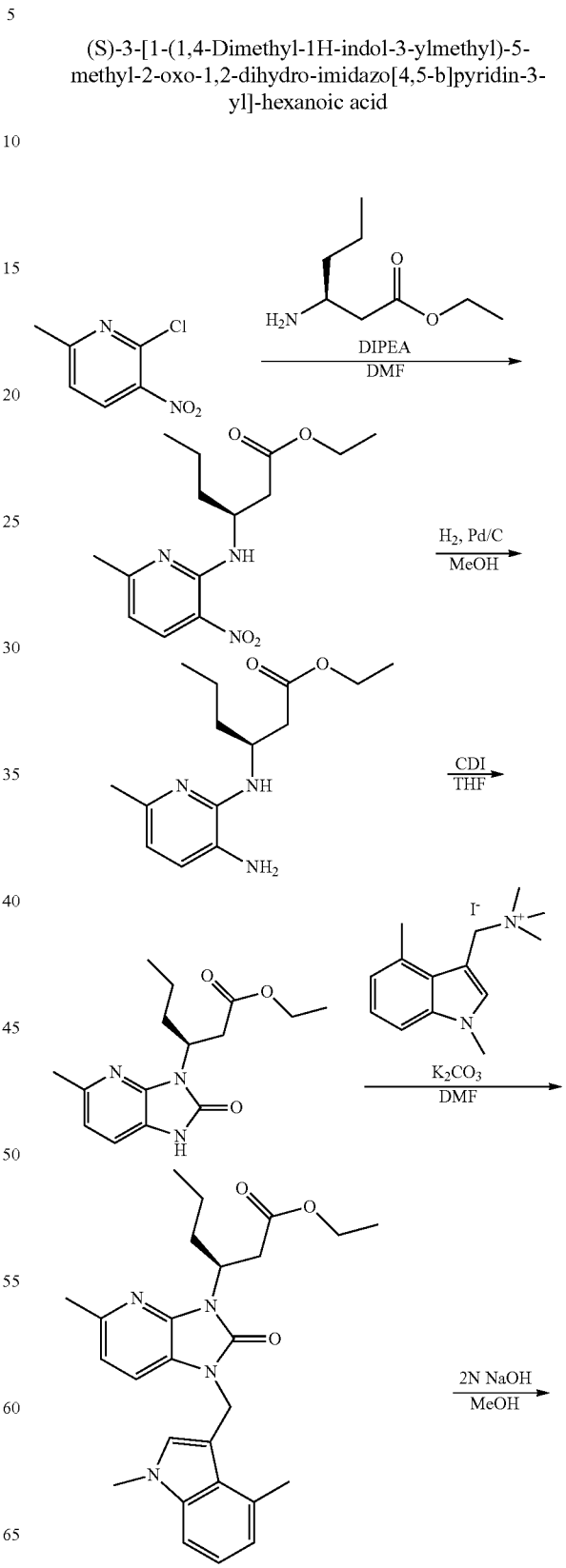

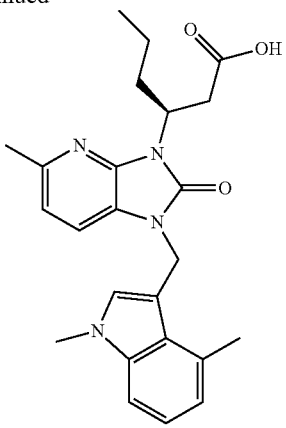

(S)-3-(6-Methyl-3-nitro-pyridin-2-ylamino)-hexanoic acid ethyl ester

To a solution of 2-chloro-3-nitro-6-picoline (500 mg, 2.99 mmol) in DMF (3 mL) were added the (S)-3-amino-hexanoic acid ethyl ester (554 mg, 3.48 mmol) and diisopropylethyl amine (DIPEA) (1.0 mL, 5.80 mmol). The reaction mixture was stirred at room temperature for 48 hours. The reaction mixture was then diluted with ethyl acetate and washed with water (×4). The organic phase was then dried over $Na_2SO_4$ and concentrated. The resulting residue was purified by preparative TLC using hexane and ethyl acetate (4:1) as an eluent to afford 358 mg (42%) of the title compound as orange oil. LCMS, $M^++1$, m/z: 296.65.

(S)-3-(3-Amino-6-methyl-pyridin-2-ylamino)-hexanoic acid ethyl ester

To a slurry of (S)-3-(6-methyl-3-nitro-pyridin-2-ylamino)-hexanoic acid ethyl ester (358 mg, 1.21 mmol) in MeOH (10 mL) was added Pd/C (150 mg). The reaction mixture was de-gassed using house vacuum and saturated with $H_2$. The reaction mixture was stirred at room temperature for 3 hours. The mixture was filtered through a celite and the filtrate was concentrated to afford 350 mg (100%) of the desired product as pale yellow oil. The resulting residue was used for the next reaction without further purification.

(S)-3-(5-Methyl-2-oxo-1,2-dihydro-imidazo[4,5-b]pyridin-3-yl)-hexanoic acid ethyl ester To a solution of (S)-3-(3-amino-6-methyl-pyridin-2-ylamino)-hexanoic acid ethyl ester (350 mg, 1.32 mmol) in THF (10 mL) was added N,N'-carbonyldiimidazole (CDI) (321 mg, 2.0 mmol). The reaction mixture was stirred at room temperature for 5 hours. The reaction mixture was concentrated. The resulting residue was purified by silica gel preparative TLC using 95:5 $CH_2Cl_2$:MeOH as an eluent to afford 247 mg (64%) of the title compound as a light brown oily residue. LCMS, $M^++1$, m/z: 292.59.

(S)-3-[1-(1,4-Dimethyl-1H-indol-3-ylmethyl)-5-methyl-2-oxo-1,2-dihydro-imidazo[4,5-b]pyridin-3-yl]-hexanoic acid ethyl ester To a solution of (S)-3-(5-methyl-2-oxo-1,2-dihydro-imidazo[4,5-b]pyridin-3-yl)-hexanoic acid ethyl ester (247 mg, 0.85 mmol) in DMF (5 mL) were added $K_2CO_3$ (234 mg, 1.7 mmol) and (1,4-dimethyl-1H-indol-3-ylmethyl)-trimethylammonium iodide (438 mg, 1.27 mmol). The reaction mixture was heated to 60° C. for 48 hours. The reaction mixture was diluted with ethyl acetate and washed with water (×4). The organic phase was dried over $Na_2SO_4$ and concentrated. The resulting residue was purified by silica gel preparative TLC using 98:2 $CH_2Cl_2$:MeOH as an eluent to afford 170 mg (45%) of the title compound. LCMS, $M^++1$, m/z: 449.47.

(S)-3-[1-(1,4-Dimethyl-1H-indol-3-ylmethyl)-5-methyl-2-oxo-1,2-dihydro-imidazo[4,5-b]pyridin-3-yl]-hexanoic acid To a solution of (S)-3-[1-(1,4-dimethyl-1H-indol-3-ylmethyl)-5-methyl-2-oxo-1,2-dihydro-imidazo[4,5-b]pyridin-3-yl]-hexanoic acid ethyl ester (170 mg, 0.38 mmol) in MeOH (10 mL) was added 2N NaOH (2 mL). The reaction mixture was stirred at room temperature for 3 hours. When the reaction was complete, the reaction mixture was treated with 1N HCl and extracted with $CH_2Cl_2$ twice. The organic phase was dried over $Na_2SO_4$ and concentrated. The resulting residue was purified by silica gel preparative TLC using 10:1 $CH_2Cl_2$:MeOH as an eluent to afford 135 mg (85%) of the product as a pale yellow solid. LCMS, $M^++1$, m/z: 421.41.

The following compound was prepared in the same manner using 2-Chloro-5-methyl-3-nitro-pyridine.

(S)-3-[1-(1,4-Dimethyl-1H-indol-3-ylmethyl)-6-methyl-2-oxo-1,2-dihydro-imidazo[4,5-b]pyridin-3-yl]-hexanoic acid. LCMS, $M^++1$, m/z: 421.58.

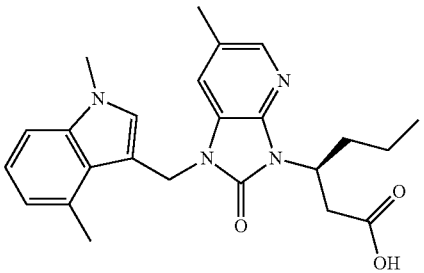 [SMILES: CCC[C@@H](CC(=O)O)n1c(=O)n(Cc2cn(C)c3cccc(C)c23)c2cc(C)cnc21]

The following compound was prepared in the same manner using 3-Bromomethyl-4,6-dimethyl-1,2-benzisothiazole.

(S)-3-[1-(4,6-Dimethyl-1,2-benzisothiazol-3-ylmethyl)-5-methyl-2-oxo-1,2-dihydro-imidazo[4,5-b]pyridin-3-yl]-hexanoic acid. LCMS, $M^++1$, m/z: 440.08.

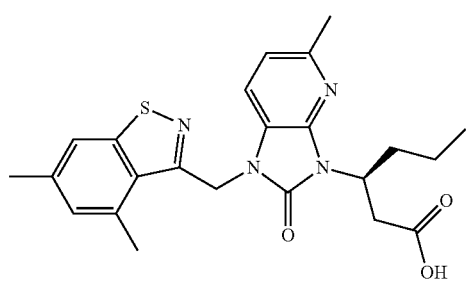 [SMILES: CCC[C@@H](CC(=O)O)n1c(=O)n(Cc2nsc3cc(C)cc(C)c23)c2ccc(C)nc21]

The following compound was prepared in the same manner using Trimethyl-(1,4,6-trimethyl-1H-indol-3-ylmethyl)-ammonium iodide.

(S)-3-[5-Methyl-2-oxo-1-(1,4,6-trimethyl-1H-indol-3-ylmethyl)-1,2-dihydro-imidazo[4,5-b]pyridin-3-yl]-hexanoic acid. LCMS, M$^+$+1, m/z: 435.76.

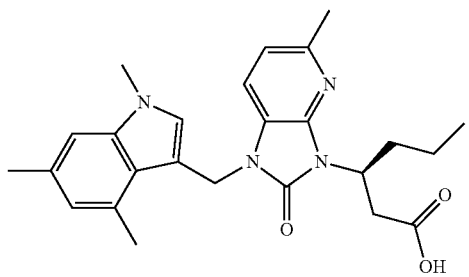 [SMILES: CCC[C@@H](CC(=O)O)n1c(=O)n(Cc2cn(C)c3cc(C)cc(C)c23)c2ccc(C)nc21]

The following compound was prepared in the same manner using 2-Chloro-3-nitropyridine.

(S)-3-[1-(1,4-Dimethyl-1H-indol-3-ylmethyl)-2-oxo-1,2-dihydro-imidazo[4,5-b]pyridin-3-yl]-hexanoic acid ethyl ester. LCMS, M$^+$+1, m/z: 434.53

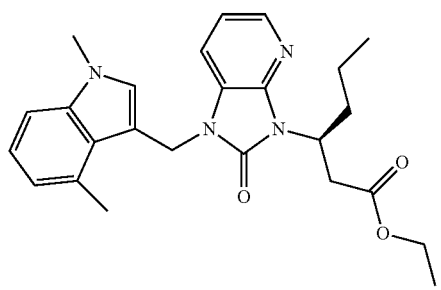 [SMILES: CCC[C@@H](CC(=O)OCC)n1c(=O)n(Cc2cn(C)c3cccc(C)c23)c2cccnc21]

The following compound was prepared in the same manner using 3-Chloro-2-nitropyridine.

(S)-3-[3-(1,4-Dimethyl-1H-indol-3-ylmethyl)-2-oxo-2,3-dihydro-imidazo[4,5-b]pyridin-1-yl]-hexanoic acid ethyl ester. LCMS, M$^+$+1, m/z: 434.53

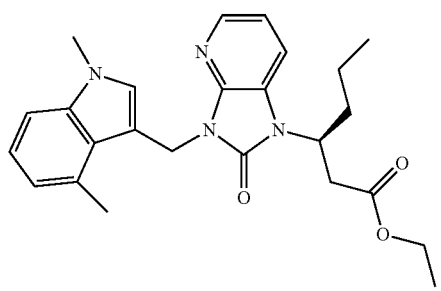 [SMILES: CCC[C@@H](CC(=O)OCC)n1c(=O)n(Cc2cn(C)c3cccc(C)c23)c2ncccc21]

The following compound was prepared in the same manner using 2-Chloro-3-nitropyridine.

(S)-3-[1-(1,4-Dimethyl-1H-indol-3-ylmethyl)-2-oxo-1,2-dihydro-imidazo[4,5-b]pyridin-3-yl]-hexanoic acid. LCMS, M$^+$+1, m/z: 406.48

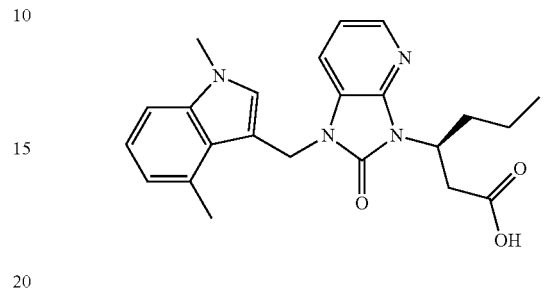

The following compound was prepared in the same manner using 3-Chloro-2-nitropyridine (S)-3-[3-(1,4-Dimethyl-1H-indol-3-ylmethyl)-2-oxo-2,3-dihydro-imidazo[4,5-b]pyridin-1-yl]-hexanoic acid. LCMS, M$^+$+1, m/z: 406.48

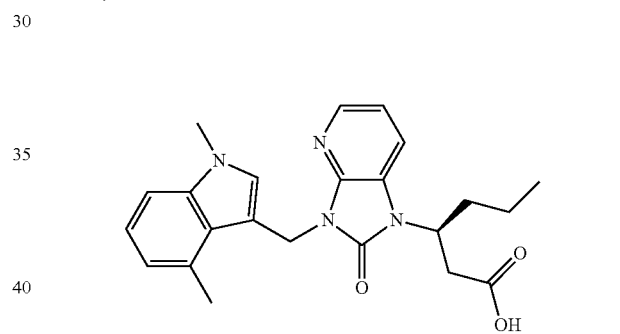

The following compound was prepared in the same manner using 4-Chloro-3-nitro-pyridine.

(S)-3-[3-(1,4-Dimethyl-1H-indol-3-ylmethyl)-2-oxo-2,3-dihydro-imidazo[4,5-c]pyridin-1-yl]-hexanoic acid. LCMS, M$^+$+1, m/z: 406.48

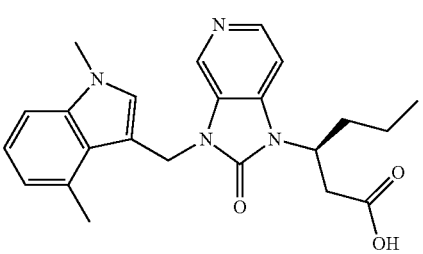 [SMILES: CCC[C@@H](CC(=O)O)n1c(=O)n(Cc2cn(C)c3cccc(C)c23)c2cnccc21]

The following compound was prepared in the same manner using 2-Chloro-3-nitropyridine.

(S)-3-[1-(4,6-Dimethyl-benzo[d]isothiazol-3-ylmethyl)-2-oxo-1,2-dihydro-imidazo[4,5-b]pyridin-3-yl]-hexanoic acid ethyl ester. LCMS, M$^+$+1, m/z: 452.57

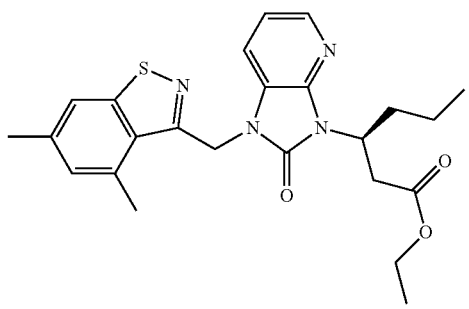 [SMILES: CCC[C@@H](CC(=O)OCC)n1c(=O)n(Cc2nsc3cc(C)cc(C)c23)c2cccnc21]

Example 2

(R)-3-[1-(1,4-Dimethyl-1H-indol-3-ylmethyl)-5-methyl-2-oxo-1,2-dihydro-imidazo[4,5-b]pyridin-3-yl]-3-phenyl-propionic acid

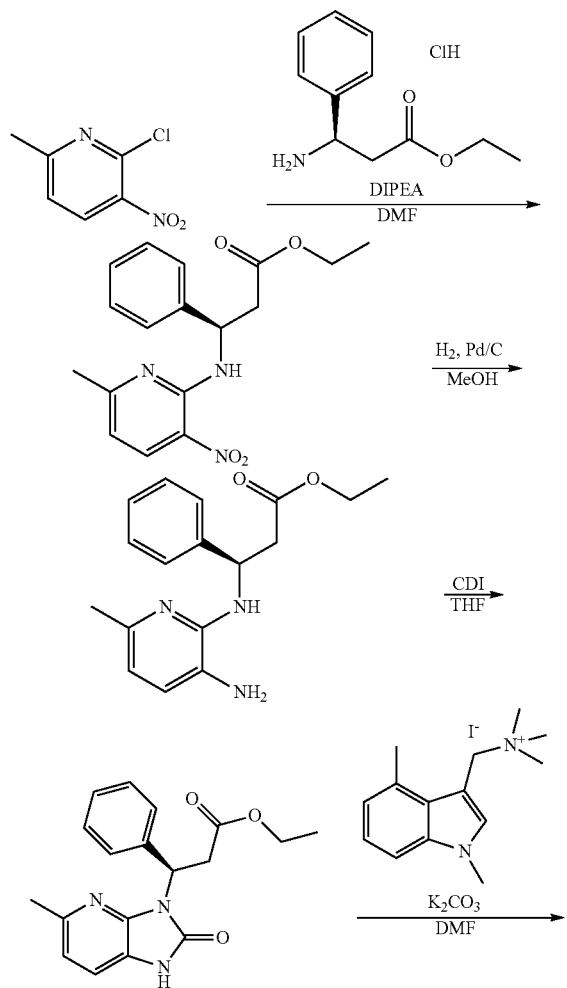

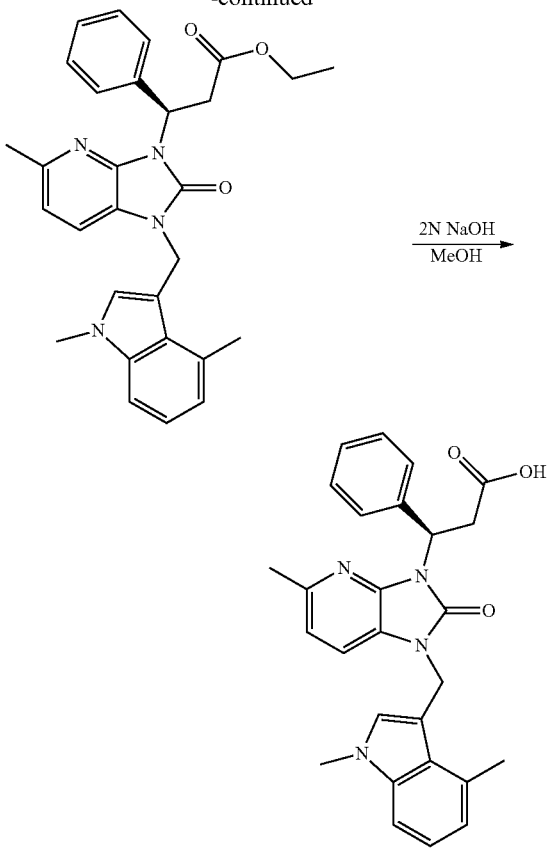

(R)-3-(6-Methyl-3-nitro-pyridin-2-ylamino)-3-phenyl-propionic acid ethyl ester

To a solution of 2-chloro-3-nitro-6-picoline (200 mg, 1.16 mmol) in DMF (3 mL) were added (R)-3-amino-3-phenyl-propanoic acid ethyl ester hydrochloride (319 mg, 1.39 mmol) and DIPEA (0.5 mL, 2.90 mmol). The reaction mixture was stirred at 70° C. for 12 hours. The reaction mixture was then diluted with ethyl acetate and washed with water (×4). The organic phase was then dried over Na$_2$SO$_4$ and concentrated to afford 398 mg (100%) of the title compound as orange oil. The resulting residue was used for the next reaction without further purification. LCMS, M$^+$+1, m/z: 330.29.

(R)-3-(3-Amino-6-methyl-pyridin-2-ylamino)-3-phenyl-propionic acid ethyl ester

To a solution of (R)-3-(6-methyl-3-nitro-pyridin-2-ylamino)-3-phenyl-propionic acid ethyl ester (398 mg, 1.21 mmol) in MeOH (10 mL) was added slurry of Pd/C (150 mg) in MeOH (2 mL). The reaction mixture was degassed using house vacuum. The flask was saturated with H$_2$ and stirred under H$_2$ balloon for 2 hours. When the reaction was completed, the mixture was filtered through a pad of celite and the filtrate was concentrated to afford 390 mg (100%) of the oily residue. The resulting residue was used for the next reaction without further purification. LCMS, M$^+$+1, m/z: 300.15.

(R)-3-(5-Methyl-2-oxo-1,2-dihydro-imidazo[4,5-b]pyridin-3-yl)-3-phenyl-propionic acid ethyl ester To a solution of (R)-3-(3-amino-6-methyl-pyridin-2-ylamino)-3-phenyl-propionic acid ethyl ester (390 mg, 1.30 mmol) in THF (10 mL) was added CDI (317 mg, 1.95 mmol). The reaction mixture was stirred at room temperature for 2 hours and then heated to 60° C. for another 2 hours. The reaction mixture was diluted with ethyl acetate and washed with water. The organic phase was dried over Na₂SO₄ and concentrated. The resulting residue was purified by silica gel prep TLC using 95:5 CH₂Cl₂:MeOH as an eluent to afford 250 mg (59%) of the title compound as a light brown foamy residue. LCMS, M⁺+1, m/z: 326.43

(R)-3-[1-(1,4-Dimethyl-1H-indol-3-ylmethyl)-5-methyl-2-oxo-1,2-dihydro-imidazo[4,5-b]pyridin-3-yl]-3-phenyl-propionic acid ethyl ester To a solution of (R)-3-(5-methyl-2-oxo-1,2-dihydro-imidazo[4,5-b]pyridin-3-yl)-3-phenyl-propionic acid ethyl ester (250 mg, 0.77 mmol) in DMF (5 mL) were added K₂CO₃ (212 mg, 1.54 mmol) and (1,4-dimethyl-1H-indol-3-ylmethyl)-trimethyl-ammonium iodide (397 mg, 1.15 mmol). The reaction mixture was heated to 60° C. for 48 hours. The reaction mixture was then diluted with ethyl acetate and washed with water (×4). The organic phase was dried over Na₂SO₄ and concentrated. The resulting residue was purified by silica gel preparative TLC using 98:2 CH₂Cl₂:MeOH as an eluent to afford 200 mg (54%) of the title compound.

(R)-3-[1-(1,4-Dimethyl-1H-indol-3-ylmethyl)-5-methyl-2-oxo-1,2-dihydro-imidazo[4,5-b]pyridin-3-yl]-3-phenyl-propionic acid To a solution of (R)-3-[1-(1,4-dimethyl-1H-indol-3-ylmethyl)-5-methyl-2-oxo-1,2-dihydro-imidazo[4,5-b]pyridin-3-yl]-3-phenyl-propionic acid ethyl ester (200 mg, 0.41 mmol) in MeOH (5 mL) was added 2N NaOH (2 mL). The reaction mixture was stirred at room temperature for 2 hours. The reaction mixture was then treated with 1N HCl and extracted with CH₂Cl₂ twice. The combined organic phase was dried over Na₂SO₄ and concentrated. The resulting residue was purified by silica gel preparative TLC using 95:5 CH₂Cl₂:MeOH as an eluent to afford 144 mg (76%) of the title compound as off-white solid. LCMS, M⁺+1, m/z: 455.00.

The following compound was prepared in the same manner using (R)-3-Amino-3-pyridin-3-yl-propionic acid ethyl ester.

(R)-3-[1-(1,4-Dimethyl-1H-indol-3-ylmethyl)-5-methyl-2-oxo-1,2-dihydro-imidazo[4,5-b]pyridin-3-yl]-3-pyridin-3-yl-propionic acid. LCMS, M⁺+1, m/z: 456.81.

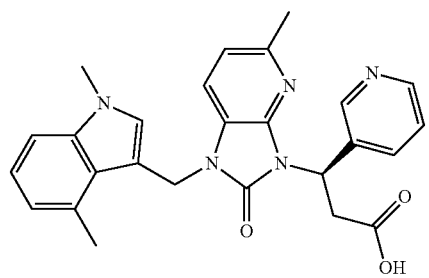 [SMILES: Cc1ccc2c(n1)n([C@H](CC(=O)O)c1cccnc1)c(=O)n2Cc1cn(C)c2cccc(C)c12]

The following compound was prepared in the same manner using 4-Chloro-3-nitro-pyridine.

(R)-3-[3-(1,4-Dimethyl-1H-indol-3-ylmethyl)-2-oxo-2,3-dihydro-imidazo[4,5-c]pyridin-1-yl]-3-phenyl-propionic acid. LCMS, M⁺+1, m/z: 441.57.

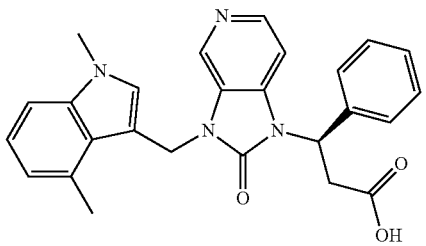 [SMILES: Cc1cccc2c1c(Cn1c(=O)n([C@H](CC(=O)O)c3ccccc3)c3ccncc31)cn2C]

The following compound was prepared in the same manner using 2-Chloro-6-methoxy-3-nitro-pyridine.

(R)-3-[1-(1,4-Dimethyl-1H-indol-3-ylmethyl)-5-methoxy-2-oxo-1,2-dihydro-imidazo[4,5-b]pyridin-3-yl]-3-phenyl-propionic acid. LCMS, M⁺+1, m/z: 471.43.

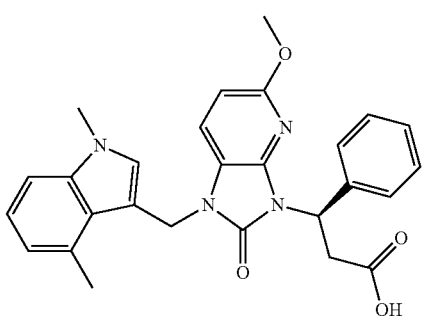 [SMILES: COc1ccc2c(n1)n([C@H](CC(=O)O)c1ccccc1)c(=O)n2Cc1cn(C)c2cccc(C)c12]

The following compound was prepared in the same manner using (R)-3-Amino-3-(4-chloro-phenyl)-propionic acid ethyl ester and 3-Bromomethyl-4,6-dimethyl-1,2-benzisothiazole.

(R)-3-(4-Chloro-phenyl)-3-[1-(4,6-dimethyl-1,2-benzisothiazol-3-ylmethyl)-5-methyl-2-oxo-1,2-dihydro-imidazo[4,5-b]pyridin-3-yl]-propionic acid. LCMS, M⁺+1, m/z: 507.66.

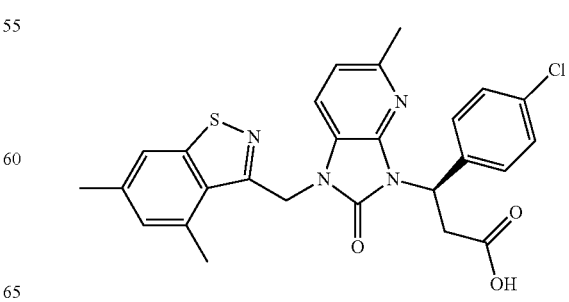

The following compound was prepared in the same manner using (R)-3-Amino-3-(3-chloro-phenyl)-propionic acid ethyl ester and 3-Bromomethyl-4,6-dimethyl-1,2-benzisothiazole.

(R)-3-(3-Chloro-phenyl)-3-[1-(4,6-dimethyl-1,2-benzisothiazol-3-ylmethyl)-5-methyl-2-oxo-1,2-dihydro-imidazo[4,5-b]pyridin-3-yl]-propionic acid. LCMS, M$^+$+1, m/z: 507.62.

The following compound was prepared in the same manner using (R)-3-Amino-3-(4-methoxy-phenyl)-propionic acid ethyl ester and (1,4-Dimethyl-1H-indol-3-ylmethyl)-trimethyl-ammonium iodide.

(R)-3-[1-(1,4-Dimethyl-1H-indol-3-ylmethyl)-5-methyl-2-oxo-1,2-dihydro-imidazo[4,5-b]pyridin-3-yl]-3-(4-methoxy-phenyl)-propionic acid. LCMS, M$^+$+1, m/z: 485.37.

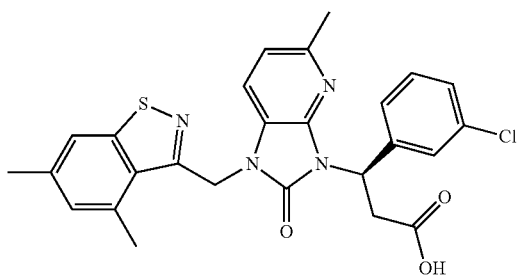 [SMILES: Cc1cc(C)c2c(Cn3c(=O)n([C@H](CC(=O)O)c4cccc(Cl)c4)c4nc(C)ccc43)nsc2c1]

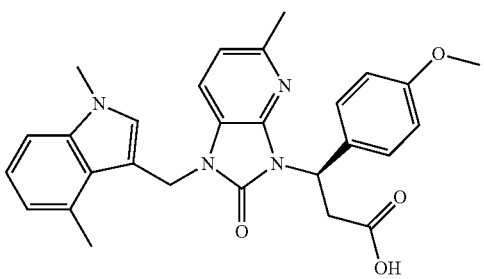

The following compound was prepared in the same manner using (R)-3-Amino-3-(4-chloro-phenyl)-propionic acid ethyl ester and (1,4-Dimethyl-1H-indol-3-ylmethyl)-trimethyl-ammonium iodide.

(R)-3-(4-Chloro-phenyl)-3-[1-(1,4-dimethyl-1H-indol-3-ylmethyl)-5-methyl-2-oxo-1,2-dihydro-imidazo[4,5-b]pyridin-3-yl]-propionic acid. LCMS, M$^+$+1, m/z: 489.72.

The following compound was prepared in the same manner using (R)-3-Amino-3-(4-chloro-phenyl)-propionic acid ethyl ester and Trimethyl-(1,4,6-trimethyl-1H-indol-3-ylmethyl)-ammonium iodide.

(R)-3-(4-Chloro-phenyl)-3-[5-methyl-2-oxo-1-(1,4,6-trimethyl-1H-indol-3-ylmethyl)-1,2-dihydro-imidazo[4,5-b]pyridin-3-yl]-propionic acid. LCMS, M$^+$+1, m/z: 503.78.

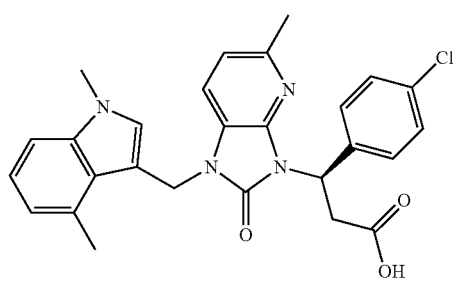 [SMILES: Cc1ccc2c(n1)n([C@H](CC(=O)O)c1ccc(Cl)cc1)c(=O)n2Cc1cn(C)c2cccc(C)c12]

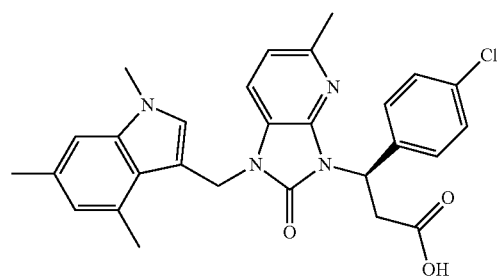

The following compound was prepared in the same manner using (R)-3-Amino-3-(3-chloro-phenyl)-propionic acid ethyl ester and (1,4-Dimethyl-1H-indol-3-ylmethyl)-trimethyl-ammonium iodide.

(R)-3-(3-Chloro-phenyl)-3-[1-(1,4-dimethyl-1H-indol-3-ylmethyl)-5-methyl-2-oxo-1,2-dihydro-imidazo[4,5-b]pyridin-3-yl]-propionic acid. LCMS, M$^+$+1, m/z: 489.69.

The following compound was prepared in the same manner using 1-Aminomethyl-cyclohexanecarboxylic acid methyl ester and 3-Bromomethyl-4,6-dimethyl-1,2-benzisothiazole.

1-[1-(4,6-Dimethyl-1,2-benzisothiazol-3-ylmethyl)-5-methyl-2-oxo-1,2-dihydro-imidazo[4,5-b]pyridin-3-ylmethyl]-cyclohexanecarboxylic acid. LCMS, M$^+$+1, m/z: 466.05.

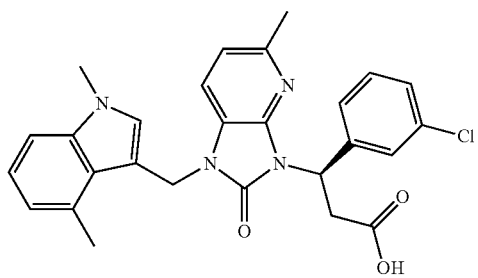 [SMILES: Cc1ccc2c(n1)n([C@H](CC(=O)O)c1cccc(Cl)c1)c(=O)n2Cc1cn(C)c2cccc(C)c12]

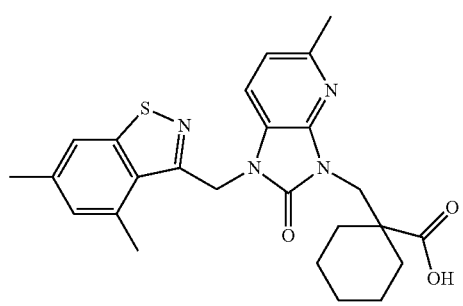 [SMILES: Cc1cc(C)c2c(Cn3c(=O)n(CC4(C(=O)O)CCCCC4)c4nc(C)ccc43)nsc2c1]

The following compound was prepared in the same manner using 2-Chloro-3-nitropyridine.

(R)-3-[1-(1,4-Dimethyl-1H-indol-3-ylmethyl)-2-oxo-1,2-dihydro-imidazo[4,5-b]pyridin-3-yl]-3-phenyl-propionic acid ethyl ester. LCMS, M$^+$+1, m/z: 468.55

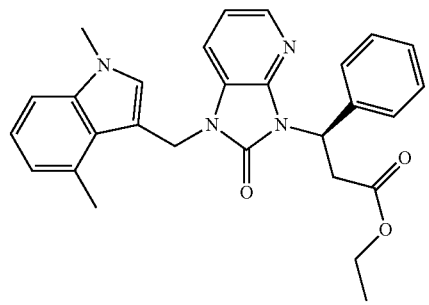 [SMILES: CCOC(=O)C[C@H](c1ccccc1)n1c(=O)n(Cc2cn(C)c3cccc(C)c23)c2cccnc21]

The following compound was prepared in the same manner using 2-Chloro-3-nitropyridine.

(R)-3-[1-(1,4-Dimethyl-1H-indol-3-ylmethyl)-2-oxo-1,2-dihydro-imidazo[4,5-b]pyridin-3-yl]-3-phenyl-propionic acid. LCMS, M$^+$+1, m/z: 440.50

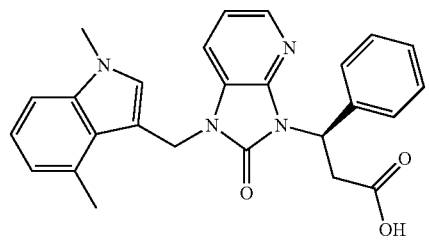 [SMILES: Cc1cccc2c1c(Cn1c(=O)n([C@H](CC(=O)O)c3ccccc3)c3ncccc31)cn2C]

The following compound was prepared in the same manner using 1-Aminomethyl-cyclohexanecarboxylic acid methyl ester and 3-Bromomethyl-4,6-dimethyl-1,2-benzisothiazole.

{1-[1-(4,6-Dimethyl-benzo[d]isothiazol-3-ylmethyl)-2-oxo-1,2-dihydro-imidazo[4,5-b]pyridin-3-yl]-cyclohexyl}-acetic acid. LCMS, M$^+$+1, m/z: 450.55

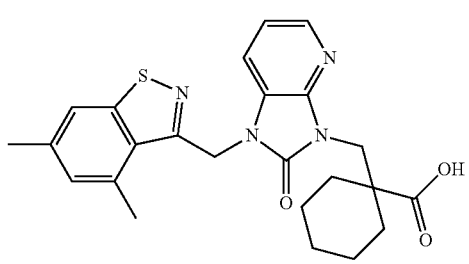 [SMILES: Cc1cc(C)c2c(Cn3c(=O)n(CC4(C(=O)O)CCCCC4)c4ncccc43)nsc2c1]

Example 3

(R)-3-[3-(1,4-Dimethyl-1H-indol-3-ylmethyl)-6-methyl-2-oxo-2,3-dihydro-imidazo[4,5-c]pyridin-1-yl]-3-phenyl-propionic acid

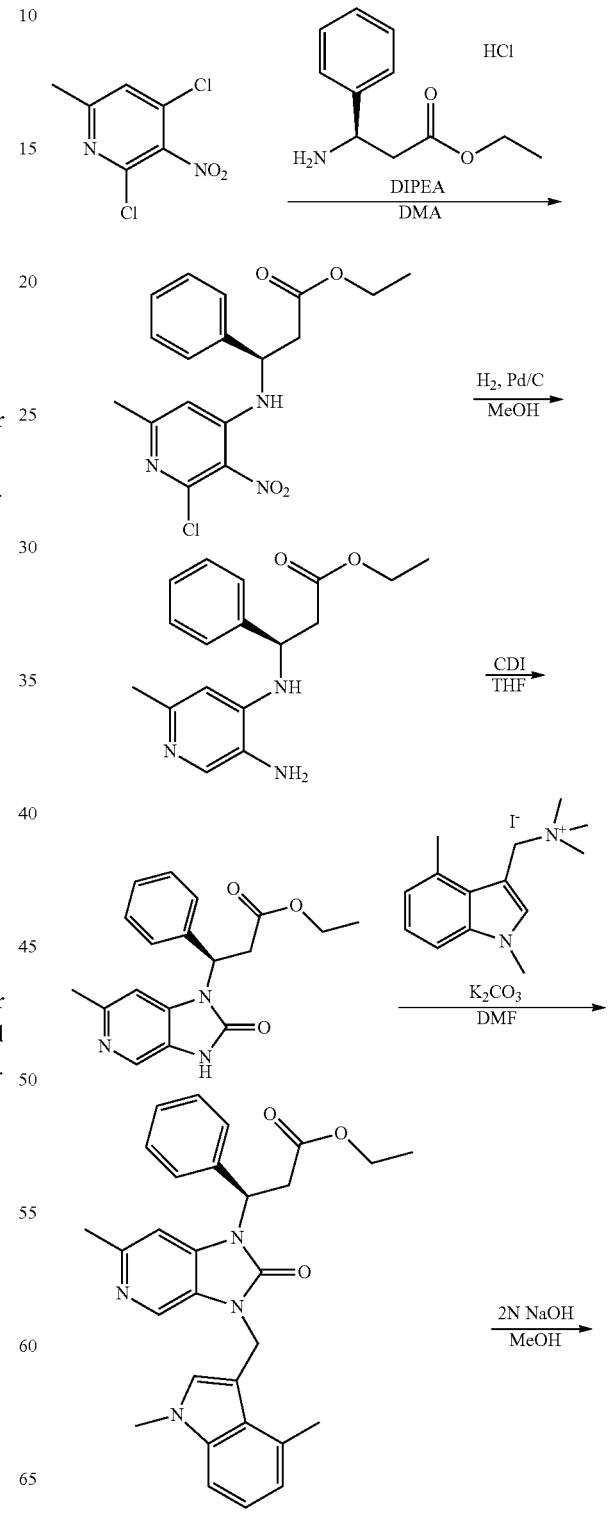

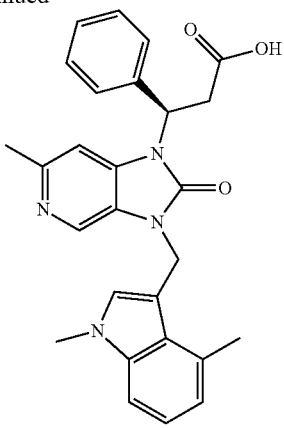

(R)-3-(2-Chloro-6-methyl-3-nitro-pyridin-4-ylamino)-3-phenyl-propionic acid ethyl ester To a solution of 2,4-dichloro-6-methyl-3-nitropyridine (900 mg, 4.35 mmol) in DMA (8 mL) were added (R)-3-amino-3-phenylpropionic acid ethyl ester HCl (799 mg, 3.48 mmol) and DIPEA (1.6 mL, 8.70 mmol). The reaction mixture was stirred at room temperature for 12 hours. The reaction was then diluted with ethyl acetate and washed with water twice. The organic phase was dried over $Na_2SO_4$ and concentrated to give yellow oil. The resulting oily residue was purified by silica gel preparative TLC using 99:1 $CH_2Cl_2$:MeOH as an eluent to afford 650 mg (51%) of the title compound as a light orange oil. LCMS, $M^++1$, m/z: 364.15.

(R)-3-(5-Amino-2-methyl-pyridin-4-ylamino)-3-phenyl-propionic acid ethyl ester To a solution of (R)-3-(2-chloro-6-methyl-3-nitro-pyridin-4-ylamino)-3-phenyl-propionic acid ethyl ester (650 mg, 1.79 mmol) in MeOH (20 ml) was added slurry of Pd/C (500 mg) in MeOH (2 mL). The reaction mixture was degassed using house vacuum. The flask was saturated with $H_2$ and stirred under a $H_2$ balloon for 3 hours. When the reaction was complete, the mixture was filtered through a pad of celite and the filtrate was concentrated to afford 590 mg (100%) of the title compound. The resulting light brown oily residue was used for the next reaction without further purification. LCMS, $M^++1$, m/z: 300.92.

(R)-3-(6-Methyl-2-oxo-2,3-dihydro-imidazo[4,5-c]pyridin-1-yl)-3-phenyl-propionic acid ethyl ester To a solution of (R)-3-(5-amino-2-methyl-pyridin-4-ylamino)-3-phenyl-propionic acid ethyl ester (594 mg, 1.98 mmol) in THF (20 mL) was added CDI (483 mg, 2.98 mmol). The reaction mixture was stirred at room temperature for 20 hours. The reaction mixture was diluted with ethyl acetate and washed with water. The organic phase was dried over $Na_2SO_4$ and concentrated. The resulting residue was purified by silica gel prep TLC using 95:5 $CH_2Cl_2$:MeOH as an eluent to afford 484 mg (75%) of the title compound as light brown solid. LCMS, $M^++1$, m/z: 326.85.

(R)-3-[3-(1,4-Dimethyl-1H-indol-3-ylmethyl)-6-methyl-2-oxo-2,3-dihydro-imidazo[4,5-c]pyridin-1-yl]-3-phenyl-propionic acid ethyl ester To a solution of (R)-3-(6-methyl-2-oxo-2,3-dihydro-imidazo[4,5-c]pyridin-1-yl)-3-phenyl-propionic acid ethyl ester (80 mg, 0.25 mmol) in DMF (3 mL) were added $K_2CO_3$ (41 mg, 0.30 mmol) and (1,4-dimethyl-1H-indol-3-ylmethyl)-trimethyl-ammonium iodide (102 mg, 0.30 mmol). The reaction mixture was heated to 60° C. for 48 hours. The reaction mixture was diluted with ethyl acetate and washed with water (×4). The organic phase was dried over $Na_2SO_4$ and concentrated. The resulting residue was purified by silica gel prep TLC using 98:2 $CH_2Cl_2$:MeOH as an eluent to afford 80 mg (67%) of the title compound. LCMS, $M^++1$, m/z: 484.10.

(R)-3-[3-(1,4-Dimethyl-1H-indol-3-ylmethyl)-6-methyl-2-oxo-2,3-dihydro-imidazo[4,5-c]pyridin-1-yl]-3-phenyl-propionic acid To a solution of (R)-3-[3-(1,4-dimethyl-1H-indol-3-ylmethyl)-6-methyl-2-oxo-2,3-dihydro-imidazo[4,5-c]pyridin-1-yl]-3-phenyl-propionic acid ethyl ester (80 mg, 0.17 mmol) in MeOH (5 mL) was added 2N NaOH (2 mL). The reaction mixture was stirred at room temperature for 2 hours. The reaction was then treated with 0.5N citric acid solution. The reaction mixture was extracted with $CH_2Cl_2$ twice. The organic phase was dried over $Na_2SO_4$ and concentrated. The resulting residue was purified by silica gel preparative TLC using 10:5 $CH_2Cl_2$:MeOH as an eluent to afford 67 mg (89%) of the title compound as a white floppy solid. LCMS, $M^++1$, m/z: 456.15.

The following compound was prepared in the same manner using 3-Bromomethyl-4,6-dimethyl-1,2-benzisothiazole.

(R)-3-[3-(4,6-Dimethyl-1,2-benzisothiazol-3-ylmethyl)-6-methyl-2-oxo-2,3-dihydro-imidazo[4,5-c]pyridin-1-yl]-3-phenyl-propionic acid. LCMS, $M^++1$, m/z: 474.10.

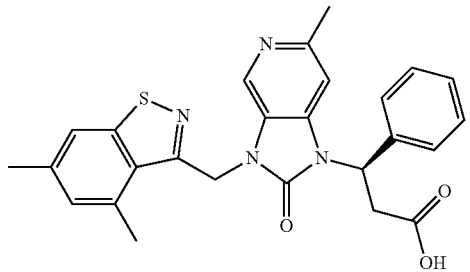 [SMILES: Cc1cc(C)c2c(Cn3c(=O)n([C@H](CC(=O)O)c4ccccc4)c4cc(C)ncc43)nsc2c1]

Example 4

(R)-3-[3-(4,6-Dimethyl-benzo[d]isothiazol-3-ylmethyl)-2-oxo-2,3-dihydro-imidazo[4,5-c]pyridin-1-yl]-3-phenyl-propionic acid

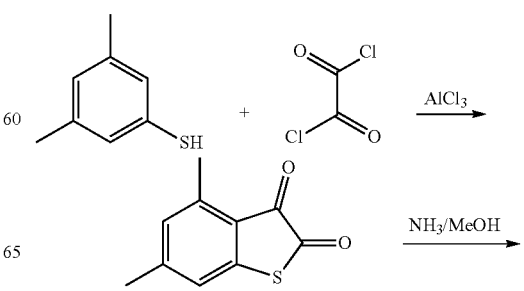

-continued

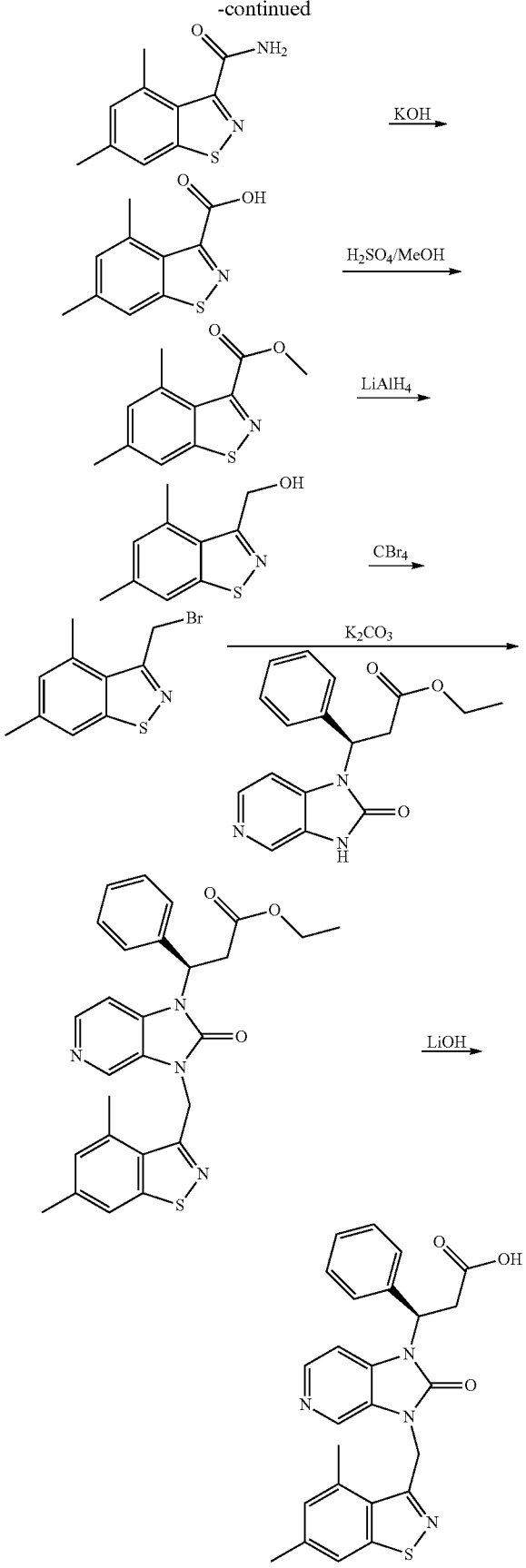

4,6-Dimethyl-benzo[b]thiophene-2,3-dione

To a solution of aluminum chloride (AlCl$_3$) (0.4 g, 3.6 mmol) in CH$_2$Cl$_2$ (4 mL) at −20° C. under nitrogen were added 3,5-dimethylbenzenethiol (1 g, 7.2 mmol) and oxalyl chloride (0.6 mL, 7.2 mmol) respectively. The solution was warmed to room temperature for 1 hour and was heated to 120° C. in a microwave reactor for 15 minutes. The solution was cooled down and was poured into crashed ice. The solution was extracted with CH$_2$Cl$_2$ and the organic layer was collected. The solution was dried with MgSO$_4$ and was filtered. The filtrate was concentrated and the residue was purified by silica gel flash column chromatography with 5% EtOAc in Hexane as the eluent to afford the title compound (500 mg, 35%).

4,6-Dimethyl-benzo[d]isothiazole-3-carboxylic acid amide

To a solution of 4,6-dimethyl-benzo[b]thiophene-2,3-dione (100 mg, 0.5 mmol) in ammonia/MeOH (5 mL) was added 30% H$_2$O$_2$ (0.17 mL, 1.6 mmol) dropwise at room temperature. The solution was stirred at the same temperature for 2 hours. The solution was concentrated and the residue was purified by silica gel flash column chromatography with 20% EtOAc in Hexane as the eluent to afford the title compound (35 mg, 33%) as a pale red solid.

4,6-Dimethyl-benzo[d]isothiazole-3-carboxylic acid

To a solution of 4,6-dimethyl-benzo[d]isothiazole-3-carboxylic acid amide (20 mg, 0.097 mmol) in EtOH (10 mL) and H$_2$O (2 mL) was added KOH (11 mg, 0.19 mmol). The solution was heated to 85° C. for 48 hours. The solution was cooled and was placed in an ice bath. Conc. HCl was added to adjust the pH of the solution to 2. The solid that precipitated out from the solution was collected by filtration. The white solid was dried and was confirmed to be the title compound (15 mg, 75%).

4,6-Dimethyl-benzo[d]isothiazole-3-carboxylic acid methyl ester

To a solution of 4,6-dimethyl-benzo[d]isothiazole-3-carboxylic acid (10 mg, 0.048 mmol) in MeOH (5 mL) was added conc. H$_2$SO$_4$ (0.1 mL) at room temperature. The solution was heated up to 60° C. for 24 hours. The solution was cooled and was neutralized with sat. NaHCO$_3$. The solution was extracted with EtOAc. The combined organic layer was dried over MgSO$_4$ and filtered. The filtrate was concentrated and the residue was purified by silica gel flash column chromatography with 20% EtOAc in Hexane as the eluent to afford the title compound (10 mg, 94%) as colorless oil.

(4,6-Dimethyl-benzo[d]isothiazol-3-yl)-methanol

To a solution of 4,6-dimethyl-benzo[d]isothiazole-3-carboxylic acid methyl ester (100 mg, 0.45 mmol) in THF (10 mL) was added lithium aluminum hydride (LiAlH$_4$) (34 mg, 0.9 mmol) at 0° C. under nitrogen atmosphere. The solution was stirred at the same temperature for 1 hour. Sat. NaHCO$_3$ was added and the solution was extracted with EtOAc. The combined organic layer was dried with MgSO$_4$ and filtered. The filtrate was concentrated and the residue was used in the next step of the synthesis without further purification.

3-Bromomethyl-4,6-dimethyl-benzo[d]isothiazole

To a solution of (4,6-dimethyl-benzo[d]isothiazol-3-yl)-methanol (100 mg, 0.5 mmol) in CH$_2$Cl$_2$ (15 mL) were added triphenylphosphine (PPh₃) (200 mg, 0.78 mmol) and carbon tetrabromide (CBr₄) (340 mg, 1 mmol) at room temperature. The solution was stirred at the same temperature for 1 hour. The solution was concentrated and the residue was purified by silica gel flash column chromatography with 10% EtOAc in Hexane as the eluent to afford the title compound (90 mg, 68%) as a white solid.

(R)-3-[3-(4,6-Dimethyl-benzo[d]isothiazol-3-ylmethyl)-2-oxo-2,3-dihydro-imidazo[4,5-c]pyridin-1-yl]-3-phenyl-propionic acid ethyl ester To a solution of (R)-3-(2-oxo-2,3-dihydro-imidazo[4,5-c]pyridin-1-yl)-3-phenyl-propionic acid ethyl ester (refer to example 2) (50 mg, 0.16 mmol) in DMF (10 mL) were added 3-Bromomethyl-4,6-dimethyl-benzo[d]isothiazol (62 mg, 0.24 mmol) and K₂CO₃ (44 mg, 0.32 mmol) at room temperature under nitrogen atmosphere. The solution was heated to 100° C. for 2 hours. The solution was cooled and water was added. The solution was extracted with EtOAc and the combined organic layer was dried with MgSO₄. The solution was filtered and concentrated. The residue was purified by silica gel flash column chromatography with 20% EtOAc in Hexane as the eluent to afford the title compound (15 mg, 90%) as colorless foam.

(R)-3-[3-(4,6-Dimethyl-benzo[d]isothiazol-3-ylmethyl)-2-oxo-2,3-dihydro-imidazo[4,5-c]pyridin-1-yl]-3-phenyl-propionic acid To a solution of (R)-3-[3-(4,6-dimethyl-benzo[d]isothiazol-3-ylmethyl)-2-oxo-2,3-dihydro-imidazo[4,5-c]pyridin-1-yl]-3-phenyl-propionic acid ethyl ester (10 mg, 0.021 mmol) in 1,4-dioxane (5 mL) and water (1 mL) was added lithium hydroxide (LiOH) (0.9 mg, 0.042 mmol) at room temperature. The solution was stirred at the same temperature for 4 hours. The solution was concentrated and water was added to the residue. The solution was acidified by 12N HCl in an ice-bath. The solution was concentrated and the residue was purified by preparative TLC with 10% MeOH in CH₂Cl₂ as the eluent to afford the title compound (8.3 mg, 88%): LCMS, M⁺+1, m/z: 459.13 as a white solid.

The following compound was synthesized with similar procedure using (R)-3-(2-oxo-1,2-dihydro-imidazo[4,5-b]pyridin-3-yl)-3-phenyl-propionic acid ethyl ester (example 2)

(R)-3-[1-(4,6-Dimethyl-benzo[d]isothiazol-3-ylmethyl)-2-oxo-1,2-dihydro-imidazo[4,5-b]pyridin-3-yl]-3-phenyl-propionic acid. LCMS, M⁺+1, m/z: 459.15

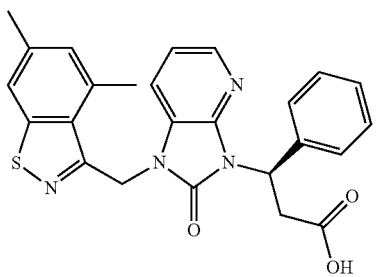 [SMILES: Cc1cc(C)c2c(Cn3c(=O)n([C@H](CC(=O)O)c4ccccc4)c4ncccc43)nsc2c1]

Example 5

(R)-3-[2-Oxo-1-(1,4,6-trimethyl-1H-indol-3-ylmethyl)-1,2-dihydro-imidazo[4,5-b]pyridin-3-yl]-3-phenyl-propionic acid

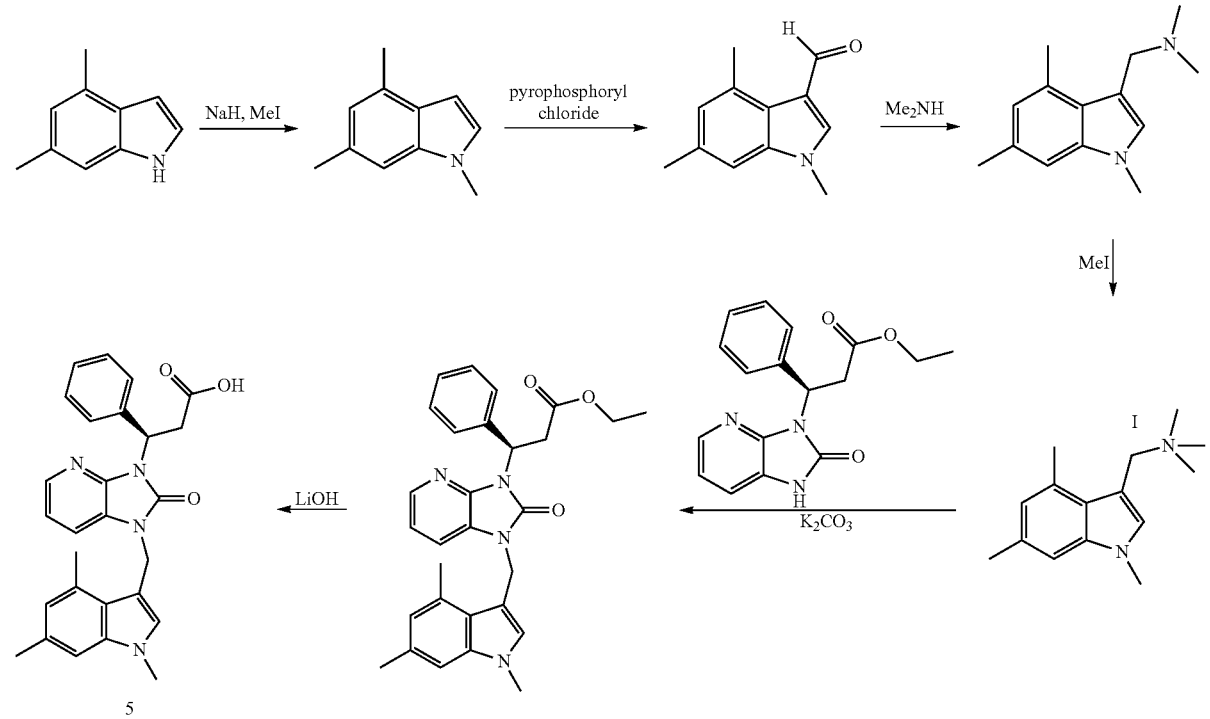

1,4,6-Trimethyl-1H-indole

A solution of the 4,6-dimethylindole (750 mg, 5.2 mmol) in DMF (20 mL) was cooled to 0° C. under nitrogen and treated with 60% sodium hydride in mineral oil (413 mg, 10.3 mmol). After stirring for 15 minutes, iodomethane (0.4 mL, 6.2 mmol) was introduced and the cooling bath was removed (reaction became light purple). After 30 minutes the solution was subsequently quenched with water (5 ml) and then concentrated to reduce the volume of DMF. The reaction was poured into water (200 mL) and EtOAc (100 mL). The layers were separated and the aqueous phase was extracted with EtOAc (3×200 mL). The combined organics were washed with water (3×) and then dried (MgSO$_4$), filtered and concentrated. The residue was purified by silica gel flash column chromatography with 10% EtOAc in Hexane as the eluent to afford the title compound (700 mg, 80%) as a white solid.

1,4,6-Trimethyl-1H-indole-3-carbaldehyde

A solution of 1,4,6-trimethyl-1H-indole (800 mg, 5 mmol) in DMF (0.9 mL) was cooled to 5° C. under nitrogen. The pyrophosphoryl chloride (1.4 mL, 10 mmol) was then slowly introduced. Upon complete addition the cooling bath was removed and the reaction was allowed to warm to ambient temperature. After a total of 45 minutes the reaction was cooled to 5° C. and slowly quenched with 2N NaOH. The pH was adjusted to 8. The solid that precipitate out from the solution was collected by filtration and was washed with water. The remaining white solid was dried in the oven and was confirmed to be the title compound (875 mg, 93%).

Dimethyl-(1,4,6-trimethyl-1H-indol-3-ylmethyl)-amine

To a solution of 1,4,6-trimethyl-1H-indole-3-carbaldehyde (875 mg, 4.7 mmol) in CH$_2$Cl$_2$ (30 mL) and dimethylamine (2.0 M solution in MeOH) (4.7 mL, 9.3 mmol) was added sodium triacetoxyborohydride (NaBH(OAc)$_3$) (2.9 g, 14 mmol) at 0° C. Upon complete addition the cooling bath was removed and the reaction mixture was stirred at room temperature for 48 h. When the reaction was complete, the mixture was diluted with CH$_2$Cl$_2$ and washed with saturated NaHCO$_3$. The layers were separated and the organic phase was dried over MgSO$_4$, filtered and concentrated. The residue was used in the next step of the synthesis without purification.

Trimethyl-(1,4,6-trimethyl-1H-indol-3-ylmethyl)-amino iodide

To a stirred solution of dimethyl-(1,4,6-trimethyl-1H-indol-3-ylmethyl)-amine (910 mg, 4.2 mmol) in acetonitrile (10 mL) was added iodomethane (0.3 mL, 5 mmol) at room temperature. The solution was stirred at the same temperature for 5 hours. The solution was concentrated and the resulting white solid was washed with small amount of cold Et$_2$O and was filtered. The white solid (1 g, 66%) was used in the next step of the synthesis without further purification.

(R)-3-[2-Oxo-1-(1,4,6-trimethyl-1H-indol-3-ylmethyl)-1,2-dihydro-imidazo[4,5-b]pyridin-3-yl]-3-phenyl-propionic acid ethyl ester To a solution of (R)-3-(2-oxo-1,2-dihydro-imidazo[4,5-b]pyridin-3-yl)-3-phenyl-propionic acid ethyl ester (refer to example 2) (80 mg, 0.26 mmol) in DMF (10 mL) were added trimethyl-(1,4,6-trimethyl-1H-indol-3-ylmethyl)-amino iodide (138 mg, 0.39 mmol) and K$_2$CO$_3$ (71 mg, 0.51 mmol) at room temperature. The solution was heated at 100° C. for 4 hours. The solution was cooled and was extracted with water and EtOAc. The combined organic layer was dried with MgSO$_4$ and filtered. The filtrate was concentrated and the residue was purified by silica gel flash column chromatography with 20% EtOAc in Hexane as the eluent to afford the title compound (100 mg, 81%) as white foam.

(R)-3-[2-Oxo-1-(1,4,6-trimethyl-1H-indol-3-ylmethyl)-1,2-dihydro-imidazo[4,5-b]pyridin-3-yl]-3-phenyl-propionic acid To a solution of (R)-3-[2-oxo-1-(1,4,6-trimethyl-1H-indol-3-ylmethyl)-1,2-dihydro-imidazo[4,5-b]pyridin-3-yl]-3-phenyl-propionic acid ethyl ester (80 mg, 0.17 mmol) in 1,4-dioxane (10 mL) and water (2 mL) was added LiOH (7.9 mg, 0.33 mmol) at room temperature. The solution was stirred at the same temperature for 6 hours. The solution was concentrated and water was added to the residue. The solution was acidified by 12N HCl in an ice-bath. The solid that precipitated out from the solution was collected by filtration and was dried under vacuum. The resulting white solid was confirmed to be the title compound (65 mg, 87%): LCMS, M$^+$+1, m/z: 455.91.

The following compound was synthesized with similar procedure using (R)-3-(5-methoxy-2-oxo-1,2-dihydro-imidazo[4,5-b]pyridin-3-yl)-3-phenyl-propionic acid ethyl ester (example 2).

(R)-3-[5-Methoxy-2-oxo-1-(1,4,6-trimethyl-1H-indol-3-ylmethyl)-1,2-dihydro-imidazo[4,5-b]pyridin-3-yl]-3-phenyl-propionic acid. LCMS, M$^+$+1, m/z: 485.95.

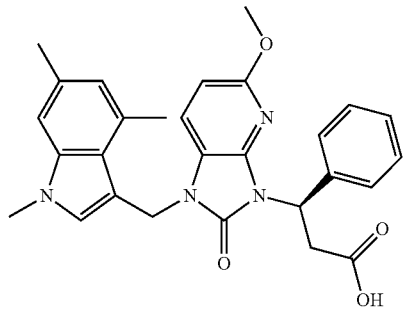 [SMILES: COc1ccc2c(n1)n([C@H](CC(=O)O)c1ccccc1)c(=O)n2Cc1cn(C)c2cc(C)cc(C)c12]

Example 6

2-[1-(1,4-Dimethyl-1H-indol-3-ylmethyl)-2-oxo-1,2-dihydro-imidazo[4,5-b]pyridin-3-ylmethyl]-pentanoic acid

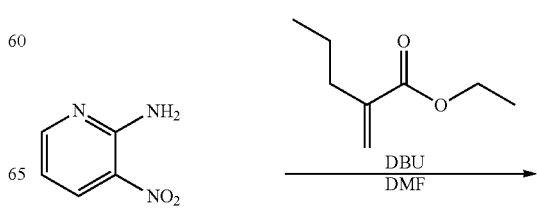

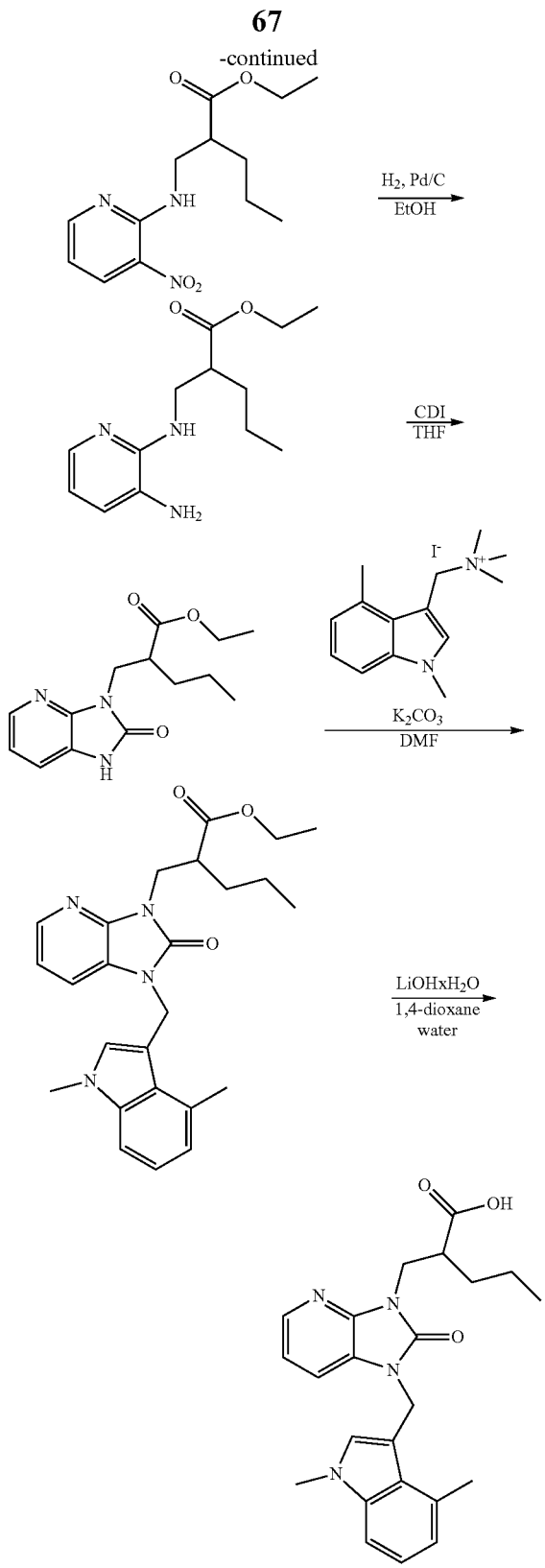

2-[(3-Nitro-pyridin-2-ylamino)-methyl]-pentanoic acid ethyl ester

To a stirred solution of 2-amino-3-nitropyridine (390 mg, 2.80 mmol) in DMF (3 ml) was added ethyl 2-propylacrylate (500 mg, 3.52 mmol) followed by 1,8-diazabicyclo[5.4.0] undec-7-ene (DBU) (30 µl). The mixture was warmed to 80° C. and monitored by TLC (silica gel, 30% EtOAc/hexanes). After 48 hours, only starting material was detected by TLC. The reaction mixture was warmed to 100° C. for 4 days and cooled to room temperature. The reaction was poured into water and EtOAc. The layers were separated and the aqueous phase was extracted once more with EtOAc. The combined organics were dried (MgSO$_4$), filtered and concentrated to give the crude product which was purified via silica gel flash column chromatography (Companion, 12 g silica gel, 15-50% EtOAc/hexanes). The product-containing fractions were combined and concentrated to give 90 mg (11%) of the desired compound which was used without further purification.

2-[(3-Amino-pyridin-2-ylamino)-methyl]-pentanoic acid ethyl ester

To a solution of 2-[(3-nitro-pyridin-2-ylamino)-methyl]-pentanoic acid ethyl ester (90 mg, 0.32 mmol) in EtOH (5 mL) was added Pd/C (20 mg). The reaction mixture was de-gassed using house vacuum and saturated with H$_2$. The reaction mixture was stirred at room temperature for 18 hours. The mixture was filtered through a pad of celite and the filtrate was concentrated to afford 70 mg (87%) of the desired product which was used for the next reaction without further purification.

2-(2-Oxo-1,2-dihydro-imidazo[4,5-b]pyridin-3-ylmethyl)-pentanoic acid ethyl ester To a stirred solution of 2-[(3-amino-pyridin-2-ylamino)-methyl]-pentanoic acid ethyl ester (70 mg, 0.28 mmol) in THF (10 ml) was added CDI (135 mg, 0.84 mmol). The resulting solution was stirred at room temperature for 5 days after which time the reaction appeared to be complete. Silica gel was added and the mixture was concentrated. The remaining solid was purified via silica gel flash column chromatography (Companion, 12 g silica gel, 30-100% EtOAc/hexanes) to give 50 mg (65%) of the title compound as oil which solidified on standing.

2-[1-(1,4-Dimethyl-1H-indol-3-ylmethyl)-2-oxo-1,2-dihydro-imidazo[4,5-b]pyridin-3-ylmethyl]-pentanoic acid ethyl ester To a solution of 2-(2-oxo-1,2-dihydro-imidazo[4,5-b]pyridin-3-ylmethyl)-pentanoic acid ethyl ester (50 mg, 0.18 mmol) in DMF (5 ml) were added (1,4-dimethyl-1H-indol-3-ylmethyl)-trimethyl-ammonium iodide (75 mg, 0.22 mmol) and K$_2$CO$_3$ (75 mg, 0.54 mmol) at room temperature under nitrogen atmosphere. The solution was heated to 60° C. for 3 hours. The solution was cooled and poured into water (100 ml) and EtOAc. The layers were separated and the aqueous phase was extracted with EtOAc twice. The combined organics were dried (MgSO$_4$), filtered and concentrated. The remaining residue was purified via silica gel flash column chromatography (Companion, 4 g silica gel, 20-100% EtOAc/hexanes) to give 85 mg (108%) of the title compound.

2-[1-(1,4-Dimethyl-1H-indol-3-ylmethyl)-2-oxo-1,2-dihydro-imidazo[4,5-b]pyridin-3-ylmethyl]-pentanoic acid To a stirred solution of 2-[1-(1,4-dimethyl-1H-indol-3-ylmethyl)-2-oxo-1,2-dihydro-imidazo[4,5-b]pyridin-3-ylmethyl]-pentanoic acid ethyl ester (85 mg, 0.20 mmol) in dioxane (5 ml) and water (1.5 ml) was added lithium hydroxide monohydrate (41 mg, 0.98 mmol) at room temperature. After stirring overnight the reaction appeared complete. The reaction was concentrated to low volume and diluted with water (~20 ml). Acidified using HOAc and collected the resulting precipitate via filtration. The product was suspended in 2 ml of 1:1 MeOH/acetonitrile, filtered and washed with acetonitrile. The solid was dried on house vacuum to give 25 mg (31%) of the title compound. LCMS, M⁺+1, m/z: 407.91.

Example 7

(R)-3-[5-Cyano-1-(1,4-dimethyl-1H-indol-3-ylmethyl)-2-oxo-1,2-dihydro-imidazo[4,5-b]pyridin-3-yl]-3-phenyl-propionic acid

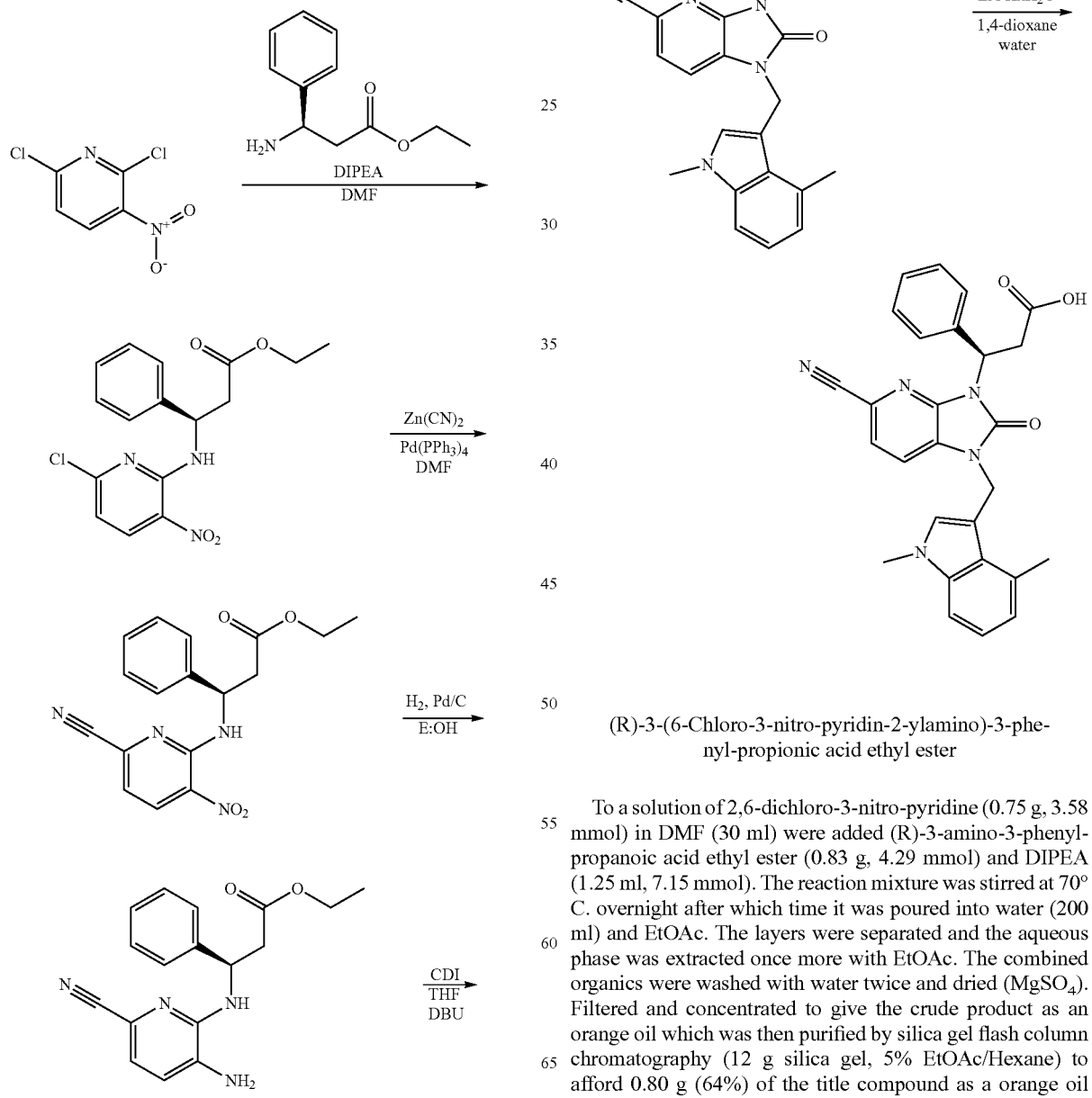

(R)-3-(6-Chloro-3-nitro-pyridin-2-ylamino)-3-phenyl-propionic acid ethyl ester

To a solution of 2,6-dichloro-3-nitro-pyridine (0.75 g, 3.58 mmol) in DMF (30 ml) were added (R)-3-amino-3-phenyl-propanoic acid ethyl ester (0.83 g, 4.29 mmol) and DIPEA (1.25 ml, 7.15 mmol). The reaction mixture was stirred at 70° C. overnight after which time it was poured into water (200 ml) and EtOAc. The layers were separated and the aqueous phase was extracted once more with EtOAc. The combined organics were washed with water twice and dried (MgSO₄). Filtered and concentrated to give the crude product as an orange oil which was then purified by silica gel flash column chromatography (12 g silica gel, 5% EtOAc/Hexane) to afford 0.80 g (64%) of the title compound as a orange oil which was used without further purification.

(R)-3-(6-Cyano-3-nitro-pyridin-2-ylamino)-3-phenyl-propionic acid ethyl ester In a microwave reaction vessel was dissolved (R)-3-(6-chloro-3-nitro-pyridin-2-ylamino)-3-phenyl-propionic acid ethyl ester (0.75 g, 2.14 mmol) in DMF (12 ml). Added the zinc cyanide (0.15 g, 1.29 mmol) and tetrakis(triphenylphosphine)palladium(0) (0.25 g, 0.21 mmol). Reaction mixture was degassed using a stream of nitrogen and capped. Reaction was heated in a microwave at 120° C. for 1 hour and then stirred at room temperature for 72 hours. After this time the reaction was poured into water and EtOAc. The layers were separated and the aqueous phase was extracted with EtOAc (3×). The combined organics were dried ($MgSO_4$), filtered and concentrated to give the crude product which was purified via silica gel flash column chromatography (12 g silica gel, 5-20% EtOAc/hexanes) to afford 0.70 g (96%) of the title compound.

(R)-3-(3-Amino-6-cyano-pyridin-2-ylamino)-3-phenyl-propionic acid ethyl ester To a solution of (R)-3-(6-cyano-3-nitro-pyridin-2-ylamino)-3-phenyl-propionic acid ethyl ester (0.70 g, 2.06 mmol) in EtOH (20 mL) was added Pd/C (140 mg). The reaction mixture was de-gassed using house vacuum and saturated with $H_2$. The reaction mixture was stirred at room temperature for 2 hours. The mixture was filtered through a pad of celite and the filtrate was concentrated to afford 0.60 g (94%) of the title compound, which was used for the next reaction without further purification.

(R)-3-(5-Cyano-2-oxo-1,2-dihydro-imidazo[4,5-b]pyridin-3-yl)-3-phenyl-propionic acid ethyl ester To a stirred solution of (R)-3-(3-amino-6-cyano-pyridin-2-ylamino)-3-phenyl-propionic acid ethyl ester (600 mg, 1.93 mmol) in THF (20 ml) was added CDI (630 mg, 3.87 mmol) and DBU (0.12 ml, 0.77 mmol). The resulting solution was stirred at room temperature for 18 hours after which time the reaction appeared complete. Added silica gel and concentrated. The remaining solid was purified via silica gel flash column chromatography (Companion, 12 g silica gel, 30-60% EtOAc/hexanes) to give 120 mg (19%) of the title compound.

(R)-3-[5-Cyano-1-(1,4-dimethyl-1H-indol-3-ylmethyl)-2-oxo-1,2-dihydro-imidazo[4,5-b]pyridin-3-yl]-3-phenyl-propionic acid ethyl ester To a solution of (R)-3-(5-cyano-2-oxo-1,2-dihydro-imidazo[4,5-b]pyridin-3-yl)-3-phenyl-propionic acid ethyl ester (60 mg, 0.18 mmol) in DMF (5 ml) were added (1,4-dimethyl-1H-indol-3-ylmethyl)-trimethyl-ammonium iodide (74 mg, 0.21 mmol) and $K_2CO_3$ (30 mg, 0.21 mmol) at room temperature under nitrogen atmosphere. The solution was heated at 60° C. for 18 hours. The solution was cooled and poured into water and EtOAc. The layers were separated and the aqueous phase was extracted with EtOAc (1×). The combined organics were dried ($MgSO_4$), filtered and concentrated. The remaining residue was purified via silica gel flash column chromatography (Companion, 12 g silica gel, 30-50% EtOAc/hexanes) to give 70 mg (80%) of the title compound as foam.

(R)-3-[5-Cyano-1-(1,4-dimethyl-1H-indol-3-ylmethyl)-2-oxo-1,2-dihydro-imidazo[4,5-b]pyridin-3-yl]-3-phenyl-propionic acid To a stirred solution of (R)-3-[5-cyano-1-(1,4-dimethyl-1H-indol-3-ylmethyl)-2-oxo-1,2-dihydro-imidazo[4,5-b]pyridin-3-yl]-3-phenyl-propionic acid ethyl ester (70 mg, 0.14 mmol) in dioxane (4 ml) and water (2 ml) was added lithium hydroxide monohydrate (12 mg, 0.28 mmol) at room temperature. After stirring for 6 hours the reaction appeared to be complete. The reaction was concentrated to a low volume and diluted with water. The reaction mixture was acidified using acetic acid and the resulting precipitate was collected via filtration. The solid was purified once by silica gel flash column chromatography (12 g silica gel, 0-10% MeOH/Dichloromethane) and then again by preparative TLC (2×0.5 mm silica gel, 5% MeOH/Dichloromethane) to afford 25 mg (31%) of the title compound. LCMS, $M^++1$, m/z: 466.43.

The following compound was prepared in the same manner using trimethyl-(1,4,6-trimethyl-1H-indol-3-ylmethyl)-ammonium iodide.

(R)-3-[5-Cyano-2-oxo-1-(1,4,6-trimethyl-1H-indol-3-ylmethyl)-1,2-dihydro-imidazo[4,5-b]pyridin-3-yl]-3-phenyl-propionic acid. LCMS, $M^++1$, m/z: 480.73.

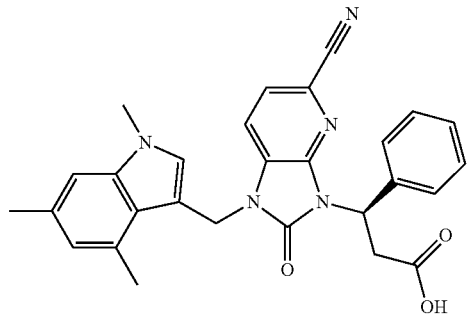 [SMILES: Cc1cc(C)c2c(Cn3c(=O)n([C@H](CC(=O)O)c4ccccc4)c4nc(C#N)ccc43)cn(C)c2c1]

The following compound was prepared in the same manner using (R)-3-amino-3-(4-fluoro-phenyl)-propionic acid methyl ester hydrochloride.

(R)-3-[5-Cyano-1-(1,4-dimethyl-1H-indol-3-ylmethyl)-2-oxo-1,2-dihydro-imidazo[4,5-b]pyridin-3-yl]-3-(4-fluoro-phenyl)-propionic acid. LCMS, $M^++1$, m/z: 484.20.

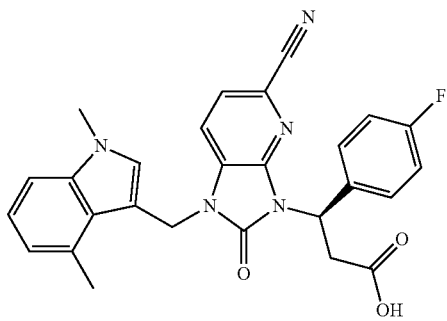 [SMILES: Cc1cccc2c1c(Cn1c(=O)n([C@H](CC(=O)O)c3ccc(F)cc3)c3nc(C#N)ccc31)cn2C]

The following compound was prepared in the same manner using (R)-3-amino-3-(4-fluoro-phenyl)-propionic acid methyl ester hydrochloride and trimethyl-(1,4,6-trimethyl-1H-indol-3-ylmethyl)-ammonium iodide.

(R)-3-[5-Cyano-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid. LCMS, M⁺+1, m/z: 498.20.

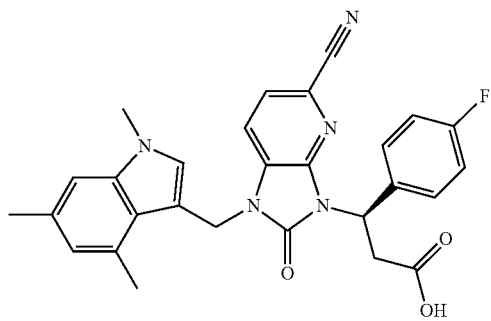 [SMILES: Cc1cc(C)c2c(Cn3c(=O)n([C@H](CC(=O)O)c4ccc(F)cc4)c4nc(C#N)ccc43)cn(C)c2c1]

The following compound was prepared in the same manner using 3-amino-hexanoic acid methyl ester hydrochloride.

3-[5-Cyano-1-(1,4-dimethyl-1H-indol-3-ylmethyl)-2-oxo-1,2-dihydro-imidazo[4,5-b]pyridin-3-yl]-hexanoic acid. LCMS, M⁺+1, m/z: 432.20.

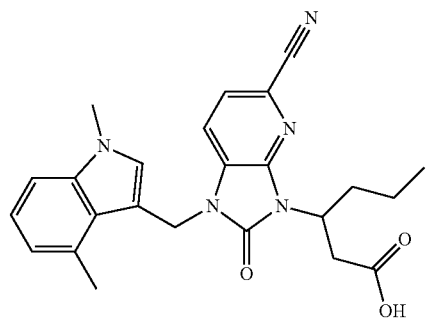 [SMILES: CCCC(CC(=O)O)n1c(=O)n(Cc2cn(C)c3cccc(C)c23)c2ccc(C#N)nc21]

The following compound was prepared in the same manner using 3-amino-hexanoic acid methyl ester hydrochloride and trimethyl-(1,4,6-trimethyl-1H-indol-3-ylmethyl)-ammonium iodide.

3-[5-Cyano-2-oxo-1-(1,4,6-trimethyl-1H-indol-3-ylmethyl)-1,2-dihydro-imidazo[4,5-b]pyridin-3-yl]-hexanoic acid. LCMS, M⁺+1, m/z: 446.20.

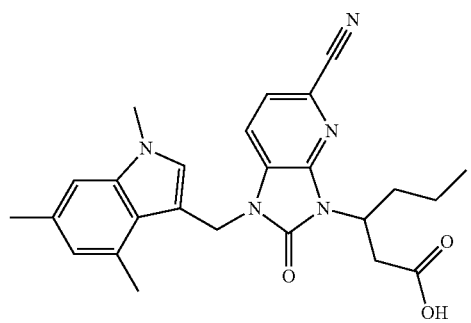 [SMILES: CCCC(CC(=O)O)n1c(=O)n(Cc2cn(C)c3cc(C)cc(C)c23)c2ccc(C#N)nc21]

The following compound was prepared in the same manner using (R)-3-amino-3-(4-chloro-phenyl)-propionic acid methyl ester hydrochloride.

(R)-3-(4-Chloro-phenyl)-3-[5-cyano-1-(1,4-dimethyl-1H-indol-3-ylmethyl)-2-oxo-1,2-dihydro-imidazo[4,5-b]pyridin-3-yl]-propionic acid. LCMS, M⁺+1, m/z: 500.20.

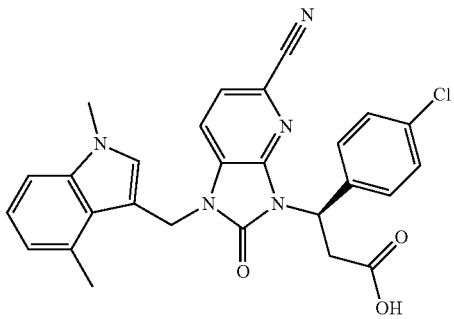 [SMILES: Cc1cccc2c1c(Cn1c(=O)n([C@H](CC(=O)O)c3ccc(Cl)cc3)c3nc(C#N)ccc31)cn2C]

The following compound was prepared in the same manner using (R)-3-amino-3-(4-chloro-phenyl)-propionic acid methyl ester hydrochloride and trimethyl-(1,4,6-trimethyl-1H-indol-3-ylmethyl)-ammonium iodide.

(R)-3-(4-Chloro-phenyl)-3-[5-cyano-2-oxo-1-(1,4,6-trimethyl-1H-indol-3-ylmethyl)-1,2-dihydro-imidazo[4,5-b]pyridin-3-yl]-propionic acid. LCMS, M⁺+1, m/z: 514.20.

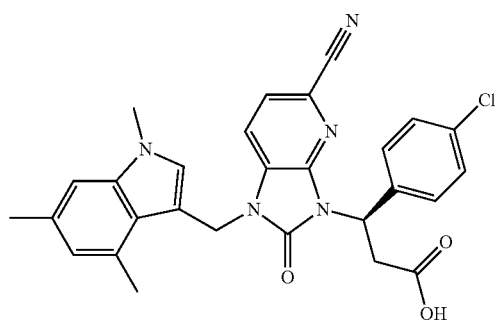 [SMILES: Cc1cc(C)c2c(Cn3c(=O)n([C@H](CC(=O)O)c4ccc(Cl)cc4)c4nc(C#N)ccc43)cn(C)c2c1]

Example 8

3-[5-Carbamoyl-2-oxo-1-(1,4,6-trimethyl-1H-indol-3-ylmethyl)-1,2-dihydro-imidazo[4,5-b]pyridin-3-yl]-hexanoic acid

75
-continued

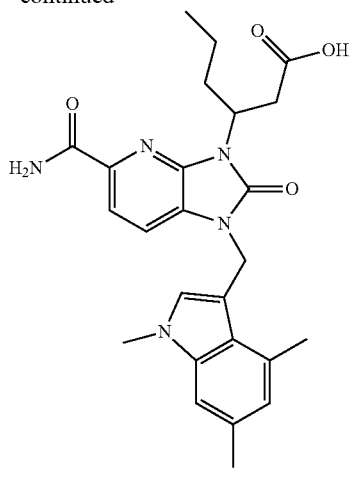

3-[5-Carbamoyl-2-oxo-1-(1,4,6-trimethyl-1H-indol-3-ylmethyl)-1,2-dihydro-imidazo[4,5-b]pyridin-3-yl]-hexanoic acid Sulfuric acid (0.1 ml) was cooled in an ice bath and treated with 3-[5-cyano-1-(1,4-dimethyl-1H-indol-3-ylmethyl)-2-oxo-1,2-dihydro-imidazo[4,5-b]pyridin-3-yl]-hexanoic acid (20 mg, 0.04 mmol). The reaction was gradually warmed to room temperature and monitored by LC-MS. After stirring over night the reaction was diluted with water and the white precipitate was collected via filtration. The precipitate was washed with water and dried to afford 20 mg (96%) of the title compound. LCMS, M$^+$+1, m/z: 464.20.

Example 9

(R)-3-[5-Carbamoyl-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid

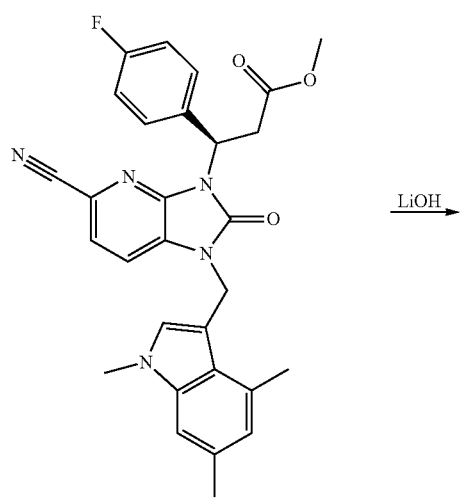

76
-continued

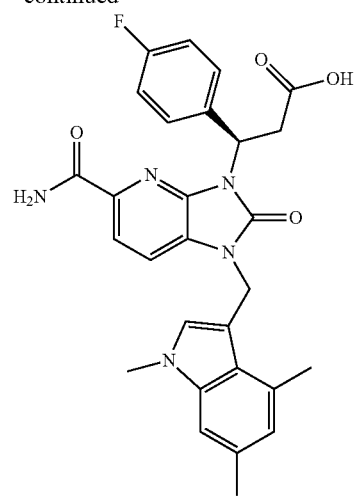

(R)-3-[5-Carbamoyl-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid To a stirred solution of (R)-3-[5-cyano-2-oxo-1-(1,4,6-trimethyl-1H-indol-3-ylmethyl)-1,2-dihydro-imidazo[4,5-b]pyridin-3-yl]-3-(4-fluoro-phenyl)-propionic acid methyl ester (0.17 g, 0.33 mmol) in dioxane (10 ml) and water (3 ml) was added lithium hydroxide monohydrate (70 mg, 1.66 mmol). The reaction was stirred for 24 hours after which time it was diluted with water and acidified using acetic acid. The resulting precipitate was collected via filtration and washed with water. The remaining solid was purified via preparative TLC (2×1 mm silica gel plates, 5% MeOH/Dichloromethane) to afford 22 mg (13%) of the title compound. LCMS, M$^+$+1, m/z: 516.20.

Example 10

2-Methyl-propane-2-sulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide

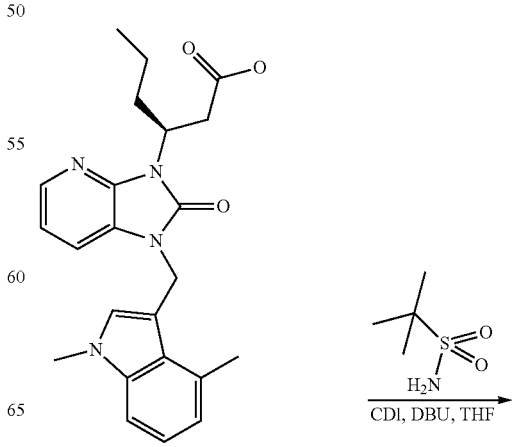

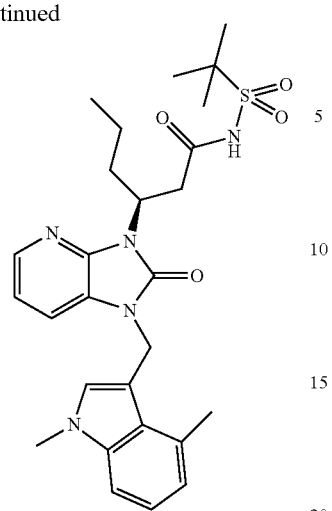
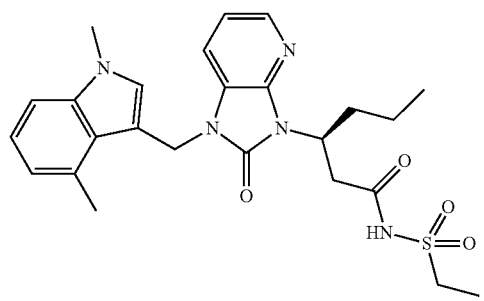

The following compound was prepared in the same manner using 1-methyl-1H-imidazole-4-sulfonic amide.

1-Methyl-1H-imidazole-4-sulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide. LCMS, M$^+$+1, m/z: 549.64

L (S)-3-[1-(1,4-Dimethyl-1H-indol-3-ylmethyl)-2-oxo-1,2-dihydro-imidazo[4,5-b]pyridin-3-yl]-hexanoic acid is synthesized as in example 1

(S)-3-[1-(1,4-Dimethyl-1H-indol-3-ylmethyl)-2-oxo-1,2-dihydro-imidazo[4,5-b]pyridin-3-yl]-hexanoic acid (85 mg, 0.21 mmol) was dissolved in THF (1.0 mL) and CDI (76 mg, 0.47 mmol) was added at room temperature. The mixture was heated at 55° C. for 1 hour. After the mixture is cooled down to room temperature, 2-methyl-propane-2-sulfonic acid amide (57 mg, 0.42 mmol) was added and after 10 min, DBU (0.063 mL, 0.42 mmol) was added. The mixture was stirred for 16 hours at room temperature. Then 2.0 mL of 1.0 M HCl was added followed by 30 mL of water. The mixture is extracted with EtOAc (3×20 mL) and the organic layers were combined, dried and concentrated to give crude product. Purification first by flash column chromatography using 5% MeOH in CH$_2$Cl$_2$ then by preparative TLC (6% MeOH in CH$_2$Cl$_2$ with 1% concentrated NH$_4$OH) afforded 79 mg (71%) of the title compound. LCMS, M$^+$+1, m/z: 526.13.

The following compound was prepared in the same manner using methyl sulfonic acid amide.

N-{(S)-3-[1-(1,4-Dimethyl-1H-indol-3-ylmethyl)-2-oxo-1,2-dihydro-imidazo[4,5-b]pyridin-3-yl]-hexanoyl}-methanesulfonamide LCMS, M$^+$+1, m/z: 483.58

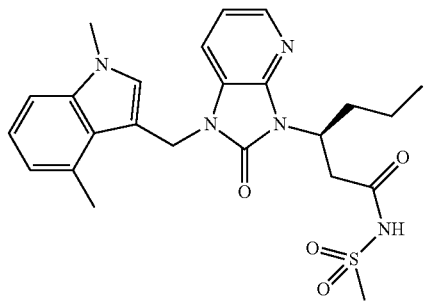 [SMILES: CCC[C@@H](CC(=O)NS(C)(=O)=O)n1c(=O)n(Cc2cn(C)c3cccc(C)c23)c2cccnc21]

The following compound was prepared in the same manner using ethyl sulfonic acid amide.

Ethanesulfonic acid {(S)-3-[1-(1,4-dimethyl-1H-indol-3-ylmethyl)-2-oxo-1,2-dihydro-imidazo[4,5-b]pyridin-3-yl]-hexanoyl}-amide. LCMS, M$^+$+1, m/z: 497.61

Example 11

(R)-3-[2-Cyclopropyl-7-(1,4-dimethyl-1H-indol-3-ylmethyl)-8-oxo-7,8-dihydro-purin-9-yl]-3-phenyl-propionic acid

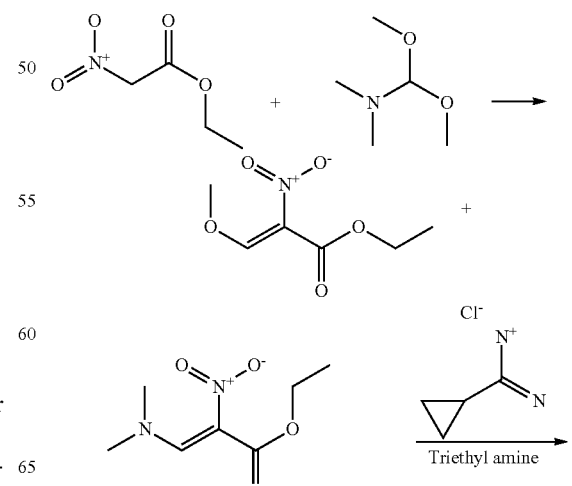

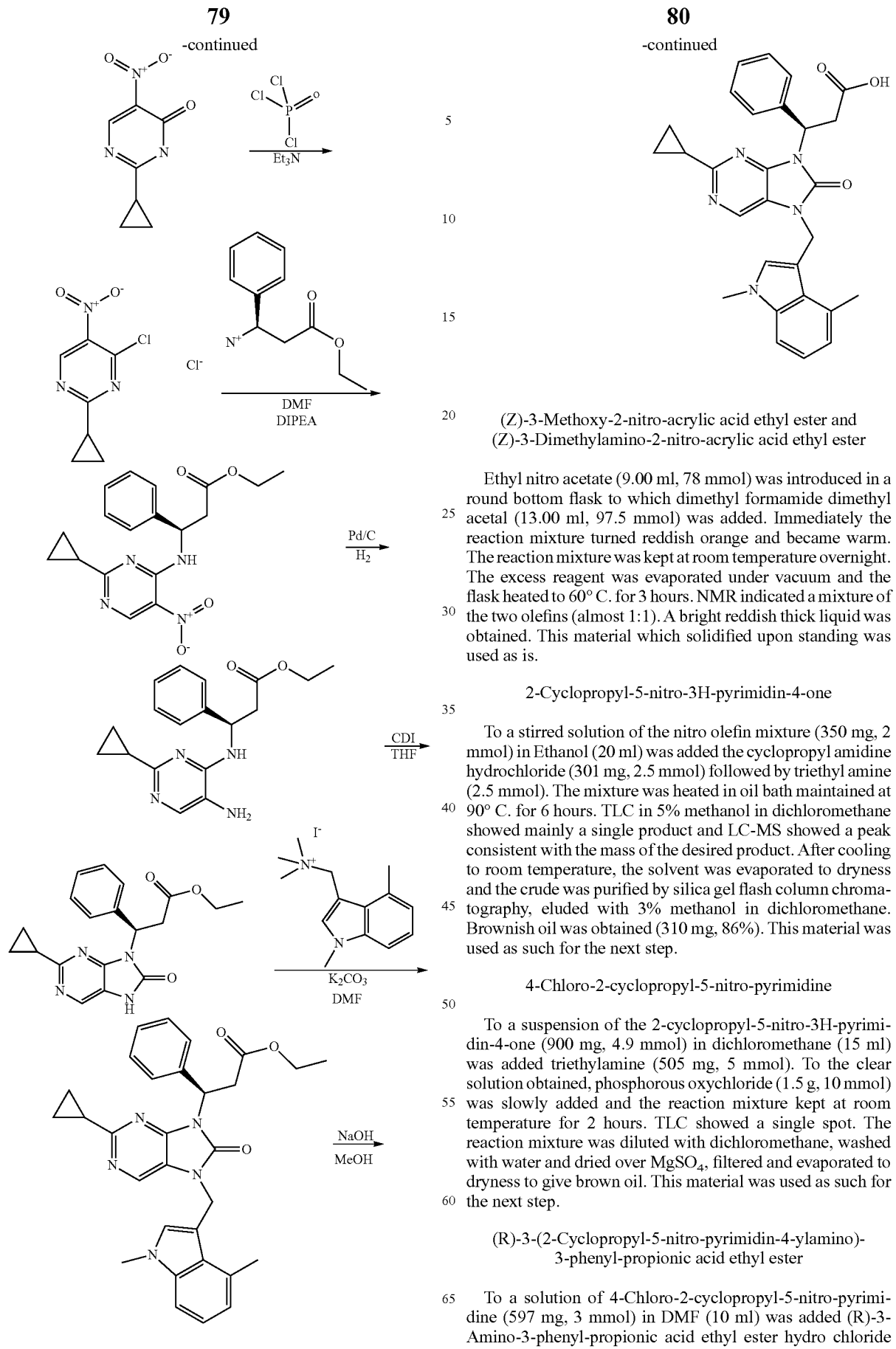

(Z)-3-Methoxy-2-nitro-acrylic acid ethyl ester and (Z)-3-Dimethylamino-2-nitro-acrylic acid ethyl ester Ethyl nitro acetate (9.00 ml, 78 mmol) was introduced in a round bottom flask to which dimethyl formamide dimethyl acetal (13.00 ml, 97.5 mmol) was added. Immediately the reaction mixture turned reddish orange and became warm. The reaction mixture was kept at room temperature overnight. The excess reagent was evaporated under vacuum and the flask heated to 60° C. for 3 hours. NMR indicated a mixture of the two olefins (almost 1:1). A bright reddish thick liquid was obtained. This material which solidified upon standing was used as is.

2-Cyclopropyl-5-nitro-3H-pyrimidin-4-one

To a stirred solution of the nitro olefin mixture (350 mg, 2 mmol) in Ethanol (20 ml) was added the cyclopropyl amidine hydrochloride (301 mg, 2.5 mmol) followed by triethyl amine (2.5 mmol). The mixture was heated in oil bath maintained at 90° C. for 6 hours. TLC in 5% methanol in dichloromethane showed mainly a single product and LC-MS showed a peak consistent with the mass of the desired product. After cooling to room temperature, the solvent was evaporated to dryness and the crude was purified by silica gel flash column chromatography, eluded with 3% methanol in dichloromethane. Brownish oil was obtained (310 mg, 86%). This material was used as such for the next step.

4-Chloro-2-cyclopropyl-5-nitro-pyrimidine

To a suspension of the 2-cyclopropyl-5-nitro-3H-pyrimidin-4-one (900 mg, 4.9 mmol) in dichloromethane (15 ml) was added triethylamine (505 mg, 5 mmol). To the clear solution obtained, phosphorous oxychloride (1.5 g, 10 mmol) was slowly added and the reaction mixture kept at room temperature for 2 hours. TLC showed a single spot. The reaction mixture was diluted with dichloromethane, washed with water and dried over $MgSO_4$, filtered and evaporated to dryness to give brown oil. This material was used as such for the next step.

(R)-3-(2-Cyclopropyl-5-nitro-pyrimidin-4-ylamino)-3-phenyl-propionic acid ethyl ester To a solution of 4-Chloro-2-cyclopropyl-5-nitro-pyrimidine (597 mg, 3 mmol) in DMF (10 ml) was added (R)-3-Amino-3-phenyl-propionic acid ethyl ester hydro chloride (582 mg, 3 mmol). The mixture was stirred on ice for 5 minutes the DIPEA (580 mg, 4.5 mmol) was added. The solution was stirred at room temperature for one hour. TLC showed disappearance of the starting material. The reaction mixture was diluted with ethyl acetate, washed with water, dried over MgSO$_4$, filtered, evaporated to dryness to give oil, which was used as such for the next step.

(R)-3-(5-Amino-2-cyclopropyl-pyrimidin-4-ylamino)-3-phenyl-propionic acid ethyl ester (R)-3-(2-cyclopropyl-5-nitro-pyrimidine-4-ylamino)-3-phenyl-propionic acid ethyl ester (1.42 g, 4 mmol) was dissolved in ethyl acetate (30 ml). To the solution Pd/C (200 mg) was added and the mixture was stirred under hydrogen at 1 atm for 1 hour. The reaction mixture was filtered and evaporated to dryness to give oil. The residue was used as such for the next step.

(R)-3-(2-Cyclopropyl-8-oxo-7,8-dihydro-purin-9-yl)-3-phenyl-propionic acid ethyl ester (R)-3-(5-Amino-2-cyclopropyl-pyrimidin-4-ylamino)-3-phenyl-propionic acid ethyl ester (880 mg, 2.7 mmol) was dissolved in THF (10 ml). To the solution CDI was added and the mixture was stirred at room temperature overnight. The reaction mixture was diluted with Ethyl acetate (100 ml) washed with water, dried over MgSO$_4$, filtered and evaporated to dryness. The black residue obtained was purified by chromatography, eluded with 3% methanol in dichloromethane to give oil (427 mg, 45%).

(R)-3-[2-Cyclopropyl-7-(1,4-dimethyl-1H-indol-3-ylmethyl)-8-oxo-7,8-dihydro-purin-9-yl]-3-phenyl-propionic acid ethyl ester To a solution of (R)-3-(2-cyclopropyl-8-oxo-7,8-dihydro-purin-9-yl)-3-phenyl-propionic acid ethyl ester (313 mg, 0.89 mmol) in DMF (5 ml) were added K$_2$CO$_3$ (234 mg, 1.7 mmol) and (1,4-Dimethyl-1H-indol-3-ylmethyl)-trimethyl-ammonium iodide (275 mg, 1.27 mmol). The reaction mixture was heated to 100° C. for 4 hours. The reaction mixture was therefore diluted with ethyl acetate and washed with water (×4). The organic phase was dried over MgSO$_4$ and concentrated. The resulting residue was purified by chromatography, eluded with 3% methanol to 10% in CH$_2$Cl$_2$ to afford the titled compound (231 mg, 50%). LCMS, M$^+$+1, m/z: 509.59.

(R)-3-[2-Cyclopropyl-7-(1,4-dimethyl-1H-indol-3-ylmethyl)-8-oxo-7,8-dihydro-purin-9-yl]-3-phenyl-propionic acid (R)-3-[2-Cyclopropyl-7-(1,4-dimethyl-1H-indol-3-ylmethyl)-8-oxo-7,8-dihydro-purin-9-yl]-3-phenyl-propionic acid ethyl ester (130 mg, 0.255 mmol) was dissolved in THF (3 ml). To the solution a concentrated solution of LiOH in water (2 ml) was added. The mixture was stirred at room temperature for 1 hour. The reaction was monitored by TLC. The reaction mixture was neutralized with 1N HCl, and then extracted with ethyl acetate 3×. The organic layer was dried over MgSO$_4$, filtered and evaporated to dryness. The white solid obtained was purified by prep TLC, eluded with 10% methanol in dichloromethane to give the title compound (52 mg, 43%). LCMS, M$^+$+1, m/z: 481.54

The following compound was prepared in the same manner using isopropyl amidine hydrochloride.

(R)-3-[7-(1,4-Dimethyl-1H-indol-3-ylmethyl)-2-isopropyl-8-oxo-7,8-dihydro-purin-9-yl]-3-phenyl-propionic acid. LCMS, M$^+$+1, m/z: 483.56

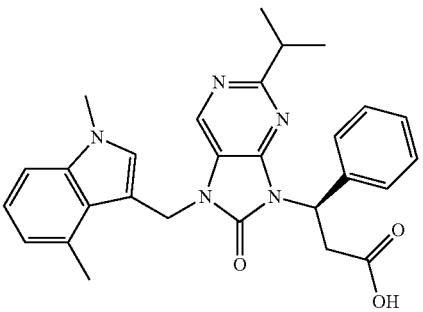 [SMILES: Cc1cccc2c1c(Cn1c(=O)n([C@H](CC(=O)O)c3ccccc3)c3nc(C(C)C)ncc31)cn2C]

METHODS OF USE

In accordance with the invention, there are provided methods of using the compounds as described herein and their pharmaceutically acceptable derivatives. The compounds used in the invention inhibit Chymase. Since Chymase is known to transform angiotensin I to angiotensin II and may contribute to activation of TGF-β, matrix proteases and cytokines, the inhibition of Chymase is an attractive means for preventing and treating a variety of diseases or conditions. Examples include heart failure including chronic heart failure (non-ischemic), post-myocardial infarction heart failure (ischemic), acute myocardial infarction, reperfusion injury, left ventricular dysfunction, cardiac fibrosis, diastolic heart failure and hypertrophic cardiomyopathy, hypertension including pulmonary hypertension, systolic hypertension and resistant hypertenstion, including coronary artery disease, peripheral arterial occlusive disease, aneurism, stable/unstable angina, restenosis, diabetic nephropathy, atrial fibrillation/ventricular arrhythmias, valvular heart disease, pericardial diseases, renal insufficiency (chronic kidney disease, end stage renal disease), stroke. The compounds of the invention may also be useful for the following procedures: coronary artery bypass grafting, percutaneous coronary intervention and stenting.

Other diseases within the scope of the invention include allergic rhinitis, dermatitis, asthma, chronic obstructive pulmonary disease (COPD), and pulmonary inflammation, osteoarthritis, bone resorption diseases, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, inflammatory bowel diseases, acute and chronic pain as well as symptoms of inflammation, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, traumatic arthritis, and sepsis. Reference in this regard may be made to U.S. Pat. No. 5,948,785; U.S. Pat. No. 6,271,238; U.S. Pat. No. 5,691,335; U.S. Pat. No. 5,814,631; U.S. Pat. No. 6,300,337; EP 1,099,690; U.S. Pat. No. 6,323,219; US 2005-0245536 A1; Fukami, et al., *Current Pharmaceutical Design* 1998, vol. 4, pp. 439-453.

As disclosed in the Background of the Invention, the compounds of the invention may contribute to activation of cytokines, they will therefore be useful for treating oncological diseases. Reference in this regard may be made to US 2005-0245536 A1. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds described herein may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Combinations with other therapeutics include but are not limited to: angiotensin II receptor blockers, angiotensin converting enzyme inhibitors, CETP inhibitors/apoA1 mimetics, adenosine diphosphate (P2Y12) inhibitors, direct thrombin inhibitors, aldosterone antagonists, factor Xa inhibitors, natriuretic peptides (ANP/BNP), renin inhibitors, anti-arrhythmics, Chymase inhibitors, HMG-CoA Reductase inhibitors (Statins), Rho kinase inhibitors, beta-blockers, Lipoprotein-associated phospholipase A2 inhibitors, cardiac glycosides, calcium channel blockers, diuretics, fibrates, Endothelin Receptor Antagonists, GPIIb/IIIa inhibitors, histone deacetylase inhibitors, heparins, nicotinic acid derivatives, vasopeptidase inhibitors, nitrites and nitrates, fatty acid oxidation inhibitors, oral anticoagulants, acyl-CoA:cholesterol acyltransferase inhibitors, thrombolytics, microsomal triglyceride transfer protein inhibitors, thiazolidinediones, adenosine receptor modulators, cholesterol absorbtion inhibitors, Advanced Glycation End products/receptor (AGE/RAGE) interaction modulators/blockers, acetyl salicylic acid, dipyridamole, gene therapy and cell therapy.

Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the above-described compounds include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:
(i) preventing the disease-state from occurring in a patient, in particular, when such patient is genetically or otherwise predisposed to the disease-state but has not yet been diagnosed as having it;
(ii) inhibiting or ameliorating the disease-state in a patient, i.e., arresting or slowing its development; or
(iii) relieving the disease-state in a patient, i.e., causing regression or cure of the disease-state.

IN VITRO ASSAY FOR INHIBITION OF CHYMASE

Chymase assays were performed in a total volume of 15 µL in Corning black opaque 384-well microtiter plates with a non-binding surface (Corning, N.Y.). The assay buffer was comprised of 20 mM Tris HCl pH 8.0, 50 mM NaCl, 0.01% CHAPS. The test compounds were serially diluted 3-fold with neat DMSO in a 96-well polypropylene plate from a 10 mM DMSO stock to give the 10 point dose response curve. 3 µL of the resulting DMSO solution were transferred to a 384-well polypropylene plate in duplicate, and 37 µL of assay buffer was added. Chymase was added to the assay plate in 3 uL of assay buffer followed by 2 uL of the appropriate compound dilution using a PlateMate Plus (Matrix Technologies Corp., Hudson, N.H.). The reaction was initiated by the addition of 10 uL rhodamine 110, bis-(succinoyl-L-alanyl-L-alanyl-L-prolyl-L-phenylalanylamide) (American Peptides, Sunnyvale, Calif.) in assay buffer containing 150 µM tris(2-carboxyethyl)phosphine (TCEP, Pierce Chemical, Rockford, Ill.) using a Multidrop (Thermo Electron Corp., Waltham, Mass.). Final assay concentrations were 500 pM chymase, 100 nM substrate, 100 µM TCEP, and 1% DMSO. The plates were incubated at 28° C. and 80% humidity for 1 hour, at which time the fluorescence was read on a Viewlux 1430 Microplate Imager (Perkin Elmer Life Sciences, Boston, Mass.) with 485 nm excitation, 530 nm emission, and a fluorescein dichroic mirror. The percentage of control values were calculated relative to assay blanks containing complete reaction minus chymase and a 100% control containing assay buffer with 1% DMSO in place of compound. IC50 values were obtained by fitting the data using XLFit4 (IDBS Software).

Preferred compounds of the invention have an activity of 100 nanoMolar or less.

All patent and literature references cited in this application are incorporated herein by reference in their entirety.

The invention claimed is:

1. A compound chosen from

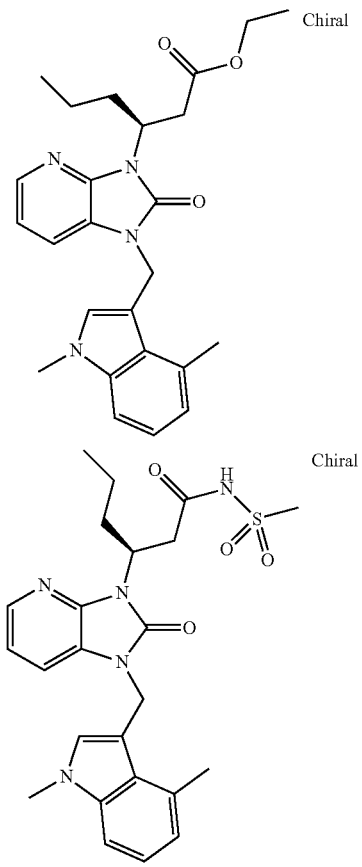

87
-continued
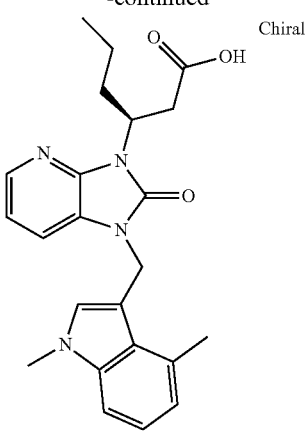
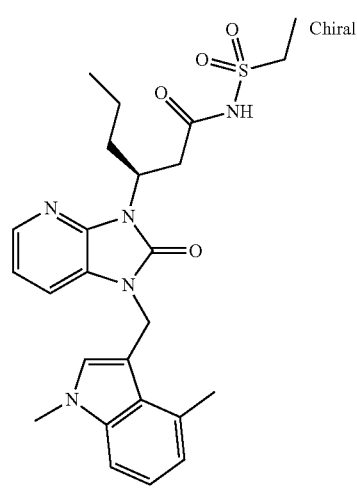
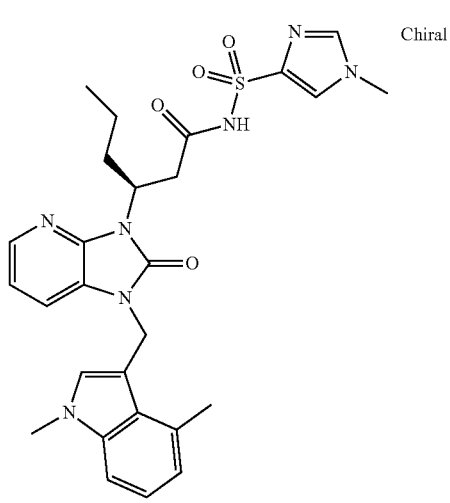
88
-continued
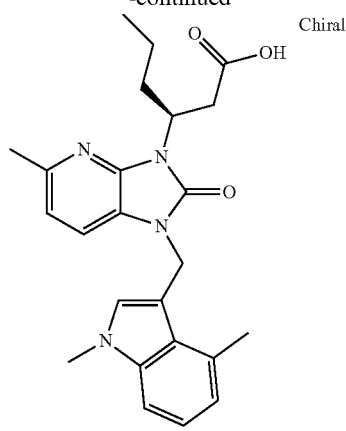
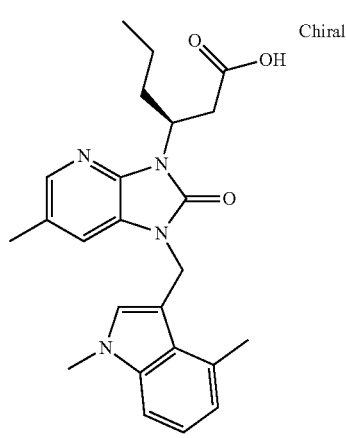
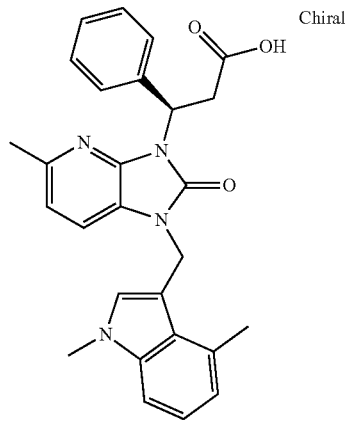

89
-continued
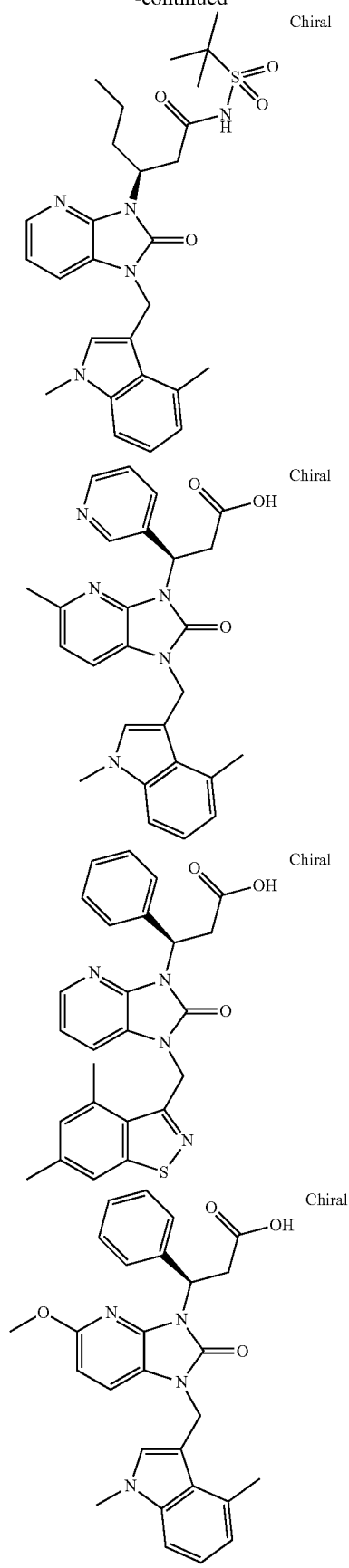
90
-continued
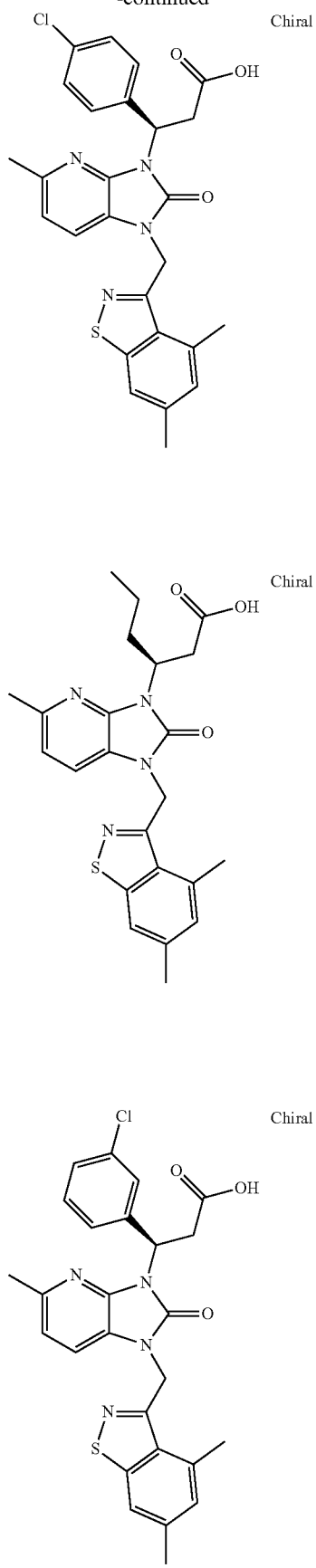

91
-continued
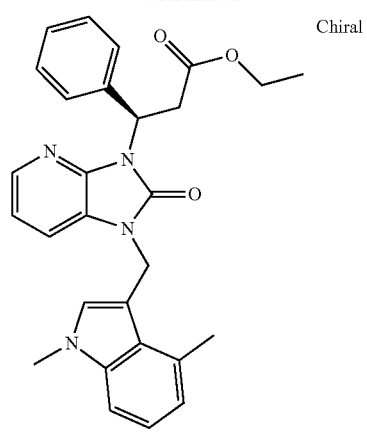
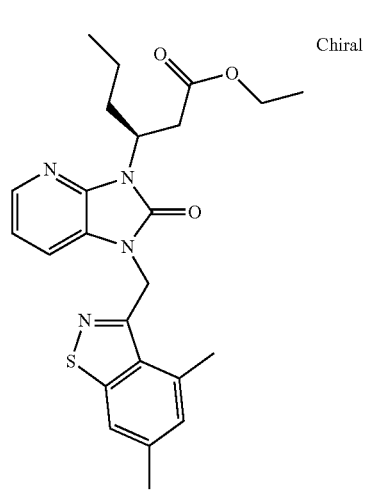
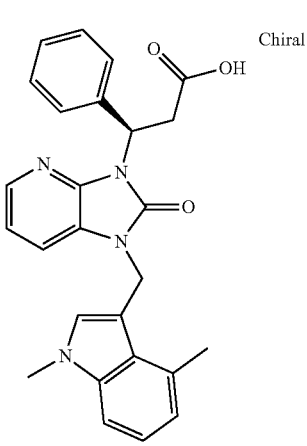
92
-continued
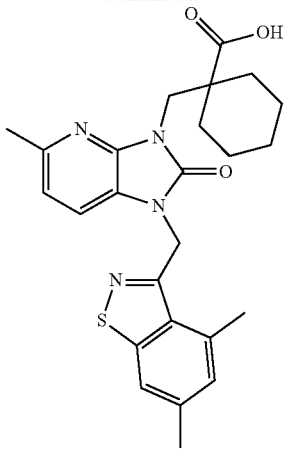
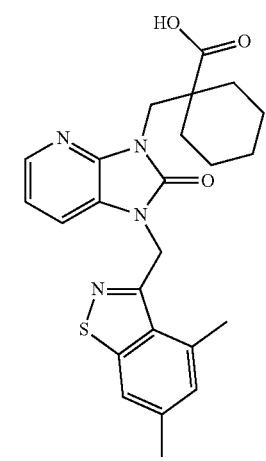
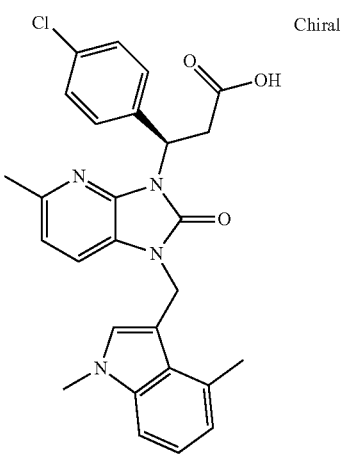

93
-continued
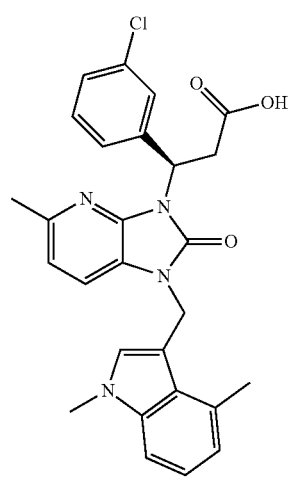
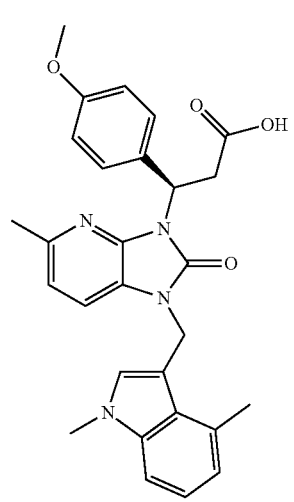
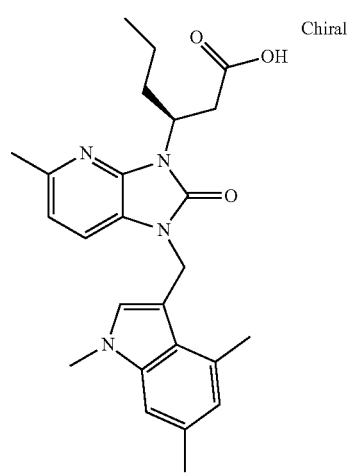
94
-continued
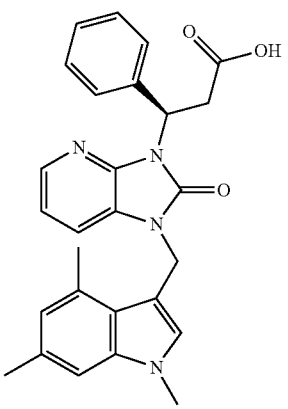
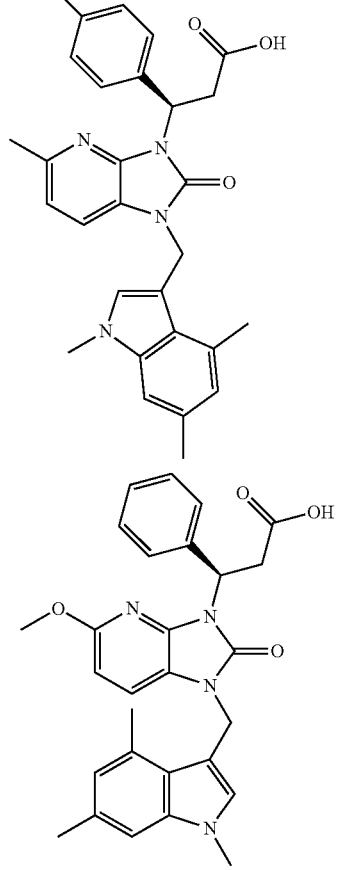
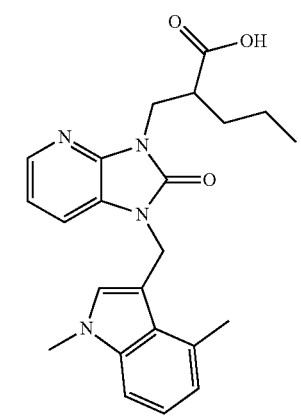

95
-continued
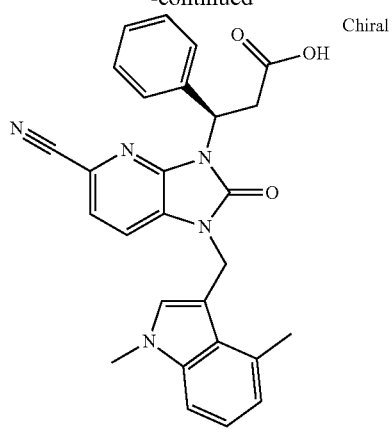
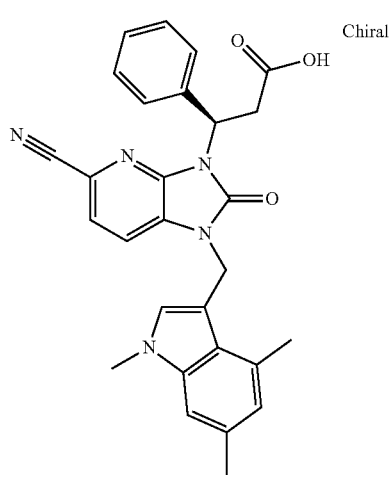
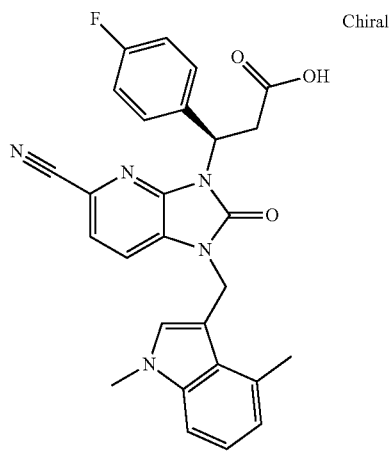
96
-continued
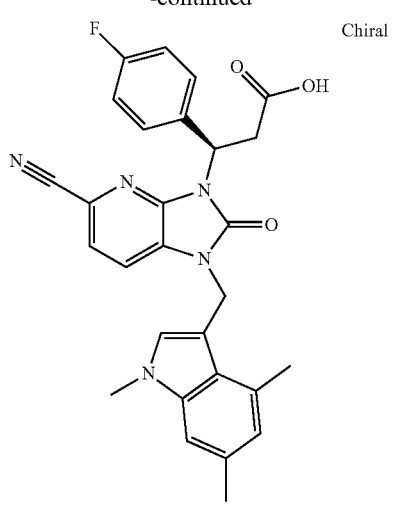
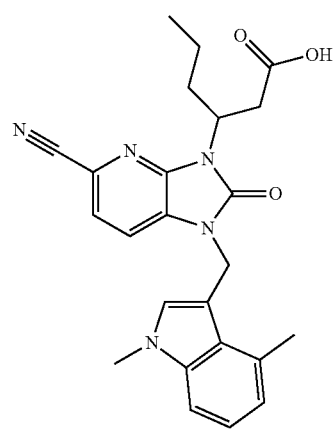
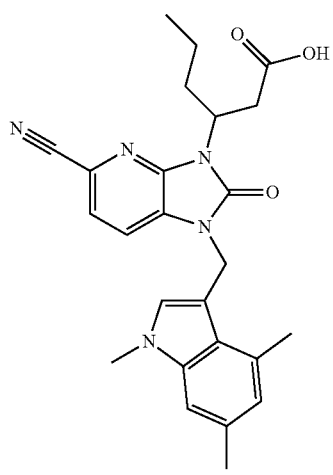

-continued
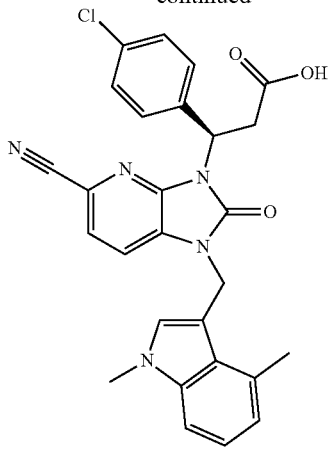
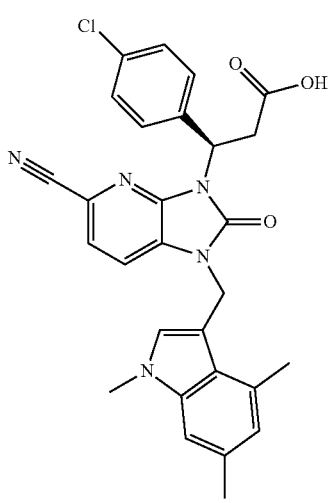
-continued
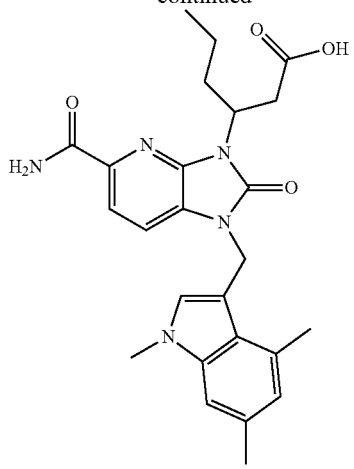
or a pharmaceutically acceptable salt thereof.
2. A pharmaceutical composition comprising a therapeutically effective amount of a compound according to claim 1 and one or more pharmaceutically acceptable carriers and/or adjuvants.
* * * * *